(12) United States Patent
Hauskins et al.

(10) Patent No.: US 12,304,935 B2
(45) Date of Patent: May 20, 2025

(54) IMMUNOMODULATORY POLYPEPTIDES AND RELATED COMPOSITIONS AND METHODS

(71) Applicant: Juno Therapeutics, Inc., Seattle, WA (US)

(72) Inventors: Collin Hauskins, Seattle, WA (US); Allen Ebens, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 820 days.

(21) Appl. No.: 16/320,075

(22) PCT Filed: Jul. 28, 2017

(86) PCT No.: PCT/US2017/044549
§ 371 (c)(1),
(2) Date: Jan. 23, 2019

(87) PCT Pub. No.: WO2018/023093
PCT Pub. Date: Feb. 1, 2018

(65) Prior Publication Data
US 2019/0194283 A1 Jun. 27, 2019

Related U.S. Application Data

(60) Provisional application No. 62/369,017, filed on Jul. 29, 2016.

(51) Int. Cl.
| | | |
|---|---|---|
| C07K 14/52 | (2006.01) |
| A61K 38/00 | (2006.01) |
| A61K 48/00 | (2006.01) |
| A61P 35/00 | (2006.01) |
| A61P 37/06 | (2006.01) |
| C07K 14/535 | (2006.01) |
| C07K 14/54 | (2006.01) |
| C07K 14/575 | (2006.01) |
| C07K 14/61 | (2006.01) |
| C07K 14/705 | (2006.01) |
| C07K 14/71 | (2006.01) |
| C07K 14/725 | (2006.01) |
| C12N 15/62 | (2006.01) |

(52) U.S. Cl.
CPC ............ *C07K 14/521* (2013.01); *A61K 48/00* (2013.01); *A61P 35/00* (2018.01); *A61P 37/06* (2018.01); *C07K 14/52* (2013.01); *C07K 14/535* (2013.01); *C07K 14/54* (2013.01); *C07K 14/57554* (2013.01); *C07K 14/61* (2013.01); *C07K 14/7051* (2013.01); *C07K 14/70596* (2013.01); *C07K 14/71* (2013.01); *C12N 15/62* (2013.01); *A61K 38/00* (2013.01); *C07K 2319/01* (2013.01)

(58) Field of Classification Search
CPC .... C07K 14/521; C07K 14/52; C07K 14/535; C07K 14/54; C07K 14/57554; C07K 14/61; C07K 14/7051; C07K 14/70596; C07K 14/71; C07K 2319/01; A61K 48/00; A61K 38/00; A61P 35/00; A61P 37/06; C12N 15/62
USPC ...................................................... 424/93.21
See application file for complete search history.

(56) References Cited

U.S. PATENT DOCUMENTS

| | | |
|---|---|---|
| 4,235,871 A | 11/1980 | Demetrios et al. |
| 4,452,773 A | 6/1984 | Molday |
| 4,501,728 A | 2/1985 | Geho et al. |
| 4,690,915 A | 9/1987 | Rosenberg |
| 4,795,698 A | 1/1989 | Owen et al. |
| 4,837,028 A | 6/1989 | Allen |
| 5,019,369 A | 5/1991 | Presant et al. |
| 5,087,616 A | 2/1992 | Myers et al. |
| 5,200,084 A | 4/1993 | Liberti et al. |
| 5,219,740 A | 6/1993 | Miller et al. |
| 6,040,177 A | 3/2000 | Riddell et al. |

(Continued)

FOREIGN PATENT DOCUMENTS

| | | |
|---|---|---|
| CA | 2723320 | 11/2008 |
| EP | 0452342 | 11/1994 |

(Continued)

OTHER PUBLICATIONS

Cetuximab—Wikipedia (pp. 1-6; downloaded Nov. 22, 2021.*

(Continued)

*Primary Examiner* — Allison M Fox
*Assistant Examiner* — Hanan Isam Abuzeineh
(74) *Attorney, Agent, or Firm* — MORRISON & FOERSTER LLP

(57) ABSTRACT

Provided herein are immunomodulatory polypeptides containing first and second submits of a cytokine or a chemokine connected by a joining region containing a targeting moiety that binds to a target molecule. In some aspects, the disclosure further relates to engineered cells and compositions comprising the immunomodulatory polypeptides and methods for their administration to subjects. In some embodiments, the cells engineered to contain the immunomodulatory polypeptide, such as T cells, further contain a genetically engineered antigen receptor that specifically binds to antigens, such as a chimeric antigen receptor (CAR). In some embodiments, features of the polypeptides, engineered cells, and methods provide for improved treatment of diseases or disorders, such as by reducing adverse effects of cytokine or chemokine therapy, or increasing activity, efficacy and/or persistence or decreasing immunogenicity of adoptive cell therapy.

15 Claims, 4 Drawing Sheets
Specification includes a Sequence Listing.

(56) References Cited

U.S. PATENT DOCUMENTS

| | | | |
|---|---|---|---|
| 6,060,273 A | 5/2000 | Dirks et al. | |
| 6,207,453 B1 | 3/2001 | Maass et al. | |
| 6,410,319 B1 | 6/2002 | Raubitschek et al. | |
| 6,451,995 B1 | 9/2002 | Nai-Kong et al. | |
| 6,617,135 B1 * | 9/2003 | Gillies | C07K 14/52 435/69.7 |
| 7,070,995 B2 | 7/2006 | Jensen | |
| 7,253,151 B2 | 8/2007 | Sung et al. | |
| 7,265,209 B2 | 9/2007 | Jensen | |
| 7,354,762 B2 | 4/2008 | Jensen | |
| 7,446,179 B2 | 11/2008 | Jensen | |
| 7,446,190 B2 | 11/2008 | Sadelain | |
| 7,446,191 B2 | 11/2008 | Jensen | |
| 7,833,754 B2 | 11/2010 | Felber et al. | |
| 7,910,564 B2 | 3/2011 | Sung et al. | |
| 8,188,220 B2 | 5/2012 | Ruoslahti et al. | |
| 8,324,353 B2 | 12/2012 | Jensen | |
| 8,339,645 B2 | 12/2012 | Nakawaki | |
| 8,398,282 B2 | 3/2013 | Kuhlman et al. | |
| 8,455,625 B2 | 6/2013 | Neri | |
| 8,479,118 B2 | 7/2013 | Lyndersay et al. | |
| 8,536,113 B2 * | 9/2013 | Trikha | C07K 7/08 530/300 |
| 8,556,882 B2 | 10/2013 | Morgan et al. | |
| 8,715,954 B2 | 5/2014 | Triglia et al. | |
| 8,715,964 B2 | 5/2014 | Felber et al. | |
| 8,765,462 B2 | 7/2014 | Medin et al. | |
| 8,846,345 B2 | 9/2014 | Vandenbroeck et al. | |
| 8,911,993 B2 | 12/2014 | June et al. | |
| 2002/0131960 A1 | 9/2002 | Sadelain et al. | |
| 2002/0150914 A1 | 10/2002 | Andersen et al. | |
| 2007/0116690 A1 | 5/2007 | Yang et al. | |
| 2010/0178276 A1 | 7/2010 | Sadelain et al. | |
| 2011/0003380 A1 | 1/2011 | Miltenyi et al. | |
| 2011/0097792 A1 * | 4/2011 | Webster | A61P 37/06 435/325 |
| 2013/0149337 A1 | 6/2013 | Cooper et al. | |
| 2013/0287748 A1 | 10/2013 | June et al. | |
| 2014/0170109 A1 | 6/2014 | Wulhfard | |
| 2014/0206758 A1 | 7/2014 | Felber et al. | |
| 2014/0255363 A1 | 9/2014 | Metelitsa et al. | |
| 2014/0294841 A1 | 10/2014 | Scheinberg et al. | |
| 2016/0045551 A1 | 2/2016 | Brentjens | |
| 2016/0122707 A1 * | 5/2016 | Swee | A61P 31/12 435/372 |

FOREIGN PATENT DOCUMENTS

| | | |
|---|---|---|
| EP | 1268795 | 1/2003 |
| EP | 1418184 | 5/2004 |
| EP | 1569960 | 9/2005 |
| EP | 2150618 | 2/2010 |
| EP | 2424887 | 3/2012 |
| EP | 2537416 | 11/2014 |
| EP | 2755487 | 12/2018 |
| WO | WO 1992/008796 | 5/1992 |
| WO | WO 1994/028143 | 12/1994 |
| WO | WO 1996/024676 | 8/1996 |
| WO | WO 2000/14257 | 3/2000 |
| WO | WO 2001/010912 | 2/2001 |
| WO | WO 2001/068802 | 2/2002 |
| WO | WO 2004/052929 | 10/2004 |
| WO | WO 2008/134879 | 11/2008 |
| WO | WO 2007/084364 | 7/2009 |
| WO | WO 2009/072003 | 9/2009 |
| WO | WO 2009/140206 | 11/2009 |
| WO | WO 2010/033140 | 5/2010 |
| WO | WO 2010/126766 | 11/2010 |
| WO | WO 2011/112935 | 9/2012 |
| WO | WO 2012/129514 | 9/2012 |
| WO | WO 2013/040371 | 5/2013 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2014/139468 | 9/2014 |
| WO | WO 2018/023093 | 2/2018 |

OTHER PUBLICATIONS

Kontermann et al., "Antibody-cytokine fusion proteins". Arch Biochem Biophys. Oct. 15, 2012;526(2): 194-205 (Year: 2012).*

Chmielewski et al., "IL-12 release by engineered T cells expressing chimeric antigen receptors can effectively Muster an antigen-independent macrophage response on tumor cells that have shut down tumor antigen expression," Cancer Res. (2011) 71(17): 5697-5706.

Ahsan A. et al. "Efficacy of an EGFR-Specific Peptide against EGFR-Dependent Cancer Cell Lines and Tumor Xenografts" Neoplasia (2014) vol. 16, Issue 6, pp. 105-114.

Alonos-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.

Andersson et al., "Antimicrobial activities of heparin-binding peptides," Eur J Biochem (2004) 271:1219-1226.

Barret et al., "Chimeric Antigen Receptor Therapy for Cancer," Annual Review of Medicine (2014) 65:333-347.

Baum et al., "Retrovirus vectors: toward the plentivirus?" Mol Ther (2006) 13(6):1050-1063.

Binetruy-Tournaire R. et al. "Identification of a peptide blocking vascular endothelial growth factor (VEGF)-mediated angiogenesis" (2000) Embo J. Apr. 3; 19(7):1525-1533.

Boris-Lawrie et al., "Recent advances in retrovirus vector technology," Curr Opin Genet Develop (1993) 3(1):102-109.

Brash et al., "Strontium phosphate transfection of human cells in primary culture: stable expression of the simian virus 40 large-T-antigen gene in primary human bronchial epithelial cells," Mol. Cell Biol (1987) 7:2031-2034.

Burns et al., "Vesicular stomatitis virus G glycoprotein pseudotyped retroviral vectors: concentration to very high titer and efficient gene transfer into mammalian and nonmammalian cells," Proc Natl Acad Sci USA (1993) 90(17):8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Cavalieri et al., "Human T lymphocytes transduced by lentiviral vectors in the absence of TCR activation maintain an intact immune competence," Blood (2003) 102(2):497-505.

Cheadle et al., "Chimeric antigen receptors for T-cell based therapy," Methods Mol Biol (2012) 907:645-666.

Chen et al., "A targeted IL-15 fusion protein with potent anti-tumor activity." Cancer Biol Ther. 2015; 16(9):1415-21.

Chen et al., "A Heparan Sulfate-Binding Cell Penetrating Peptide for Tumor Targeting and Migration Inhibition," BioMed Research International (2015) article IDS 237969.

Chicaybam et al., "An Efficient Low Cost Method for Gene Transfer to T Lymphocytes, " PLOS One (2013) 8(3):e60298.

Cho et al., "Human mammalian cell sorting using a highly integrated micro-fabricated fluorescence-activated cell sorter (uFACS)," Lab on a Chip (2010) 10:1567-1573.

Chothia et al., "The outline structure of the T-cell alpha beta receptor," Embo J (1988) 7(12):3745-3755.

Clackson et al., "Making antibody fragments using phage display libraries," Nature (1991) 352(6336):624-628.

Cohen et al., "Recombinant antibodies with MHC-restricted, peptide-specific, T-cell receptor-like specificity: new tools to study antigen presentation and TCR-peptide-MHC interactions," J Mol Recogn (2003) 16:324-332.

Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175(9):5799-5808.

(56) References Cited

OTHER PUBLICATIONS

Cooper et al., "T-cell clones can be rendered specific for CD19: toward the selective augmentation of the graft-versus-B-lineage leukemia effect," Blood (2003) 101:1637-1644.

Curran, KJ. et al., "Chimeric Anitgen Receptor T Cells for Cancer Immunotherapy" Journal of Clinical Oncology Vo. 33, No. 15 (2015) pp. 1703-1707.

Davila et al., "CD19 CAR-Targeted T Cells Induce Long-Term Remission and B Cell Aplasia in an Immunocompetent Mouse Model of B Cell Acute Lymphoblastic Leukemia," PLOS One (2013) 8(4):e61338.

De Felipe, "Skipping the co-expression problem: the new 2A "CHYSEL" technology," Genet Vaccines Ther (2004) 2:13.

De Felipe, "Targeting of proteins derived from self-processing polyproteins containing multiple signal sequences," Traffic (2004) 5(8):616-626.

Eyerich et al., "IL-17 and IL-22: siblings, not twins" Trends in Immunology (2010) vol. 31, issue 9, p. 354-361.

Frecha et al., "Advances in the field of lentivector-based transduction of T and B lymphocytes for gene therapy," Mol Ther (2010) 18(10):1748-1757.

Gillies et al., "Antibody-IL-12 fusion proteins are effective in SCID mouse models of prostate and colon carcinoma metastases," J Immunol. (Jun. 15, 1998);160(12):6195-203.

Godin et al., "Microfluidics and photonics for Bio-System-on-a-Chip: a review of advancements in technology towards a microfluidic flow cytometry chip," J Biophotonics (2008) 1(5):355-376.

Hackett et al., "A Transposon and Transposase System for Human Application," Mol Ther (2010) 18:674-683.

Hasan et al., "IL-12 is a heparin-binding cytokine," J Immunol. (Jan. 15, 1999);162(2):1064-70.

Hermans et al., "The VITAL assay: a versatile fluorometric technique for assessing CTL- and NKT-mediated cytotoxicity against multiple targets in vitro and in vivo," J Immunol Methods (2004) 285(1):25-40.

Huang et al., "DNA transposons for modification of human primary T lymphocytes," Methods in Molecular Biology (2009) 506:115-126.

Hudecek et al., "Receptor affinity and extracellular domain modifications affect tumor recognition by ROR1-specific chimeric antigen receptor T cells," Clin Cancer Res (2013) 19(12):3153-3164.

Jiang C. et al."Construction of a Single-Chain Interleukin-12-Expressing Retroviral Vector and its Application in Cytokine Gene Therapy against Experimental Coccidioidomycosis" (1999) Infection and Immunity vol. 67, No. 6. p 2996-3001.

Johnston, "Biolistic transformation: microbes to mice," Nature (1990) 346:776-777.

Jores et al., "Resolution of hypervariable regions in T-cell receptor beta chains by a modified Wu-Kabat index of amino acid diversity," PNAS USA (1990) 87(23):9138-9142.

Karpusas M et al., "The crystal structure of human interferon $\oplus$ at 2.2-Å resolution" (1197) Proc. Natl. Acad. Sci. USA vol. 94, pp. 11813-11818.

Kermer V., at al., "An antibody fusion protein for cancer immunotherapy mimicking IL-15 trans-presentation at the tumor site" Mol Cancer Ther; 11(6) Jun. 2012.

Klebanoff et al., "Sorting through subsets: which T-cell populations mediate highly effective adoptive immunotherapy?" J Immunother (2012) 35(9):651-660.

Kochenderfer et al., "Construction and preclinical evaluation of an anti-CD19 chimeric antigen receptor," J Immunotherapy (2009) 32(7):689-702.

Koste et al., "T-cell receptor transfer into human T cells with ecotropic retroviral vectors," Gene Therapy (2014) 21:533-538.

Lasek et al., "Interleukin 12: still a promising candidate for tumor immunotherapy?" Cancer Immunol Immunother (2014) 63(5):419-435.

LEE and Margolin "Cytokines in cancer immunotherapy" Cancers 2011, 3, 3856-3893.

Lefranc et al., "IMGT unique numbering for immunoglobulin and T cell receptor variable domains and Ig superfamily V-like domains," Dev Comp Immunol (2003) 27(1):55-77.

Leonard et al., "Effects of single-dose interleukin-12 exposure on interleukin-12-associated toxicity and interferon-gamma production," Blood (1997) 90(7):2541-2548.

Leong J.W. et al., "Preactivation with IL-12, IL-15, IL-18 induces CD25 and a functional high-affinity IL-2 receptor on human cytokine-induced memory-like natural killer cells" Biol Blood Narrow Transplant 20 (2014) 463-473.

Li et al., "Directed evolution of human T-cell receptors with picomolar affinities by phage display," Nat Biotechnol (2005) 23(3):349-354.

Lupton et al., "Dominant positive and negative selection using a hygromycin phosphotransferase-thymidine kinase fusion gene," Mol Cell Biol (1991) 11(6):3374-3378.

Manuri et al., "PiggyBac transposon/transposase system to generate CD19-specific T cells for the treatment of B-lineage malignancies," Human Gene Ther (2010) 21:427-437.

Miller et al., "Improved retroviral vectors for gene transfer and expression," Biotechniques (1989) 7(9):980-982.

Miller, "Retrovirus packaging cells," Hum Gene Ther (1990) 1:5-14.

Mullen et al., "Transfer of the bacterial gene for cytosine deaminase to mammalian cells confers lethal sensitivity to 5-fluorocytosine: a negative selection system," Proc Natl Acad Sci USA (1992) 89(1):33-37.

Park et al., "Treating cancer with genetically engineered T cells," Trends Biotechnol (2011) 29(11):550-557.

Parkhurst et al., "Characterization of GeneticallyModifiedT-Cell Receptors that Recognize the CEA:691-699 Peptide in the Context of HLA-A2.1on Human Colorectal Cancer Cells," Clin Cancer Res (2009) 15:169-180.

Pegram H. et al "Tumor-targeted T cells modified to secrete IL-12 eradicate systemic tumors without need for prior conditioning" Blood (2012) 119(18):4133-4141.

Pegram H. J. et al., "CD28z CARs and Armored CARs" Cancer J. 2014; 20(2): 127-133.

Portlano et al., Lack of promiscuity in autoantigen-specific H and L chain combinations as revealed by human H and L chain "roulette," J Immunol (1993) 150(3):880-887.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (2008) 3(3):319-338.

Robson and Hirst "Transcriptional Targeting in Cancer Gene Therapy" Journal of Biomedicine and Biotechnology 2003:2 (2003) 110-137.

Rosenberg, "Cell transfer immunotherapy for metastatic solid cancer—what clinicians need to know," Nat Rev Clin Oncol (2011) 8(10):577-585.

Sadelain et al., "The basic principles of chimeric antigen receptor design," Cancer Discov (2013) 3(4):388-398.

Scarpa et al., "Characterization of recombinant helper retroviruses from Moloney-based vectors in ecotropic and amphotropic packaging cell lines," Virology (1991) 180(2):849-852.

Sharma et al., "Efficient Sleeping Beauty DNA Transposition From DNA Minicircles," Mol Ther Nucleic Acids (2013) 2(2):e74.

Suzuki et al., "Liposome-Mediated Gene Therapy Using HSV-TK/Ganciclovir under the Control of Human PSA Promoter in Prostate Cancer Cells," Urol Int (2001) 67:216-223.

Szoka et al., "Comparative properties and methods of preparation of lipid vesicles (liposomes)." Annu Rev Biophys Bioeng (1980) 9:467-508.

Tam Em et al "Noncompetitive Inhibition of Hepatocyte Growth Factor-dependent Met Signaling by a Phage-derived Peptide" Journal of Molecular Biol (2009) vol. 385, issue 1, pp. 79-90.

Tedder and Leonard "Regulatory B cells-IL-35 and IL-21 regulate the regulators" Nature Reviews Rheumatology (2014) 10, 452-453.

Terakura et al., "Generation of CD19-chimeric antigen receptor modified CD8+ T cells derived from virus-specific central memory T cells," Blood (2012) 1:72-82.

(56) References Cited

OTHER PUBLICATIONS

Themeli et al.. "Generation of tumor-targeted human T lymphocytes from induced pluripotent stem cells for cancer therapy," Nat Biotechnol (2013) 31(10):928-933.

Tsukahara et al., "CD19 target-engineered T-cells accumulate at tumor lesions in human B-cell lymphoma xenograft mouse models," Biochem Biophys Res Commun (2013) 438(1):84-89.

Turnis M. et al., "Inhibitory receptors as targets for cancer immunotherapy" (2015) vol. 45, Issue 7 pp. 1892-1905.

Turtle et al., "Engineered T cells for anti-cancer therapy," Curr Opin Immunol (2012) 24(5):633-639.

Van Tendeloo et al., "High-level transgene expression in primary human T lymphocytes and adult bone marrow CD34+ cells via electroporation-mediated gene delivery," Gene Ther (2000) 7(16):1431-1437.

Varela-Rohena et al., "Control of HIV-1 immune escape by CD8 T cells expressing enhanced T-cell receptor," Nat Med (2008) 14(12):1390-1395.

Verhoeyen et al., "Lentiviral Vector Gene Transfer into Human T Cells," Methods in Molecular Biology (2009) 506:97-114.

Vicari D. et al. "Engineered Conformation-dependent VEGF Peptide Mimics are Effective in Inhibiting VEGF Signaling Pathways" The Journal of Biological Chemistry (2011) 286, 13612-13625.

Wadwa et al., "Receptor mediated glycotargeting," J Drug Target (1995) 3(2):111-127.

Wang et al., "Phenotypic and functional attributes of lentivirus-modified CD19-specific human CD8+ central memory T cells manufactured at clinical scale," J Immunother (2012) 35(9):689-701.

Wigler et al., "Transfer of purified herpes virus thymidine kinase gene to cultured mouse cells," Cell (1977) 11(1):223-232.

Wu et al., "Adoptive T-cell therapy using autologous tumor-infiltrating lymphocytes for metastatic melanoma: current status and future outlook," Cancer J (2012) 18(2):160-175.

* cited by examiner

IMMUNOMODULATORY POLYPEPTIDES AND RELATED COMPOSITIONS AND METHODS

CROSS-REFERENCE TO RELATED APPLICATIONS

This application is a U.S. National Stage of International Application No. PCT/US2017/044549 filed Jul. 28, 2017, which claims priority from U.S. provisional application No. 62/369,017 filed Jul. 29, 2016, entitled "IMMUNOMODULATORY POLYPEPTIDES AND RELATED COMPOSITIONS AND METHODS," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042004200SeqList.txt, created on Jan. 11, 2019, which is 143,099 bytes in size. The information in electronic format of the Sequence Listing is incorporated by reference in its entirety.

FIELD

The present disclosure relates in some aspects to immunomodulatory polypeptides containing a first and second peptide, such as a first and second subunit of a cytokine or a chemokine, connected by a joining region containing a targeting moiety that binds to a target molecule. In some aspects, the disclosure further relates to engineered cells and compositions comprising the immunomodulatory polypeptides and methods for their administration to subjects. In some embodiments, the cells engineered to contain the immunomodulatory polypeptide, such as T cells, further contain a genetically engineered recombinant receptor that specifically binds to antigens, such as a chimeric antigen receptor (CAR). In some embodiments, features of the polypeptides, engineered cells, and methods provide for improved treatment of diseases or conditions, e.g., cancer, such as by reducing adverse effects of cytokine or chemokine therapy or increasing the activity, efficacy and/or persistence of cell therapy.

BACKGROUND

Various strategies are available for treatment of diseases or conditions such as cancers or tumors, including the administration of cytokines or chemokines. Further, strategies are available for engineering immune cells to express genetically engineered recombinant receptors, such as chimeric antigen receptors (CARs), and administering compositions containing such cells to subjects. Improved strategies are needed to increase efficacy of the treatments, for example, by reducing adverse effects of cytokine or chemokine administration, improving the persistence and/or survival of engineered cells, or reducing the immunogenicity of such therapies upon administration to subjects. Provided are compositions, cells, and methods that meet such needs.

SUMMARY

Provided herein is an immunomodulatory polypeptide containing a first peptide; a second peptide; and a joining region connecting the first and second peptides, wherein the joining region contains a targeting moiety that binds to a target molecule. In some embodiments, at least one of the first and second peptide is a cytokine or chemokine, a subunit a cytokine or chemokine or is a functional portion of the cytokine or chemokine.

In some of any such embodiments, the first peptide is a cytokine or chemokine, a subunit of a cytokine or chemokine, or is a functional portion of the cytokine or chemokine. In some of any such embodiments, the second peptide is a cytokine or chemokine, a subunit of a cytokine or chemokine, or is a functional portion of the cytokine or chemokine. In some of any such embodiments, both the first and second peptide are independently a cytokine or chemokine, a subunit of a cytokine or chemokine or a functional portion of the cytokine or chemokine.

In some of any such embodiments, the first peptide and the second peptide are the same cytokine or chemokine, or functional portions thereof, or are the same subunit of the same cytokine or chemokine. In some of any such embodiments, the first and second peptide are a different cytokine or chemokine, or functional portions thereof, or are a different subunit of the same or different cytokine or chemokine. In some of any such embodiments, the first peptide is a first subunit of a cytokine or chemokine and the second peptide is a second subunit of the cytokine or chemokine.

In some of any such embodiments, the cytokine or chemokine is a monomer. In some of any such embodiments, the first and/or second peptide independently contain(s) a subunit of a cytokine or chemokine that is a multimeric protein.

In some of any such embodiments, the first or second peptide is a tag or label.

Provided herein is an immunomodulatory polypeptide containing a first peptide containing a first subunit of a cytokine or chemokine or a functional portion thereof; a second peptide containing a second subunit of the cytokine or chemokine or a functional portion thereof; and a joining region connecting the first and second peptides, wherein the joining region contains a targeting moiety that binds to a target molecule. In some of any such embodiments, the cytokine or chemokine is a homodimer or heterodimer.

In some of any such embodiments, the joining region further contains at least one polypeptide linker linking the targeting moiety to the first or second peptide.

In some of any such embodiments, the cytokine or chemokine or subunit or functional portion thereof is selected from the group consisting of IL-12, IL-15, IL-2, IL-18, GM-CSF, IL-7, IL-21, IFNα, IFNβ, IFNγ, IL-17, IL-23, IL-3, IL-4, IL-5, IL-6, IL-9, IL-11, IL-13, IL-27, Erythropoietin, G-CSF, Growth hormone, Prolactin, Oncostatin M, and Leukemia inhibitory factor or a subunit or functional portion thereof. In some of any such embodiments, the first or second peptide independently contains a subunit of a cytokine or chemokine selected from IL-12, IL-23, IL-27 and IL-35 or a functional portion thereof.

In some of any such embodiments, the first or second peptide is independently a subunit of IL-12 or a functional portion thereof. In some embodiments, the first peptide contains an IL-12 p35 subunit or an IL-12 p40 subunit or a functional portion thereof and the second peptide contains the other of the IL-12 p35 subunit and the IL-12 p40 subunit or a functional portion thereof.

Provided herein is an immunomodulatory polypeptide containing a first peptide containing a p35 subunit of IL-12 or a functional portion thereof; a second peptide containing a p40 subunit of IL-12 or a functional portion thereof; and a joining region connecting the first and second peptides, wherein the joining region contains a targeting moiety that binds to a target molecule. In some of any such embodiments, the p35 subunit contains the sequence of amino acids set forth in SEQ ID NO: 10 or a sequence that has at least 95% sequence identity thereto and/or the p40 subunit contains the sequence of amino acids set forth in SEQ ID NO: 11 or a sequence that has at least 95% sequence identity thereto.

In some of any such embodiments, the joining region further contains at least one polypeptide linker linking the targeting moiety to the p35 subunit or the p40 subunit. In some of any such embodiments, the polypeptide linker contains from about 2 to about 20 amino acids. In some of any such embodiments, the polypeptide linker contains the sequence GGGGS(n), wherein n is 1-5 (SEQ ID NO:29). In some of any such embodiments, the polypeptide linker contains the sequence set forth in any of SEQ ID NOs: 7-9.

In some of any such embodiments, the joining region contains two polypeptide linkers. In some of any such embodiments, the targeting moiety is contained between a first polypeptide linker and a second polypeptide linker. In some of any such embodiments, the target molecule is associated with a disease or disorder. In some aspects, the disease or disorder is an infectious disease or disorder, an autoimmune disease, an inflammatory disease, or a tumor or a cancer.

In some of any such embodiments, the target molecule is associated with a tumor or present on a tumor. In some of any such embodiments, the target molecule is a tumor antigen. In some of any such embodiments, the target molecule is selected from the group consisting of: hepatocyte growth factor (HGF), heparin, VEGF, VEGF-A, VEGFR2, VEGFR3, HER2, PD-1, tenascin-C, CTLA-4, LAGS, PD-L1, EGFR, EPCAM, RANKL, NG2 proteoglycan, CD20, CD52, CD19, CD3, CD30, IL-6, CD38, SLAMF7, GD2, CD13, CD274, CD279, CD40L, and CD47.

In some of any such embodiments, the targeting moiety contains from about 3 to about 300 amino acids, about 3 to about 100 amino acids, about 3 to about 20 amino acids, about 6 to about 20 amino acids, or about 10 amino acids. In some of any such embodiments, the targeting moiety exhibits a $k_{off}$ rate for binding the target molecule that is about $0.5 \times 10^{-4}$ sec$^{-1}$ or less, about $1 \times 10^{-4}$ sec$^{-1}$ or less, about $2 \times 10^{-4}$ sec$^{-1}$ or less, about $3 \times 10^{-4}$ sec$^{-1}$ or less, about $4 \times 10^{-4}$ sec$^{-1}$ or less, about $5 \times 10^{-4}$ sec$^{-1}$ or less, about $1 \times 10^{-3}$ sec$^{-1}$ or less, about $1.5 \times 10^{-3}$ sec$^{-1}$ or less, about $2 \times 10^{-3}$ sec$^{-1}$ or less, about $3 \times 10^{-3}$ sec$^{-1}$ or less, about $4 \times 10^{-3}$ sec$^{-1}$ or less, about $5 \times 10^{-3}$ sec$^{-1}$ or less, about $1 \times 10^{-2}$ sec or less, or about $5 \times 10^{-1}$ sec$^{-1}$ or less. In some of any such embodiments, the dissociation constant ($K_D$) of the targeting moiety to the target molecule is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM.

In some of any such embodiments, the targeting moiety is or contains an antibody or antibody fragment. In some aspects, the antibody fragment is a single chain fragment. In some embodiments, the antibody fragment is a single domain antibody containing the variable heavy chain region. In some aspects, the antibody fragment contains antibody variable regions joined by a flexible linker. In some of any such embodiments, the antibody fragment contains an scFv.

In some of any such embodiments, the targeting moiety contains a variable heavy (VH) chain and/or variable light (VL) chain of an antibody selected from the group consisting of: trastuzumab, pertuzumab, ramucirumab, atezolizumab, bevacizumab, panitumumab, cetuximab, necitumumab, denosumab, nivolumab, pembrolizumab, rituximab, ofatumumab, obinutuzumab, alemtuzumab, blinatumomab, brentuximab vedotin, siltuximab, ipilimumab, daratumumab, elotuzumab, dinutuximab, catumaxomab. In some of any such embodiments, the targeting moiety contains a $V_H$ chain and/or $V_L$ chain of an anti-EPCAM antibody. In some of any such embodiments, the targeting moiety contains the sequence set forth in SEQ ID NO: 17, 24 or 25, or a sequence that has at least 95% sequence identity to SEQ ID NO: 17, 24 or 25 and binds to the target molecule.

In some of any such embodiments, the immunomodulatory polypeptide contains the sequence set forth in SEQ ID NO: 6, or a sequence that has at least 95% sequence identity to such a sequence.

In some of any such embodiments, the targeting moiety is or contains a peptide binding motif. In some of any such embodiments, the targeting moiety is a heparin binding peptide. In some aspects, the heparin binding peptide (HBP) is derived from fibronectin or BMP4, and/or is of bovine origin.

In some of any such embodiments, the targeting moiety is selected from the group consisting of a hepatocyte growth factor (HGF) binding peptide, a VEGF binding peptide, a VEGF-A binding peptide, a VEGFR2 binding peptide, an EPCAM binding peptide, a HER2 binding peptide, a PD-1 binding peptide, a tenascin-C binding peptide, a CTLA-4 binding peptide, a LAGS binding peptide, a PD-L1 binding peptide, a EGFR binding peptide, a RANKL binding peptide, a CD20 binding peptide, a CD52 binding peptide, a CD19 binding peptide, a CD3 binding peptide, a CD30 binding peptide, a IL-6 binding peptide, a CD38 binding peptide, a SLAMF7 binding peptide, a GD2 binding peptide, a CD274 binding peptide, a CD279 binding peptide, a CD40L binding peptide, and a CD47 binding peptide. In some of any such embodiments, the targeting moiety contains a HGF binding peptide or an EGFR binding peptide (EGFRBP).

In some of any such embodiments, the targeting moiety contains the sequence set forth in any of SEQ ID NOs: 13, 14, 15, 16, 26, 27 or 28, or a sequence that has at least 95% sequence identity to such a sequence and binds to the target molecule.

In some of any such embodiments, the immunomodulatory polypeptide contains the sequence set forth in any of SEQ ID NOs: 1-5, or a sequence that has at least 95% sequence identity to such a sequence.

In some of any such embodiments, immunomodulatory polypeptide exhibits increased activity to stimulate via the IL-12R compared to a recombinant IL-12 not containing the joining region. In some of any such embodiments, the immunomodulatory polypeptide exhibits increased binding to a target cell expressing the target molecule as compared with its binding to a cell not expressing the target molecule. In some embodiments, the increased activity and/or binding is/are by greater than 1.2-fold, greater than 1.5-fold, greater than 2.0-fold, greater than 3.0-fold, greater than 4.0-fold, greater than 5.0-fold or greater than 10.0-fold. In some embodiments, the increased activity and/or binding is greater than that exhibited by a reference immunomodulatory polypeptide containing a polypeptide linker between subunits but not containing the targeting moiety.

Provided herein is a polynucleotide encoding the immunomodulatory polypeptide according to any one of the embodiments described above. In some aspects, the polynucleotide further contains a signal sequence. In some instances, the signal sequence encodes a signal peptide derived from CD33. In some aspects, the signal peptide contains the sequence set forth in SEQ ID NO: 18, or a sequence that has at least 95% sequence identity to such a sequence.

In some of any such embodiments, the polynucleotide further contains at least one promoter that is operatively linked to control expression of the immunomodulatory polypeptide. In some embodiments, the expression of the immunomodulatory polypeptide is inducible or conditional. In some of any such embodiments, the polynucleotide further contains a conditional promoter, enhancer, or transactivator. In some aspects, the conditional promoter, enhancer, or transactivator is an inducible promoter, enhancer, or transactivator or a repressible promoter, enhancer, or transactivator.

In some embodiments, the promoter, enhancer or transactivator is a T cell activation factor. For example, the promoter, enhancer or transactivator contains a binding site for one or more T cell transcription factor(s). In some embodiments, the promoter, enhancer or transactivator contains a binding site for nuclear factor of activated T-cells (NFAT), C/EBP, STAT1, STAT2, and/or NFκB.

In some embodiments, activation of the promoter, enhancer, or transactivator is a conditional, optionally an inducible promoter, enhancer, or transactivator or a repressible promoter, enhance or transactivator.

In some embodiments, the promoter, enhancer or transactivator is active in the presence of one or more conditions present in the tumor microenvironment. The one or more conditions present in the tumor microenvironment can be selected from hypoxia, low glucose, acidic pH and/or oxidative stress.

In some embodiments, the one or more conditions present in the tumor microenvironment is hypoxia. In some of such embodiments, the polynucleotide is operatively linked to a promoter, and the promoter is a HIF-1-alpha-responsive promoter. In some embodiments the polynucleotide is operatively linked to a promoter, and the promoter contains one or more hypoxia response element(s). An exemplary hypoxia response element contains the sequence 5'-(A/G)CGT(G/C)(G/C)-3'. In such embodiments, the promoter can be an erythropoietin (Epo), VEGF-A, phosphoglycerate kinase 1 (PGK1), lactate dehydrogenase A (LDH A), aldolase A (ALDA) or glyceraldehyde 3-phosphate dehydrogenase (GAPDH) promoter. The promoter can have the sequence set forth in any of SEQ ID NOs: 85-90.

In some embodiments, the one or more conditions present in the tumor microenvironment is low glucose. In some of such embodiments, the polynucleotide is operatively linked to a promoter that is a GRP78 or hexokinase II promoter.

In some embodiments, the promoter, enhancer, or transactivator is inducible by radiation, heat or in the presence of a drug.

In some embodiments, the promoter is a radiation-inducible promoter. Exemplary radiation-inducible promoters can contain a CArG element or a CC(A+T rich)$_6$GG motif. In some embodiments, the radiation-inducible promoter is an EGR-1, Waf-1, RecA, or cIAP2 promoter or is a synthetic promoter, such as a promoter with a sequence set forth in SEQ ID NOs 92-95.

In some embodiments, the promoter, enhancer or transactivator is a heat-inducible promoter, enhancer or transactivator. In some of such embodiments, the heat-inducible promoter, enhancer, or transactivator contains a heat shock element (HSE). In some embodiments, the heat-inducible promoter, enhancer, or transactivator is a heat shock promoter (HSP), such as an HSP70B promoter or a Gadd 153 promoter.

In some embodiments the promoter, enhancer, or transactivator is a drug-inducible promoter, enhancer, or transactivator. In some instances, the inducible promoter, enhancer, or transactivator contains a Lac operator sequence, a tetracycline operator sequence, a galactose operator sequence, a doxycycline operator sequence, a rapamycin operator sequence, a tamoxifen operator sequence, or a hormone-responsive operator sequence, or an analog thereof. In some embodiments, the inducible promoter contains a tetracycline response element (TRE). In some embodiments, the drug-inducible promoter, enhancer, or transactivator contains a multidrug resistance (mdr1) gene promoter.

In some of any such embodiments, the polynucleotide contains a single nucleic acid sequence. In some of any such embodiments, the polynucleotide contains a first nucleic acid sequence encoding the immunomodulatory polypeptide and a second nucleic acid sequence encoding a recombinant receptor. In some aspects, the recombinant receptor is or contains a chimeric antigen receptor (CAR). In some embodiments, the polynucleotide further contains at least one promoter that is operatively linked to control expression of the immunomodulatory polypeptide and/or the recombinant receptor.

In some of any such embodiments, the polynucleotide further contains an internal ribosome entry site (IRES) between the first and second nucleic acid sequences to yield translation products of the first and second nucleic acid sequences after translation. In some embodiments, the polynucleotide contains a nucleic acid sequence encoding a linking peptide between the first and second nucleic acid sequences, wherein the linking peptide separates the translation products of the first and second nucleic acid sequences during or after translation. In some aspects, the linking peptide contains a self-cleaving peptide, or a peptide that causes ribosome skipping, optionally a T2A peptide.

Any of the embodied polynucleotides can be optimized to remove CpG motifs and/or codon-optimized. In some embodiments, the polynucleotide is human codon-optimized.

Provided herein is a vector containing the polynucleotide according to any one of the embodiments described above. In some embodiments, the vector is a viral vector. In some aspects, the vector is a retroviral vector. In some instances, the vector is a lentiviral vector or a gammaretroviral vector.

Provided herein is an engineered cell containing the immunomodulatory polypeptide according to any one of the embodiments described above. In some of any such embodiments, provided is an engineered cell containing the polynucleotide according to any one of the embodiments described above. In some embodiments, the engineered cell contains the vector according to any one of the embodiments described above.

In some of any such embodiments, the engineered cell secretes the immunomodulatory polypeptide. In some embodiments, the engineered cell further contains a recombinant receptor. In some instances, the recombinant receptor binds to a target antigen that is associated with a disease or disorder. In some aspects, the disease or disorder is an infectious disease or disorder, an autoimmune disease, an inflammatory disease, or a tumor or a cancer. In some embodiments, the target antigen is a tumor antigen.

In some of any such embodiments, the target antigen is selected from the group consisting of ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1). In some embodiments, the targeting moiety is human or is derived from a human protein.

In some of any such embodiments, the immunomodulatory protein is not immunogenic and/or does not induce an immune response in a subject in which it is administered.

In some of any such embodiments, the recombinant receptor is a functional non-TCR antigen receptor or a transgenic TCR. In some embodiments, the recombinant receptor is a chimeric antigen receptor (CAR). In some of any such embodiments, the recombinant receptor contains an extracellular portion containing an antigen-binding domain. In some instances, the antigen-binding domain is or contains an antibody or an antibody fragment. In some aspects, the antibody fragment is a single chain fragment. In some embodiments, the fragment contains antibody variable regions joined by a flexible linker. In some of any such embodiments, the fragment contains an scFv.

In some of any such embodiments, the recombinant receptor contains an intracellular signaling region. In some aspects, the intracellular signaling region is capable of inducing a primary activation signal in a T cell, is a T cell receptor (TCR) component, and/or contains an immunoreceptor tyrosine-based activation motif (ITAM). In some instances, the intracellular signaling region is or contains an intracellular signaling domain of a CD3-zeta (CD3ζ) chain or a signaling portion thereof.

In some of any such embodiments, the engineered cell further contains a transmembrane domain linking the extracellular portion and the intracellular signaling region. In some embodiments the intracellular region contains an intracellular signaling domain. In some of any such embodiments, the recombinant receptor further contains a costimulatory signaling domain. In some instances, the costimulatory signaling domain contains an intracellular signaling domain of a T cell costimulatory molecule or a signaling portion thereof. In some aspects, the costimulatory signaling domain contains an intracellular signaling domain of CD28, 4-1BB or ICOS or a signaling portion thereof. In some embodiments, the costimulatory signaling domain is between the transmembrane domain and the intracellular signaling region.

In some of any such embodiments, the engineered cell is a T cell. In some of any such embodiments, the engineered cell is a CD8+ T cell or a CD4+ T cell.

In some of any such embodiments, the engineered cell exhibits increased persistence and/or survival compared to cells not engineered or compared to cells containing a recombinant receptor but not the immunomodulatory polypeptide. In some of any such embodiments, the engineered cell exhibits increased activity to stimulate via the IL-12R compared to a recombinant IL-12 not containing the joining region. In some embodiments, the reference IL-12 does not contain a joining region or contains a joining region that consists of any of the sequences set forth in SEQ ID NOs 7-9.

In some of any such embodiments, the engineered cell secretes an immunomodulatory polypeptide that exhibits increased binding to a target cell expressing the target molecule as compared with its binding to a cell not expressing the target molecule. In some of any such embodiments, the engineered cell effects increased killing of a target cell expressing the target molecule compared to killing of cells not expressing the target molecule. In some of any such embodiments, the increased persistence, activity, binding, and/or killing is greater than effected by a reference engineered cell expressing or secreting an immunomodulatory polypeptide containing a polypeptide linker between subunits but not containing the targeting moiety.

Provided herein is a composition containing the immunomodulatory polypeptide according to any one of the embodiments described above. Provided herein is a composition containing the engineered cell according to any one of the embodiments described above. In some embodiments, the composition further contains a pharmaceutically acceptable excipient.

Provided herein is a method of treatment including administering the immunomodulatory polypeptide according to any one of the embodiments described above, the engineered cell according to any one of the embodiments described above, or the composition of according to any one of the embodiments described above, to a subject having a disease or disorder. In some instances, the immunomodulatory polypeptide specifically binds to a target molecule expressed by a cell associated with the disease or disorder. In some aspects, the engineered cell expresses a recombinant receptor that specifically binds to an antigen associated with the disease or condition. In some embodiments, the disease or disorder is a cancer, a tumor, an autoimmune disease or disorder, or an infectious disease.

DETAILED DESCRIPTION

Figure 1:
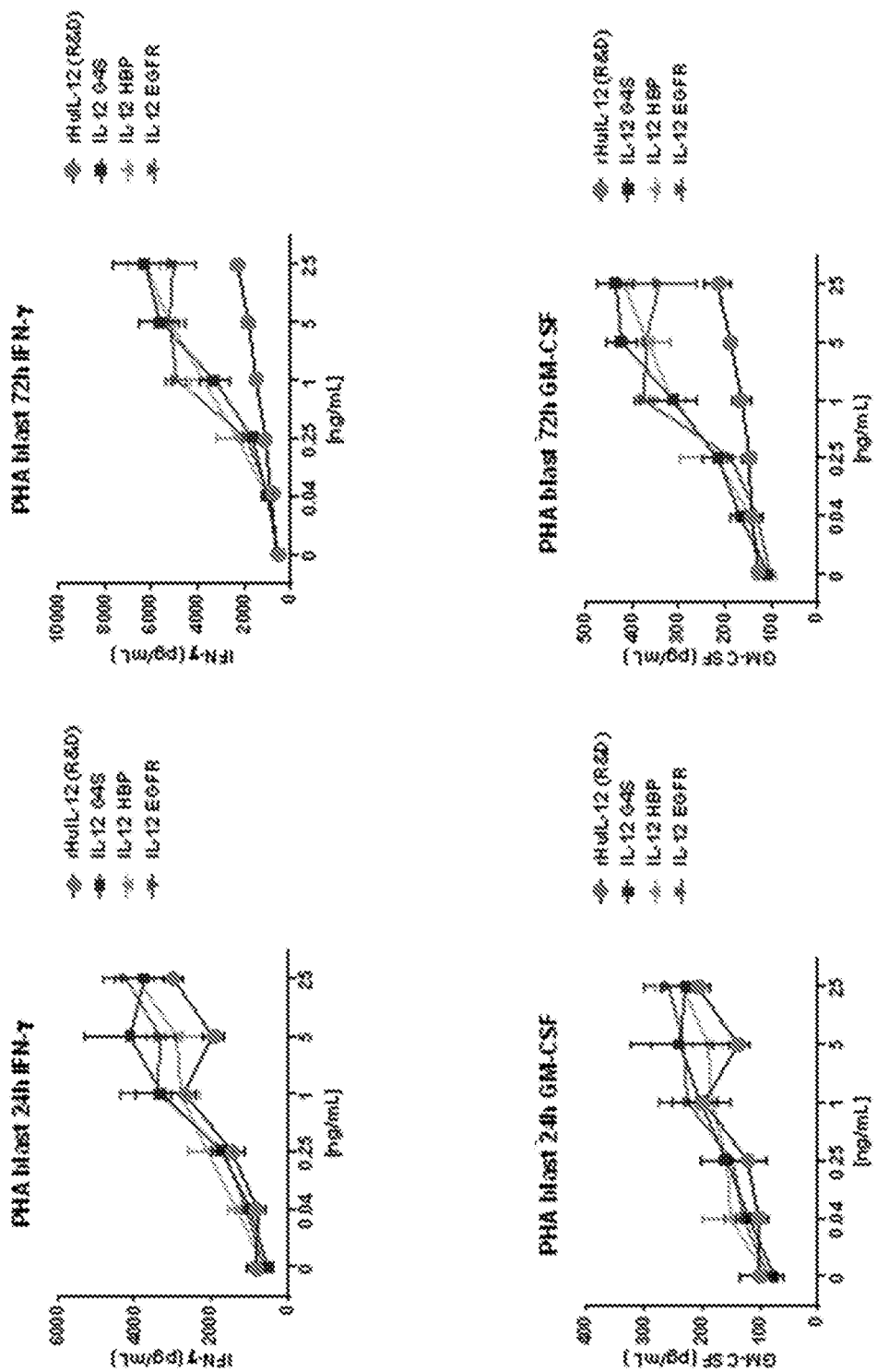
FIG. 1 depicts interferon gamma (IFN-γ) secretion in PHA blasts following stimulation with recombinant human IL-12 (rHuIL-12), a scIL-12 or immunomodulatory polypeptides containing either a HBP targeting moiety (IL-12 HBP) or an EGFR targeting moiety (IL-12 EGFR).

Provided herein are immunomodulatory polypeptides, including those containing a first and second peptide connected by a joining region containing a targeting moiety that binds to a target molecule. In some embodiments, the first and second peptides are independently a first and second cytokine or chemokine, a subunit of a cytokine or chemokine or a functional portion of a cytokine or chemokine. In some embodiments, the immunomodulatory protein contains a first subunit and second subunit of a cytokine or chemokine connected by a joining region containing a targeting moiety that binds to a target molecule. In some embodiments, the cytokine is IL-12 and the immunomodulatory polypeptide contains a p35 and p40 subunit of IL-12 linked by a joining region containing a targeting moiety that binds to a target molecule. In some embodiments, the target molecule is a molecule overexpressed in or specific to a diseased environment, such as a tumor microenvironment, such as on a cell present in a diseased or tumor microenvironment. Also provided are compositions and engineered cells containing the immunomodulatory polypeptides and methods of administering such compositions and cells.

Administration of various peptides, such as cytokines and chemokines, can be effective in treating diseases and conditions, such as cancer. However, certain such treatments, such as those involving systemic administration of natural or unmodified cytokines, can be associated with unwanted effects, such as those arising from activity of the molecules at sites other than cells or tissues of the disease or condition, e.g., tumor cells. As such, current methods may be not entirely satisfactory, and improved efficacy and safety are desired.

In some embodiments, the immunomodulatory polypeptides provided herein specifically bind to a target molecule expressed by a cell associated with the disease or condition. Thus, in some cases, the immunomodulatory polypeptide is targeted to tissues and cells that express known target molecules, e.g., tumor cells. In some cases, targeting of the immunomodulatory polypeptide to cells containing the target molecule is associated with less unwanted, or more desired, outcomes as compared to treatment with the peptides, such as cytokines or chemokines, e.g., recombinant human cytokines or chemokines, not containing a linker or targeting moiety.

In some aspects, the provided embodiments exhibit comparable safety, and improved efficacy, as compared to a reference treatment regime or composition, such as compared to cell-based or local delivery-based administration of the cytokine or a related or unmodified version thereof, generally designed for tumor-localization of the cytokine. In some respects, the provided embodiments include systemic administration, with increased safety profile as compared to systemic administration of native or unmodified version of the cytokine molecule.

In some aspects, the cytokine is interleukin 12 (IL-12). IL-12 is typically a mediator of innate and cellular immunity. In some contexts, IL-12 effects anti-tumor and anti-metastatic activity. Generally, IL-12 acts on T cells and NK cells. Functions of IL-12 include the priming of the T helper 1 (Th1) immune responses and IFN-γ secretion by NK cells. Typically, IL-12 generates the Th1 response by promoting the differentiation of naïve T cells, during initial encounter with an antigen, into a population of Th1-cells capable of producing large amounts of IFN-γ following activation. In some contexts, IL-12 serves as a co-stimulus for maximum secretion of IFN-γ by differentiated Th1 cells responding to a specific antigen. IL-12, in some contexts, stimulates the development of IFN-γ producing Th1 cells from populations of resting memory T cells interacting with an antigen to which they have been previously exposed. Thus, in some aspects, IL-12 can promote or mediate immune effector functions to enhance anti-tumor immune responses, including in connection with administration of cells in adoptive cell therapy.

In some cases, as with many other cytokines, however, certain studies involving the systemic administration of recombinant human native IL-12 has been observed to be associated with toxicity, such as systemic toxicity. In some cases, clinical trials in patients with cancer have revealed promising therapeutic activities, but have typically also shown that systemically administered native recombinant human IL-12 can have side effects (Lasek et al. (2014) Cancer Immunol. Immunother., 63:419-435). In some aspects, such certain types of administration of such recombinant IL-12 can result in grade 3 or grade 4 toxicity as assessed in accord with National Cancer Institute Groups Toxicity Criteria Scale (Creekmore et al. (eds): Biologic Therapy of Cancer. Philadelphia, PA, Lippincott, 1991, p. 76). In some cases, clinical symptoms of toxicity can include, for example, one or more of fatigue, dyspnea, stomatitis, acidosis or gastrointestinal hemorrhage. In some cases, laboratory adverse events can include one or more of leukopenia, neutropenia, hyperbilirubinemia, elevated AST, elevated ALT, thrombocytopenia, elevated creatinine or elevated alkaline phosphatase. Assays to assess and determine the presence or absence of potentially adverse effects are known (see e.g. Leonard et al. (1997) Blood, 90:2541-2548). Various other delivery routes and modified constructs, however, such as local, e.g., tumor site administration of IL-12 and/or introduction of cells such as T cells that naturally secrete or are engineered to secrete IL-12, e.g., in a tumor-targeted manner, have been observed to be safe and associated with fewer or no toxic outcomes or risk thereof. In some examples, engineered T cells, such as those expressing chimeric antigen receptors, also expressing recombinant or exogenous IL-12, e.g., a single-chain heterodimeric format, that is secreted, have been reported with encouraging results (Pegram et al. (2012) Blood, 119:4133-4141).

In some embodiments, the provided immunomodulatory polypeptides, such as IL-12 immunomodulatory polypeptides, when administered, may result in reduced toxicity, such as reduced systemic toxicity, as compared with other treatments such as other types of therapy involving the administration, such as systemic administration, of recombinant human IL-12. In some embodiments, the provided cells expressing such immunomodulatory polypeptides, when administered to a patient, may result in reduced toxicity, such as reduced systemic toxicity, as compared with other treatments, such as other types of therapy involving administration of cells expressing recombinant human IL-12. In some embodiments, the toxicity resulting from the provided cells is reduced, or further reduced, by modifying the polynucleotide that yields the recombinant or exogenous IL-12, such that the expression is inducible or condition-dependent, such as by incorporation of one or more inducible or condition-dependent promoter and/or regulatory elements as described herein below. For example, the polynucleotide can be modified to employ one or more inducible promoters such that IL-12 expression is effected upon administration of an exogenous agent, such as radiation, heat, or a drug or small molecule, and is otherwise not expressed. In other examples, expression of the recombinant or exogenous IL-12 can be restricted such that expression only occurs in particular microenvironments, such as tumor microenvironments (e.g., hypoxic conditions). Regulation of IL-12 expression such that the recombinant IL-12 is expressed only in targeted regions of the body and/or only under particular conditions can mitigate the toxicity of administering IL-12-expressing cells.

In some embodiments, subjects, when administered with a provided immunomodulatory polypeptide containing a targeting moiety or cells expressing or secreting such immunomodulatory polypeptide, such as a provided IL-12 immunomodulatory polypeptide containing a targeting moiety, do not or do not, on average of the subjects administered, exhibit severe toxicity or an IL-12 associated toxicity that is grade 3 or higher. In some aspects, compared to other methods, the subjects exhibit the same or reduced toxicity or lack thereof and increased efficacy, such as an increase in the immunomodulatory effects of the IL-12 as provided herein.

In some cases, the structure of the immunomodulatory polypeptide is such that when the targeting moiety binds the target molecule, e.g., on the surface of a target cell, the first and second peptides (e.g. subunits of the cytokine or chemokine) are oriented away from the target cell. In some such cases, the subunits of the cytokine or chemokine are oriented towards an adjacent non-target cell, such as an immune cell. In some embodiments, such an orientation may discourage the cytokine or chemokine from binding to its receptor on the target cells. In some aspects, such an orientation may promote binding of the cytokine or chemokine to its receptor on immune cells, e.g., T cells. In some instances, such an orientation may effect enhanced T cell stimulation as compared with other immunomodulatory polypeptides not designed to be oriented away from the target cell or designed to be oriented toward the target cell. In some cases, the structure, e.g., order and size of components, of the joining region is designed to promote binding of the targeting moiety to a target cell while promoting binding of the first and second peptides, e.g. first and second cytokines or subunits of cytokines, toward an adjacent non-target cell, e.g. such that the subunits are oriented away from the target cell.

In some aspects, the targeting moiety is connected to one or both of peptides, such as one or both of the subunits. In some embodiments, the targeting moiety is configured between the first and second peptide, such as the first and second subunit of a cytokine or chemokine (e.g. IL-12). In some embodiments, the targeting moiety is connected directly or indirectly, such as via one or more linker(s). In some instances, the joining region further contains at least one polypeptide linker linking the targeting moiety to the first or second peptides, such as first or second subunit of a cytokine or chemokine. In some cases, the joining region contains two or more polypeptide linkers. For example, in some aspects, the first peptide (e.g. first subunit) is attached to a first polypeptide linker, the first polypeptide linker is attached to a first end of the targeting moiety, and a second polypeptide linker is attached to the second end of the targeting moiety and the second peptide (e.g. second subunit). Thus, in some contexts, the targeting moiety is flanked between two or more polypeptide linkers that attach it to one or both of the peptides (e.g. subunits of a cytokine or chemokine). In some embodiments, such an order of the components of the joining region promotes the orientation of the peptides (e.g., cytokine or chemokine subunits) away from the target cell.

In some aspects, the size, e.g., length, of the joining region is such that the first and second peptides (e.g., cytokine or chemokine subunits) will be oriented in the desired orientation. In some embodiments, the joining region is no more than 400, 300, 250, 200, 150, 100, 50, 40, 30, 25, 20, 15, 10, or 5 amino acids. In some aspects, the length of the joining region is between or between about 200 and 400 amino acids, between or between about 100 and 200 amino acids, or between or between about 5 and 50 amino acids, such as between or between about 10 and 50 amino acids, 10 and 40 amino acids, 10 and 30 amino acids, 10 and 20 amino acids, 20 and 50 amino acids, 20 and 40 amino acids, 20 and 30 amino acids, 30 and 50 amino acids or 30 and 40 amino acids.

In some embodiments, the nucleic acid molecule encoding the immunomodulatory polypeptide is operably linked to a promoter, such as an inducible, conditional, or activation-induced promoter or enhancer. In some embodiments, the promoter or enhancer controls expression of the immunomodulatory polypeptide. Thus, in some contexts, the immunomodulatory polypeptide is expressed essentially only when the promoter or enhancer is active. For example, in some cases, a conditional promoter may be activated by co-administration of a molecule or compound or may be downregulated following co-administration with a molecule or compound.

In some aspects, the expression of the immunomodulatory polypeptide is effected in the presence of immune cell, e.g., T cell, activation, such as by a T cell activation factor. For example, in some instances, the promoter, enhancer or other response element or portion thereof is recognized by a transcription factor to drive expression of a gene whose activity is normally turned on by T cell activation. In some embodiments, the T cell activation factor can be a regulatory domain or region (e.g. promoter, enhancer or other response element) of a transcription factor whose activity is turned on by T cell activation. In some embodiments, the T cell activation factor is responsive to one or more of T cell activation, signal strength of TCR signaling and/or quality of TCR signaling.

In some embodiments, the T cell activation factor can be a regulatory element, such as a promoter, enhancer or response element or elements, that contains a binding site for a T cell transcription factor, and that thereby is associated with the downstream activity of a T cell transcription factor. In some embodiments, the transcription factor is nuclear factor of activated T-cells (NFAT), C/EBP, STAT1, STAT2, or NFκB. For example, in some embodiments, the T cell activation factor contains a response element or elements recognized by a nuclear factor of activated T-cells (NFAT), C/EBP, STAT1, STAT2, and NFκB. In some embodiments, the T cell activation factor can contain a regulatory element or elements recognized by or responsive to one or two, and in some cases three or more, unique transcription factors.

In some aspects, where the expression of the immunomodulatory polypeptide is controlled by such a conditional, inducible, or activation-induced promoter or enhancer, the efficacy of the immunomodulatory polypeptide is improved as compared to a recombinant human cytokine or chemokine or to an immunomodulatory polypeptide not operably linked to such a promoter or enhancer. In some aspects, the risk of potential side effects or outcomes indicative of toxicity, of the immunomodulatory polypeptide operably linked to such a promoter or enhancer is reduced as compared with a recombinant human cytokine or chemokine or to an immunomodulatory polypeptide not operably linked to such a promoter or enhancer. In some aspects, efficacy is increased comparatively. For example, in some cases, provided immunomodulatory polypeptides whose expression is inducibly or conditionally controlled may have decreased or no expression in non-target tissues, but can be activated in the vicinity of target tissues. In some embodiments, the nucleic acid molecules encoding the provided immunomodulatory polypeptides operably linked to an activation-induced promoter may have decreased or no expression in non-target tissues, but can be activated in the vicinity of target tissues where an immune response has been elicited. Such approaches may result in reduced potential for unwanted outcomes or increased efficacy as compared with other compositions and methods.

In some embodiments, the immunomodulatory polypeptide exhibits activity to stimulate a receptor recognized by the first or second peptide, e.g. a cytokine or chemokine receptor. In some embodiments, the activity of the immunomodulatory polypeptide to stimulate the receptor is increased as compared to an immunomodulatory protein not containing the targeting moiety, such as a recombinant cytokine or chemokine not comprising the joining region. In some aspects, the immunomodulatory polypeptide exhibits increased binding to a target cell expressing the target molecule as compared with its binding to a cell not expressing the target molecule. In some aspects, the increased activity and/or binding is greater than effected by a reference immunomodulatory polypeptide containing a polypeptide linker between subunits but not containing the targeting moiety. In any of such aspects, the increase is by greater than 1.2-fold, greater than 1.5-fold, greater than 2.0-fold, greater than 3.0-fold, greater than 4.0-fold, greater than 5.0-fold or greater than 10.0-fold.

In some embodiments, the immunomodulatory protein is not immunogenic. In some cases, the immunomodulatory polypeptide does not induce an immune response in a subject to which it is administered. In some cases, the immunomodulatory polypeptide is less immunogenic than polypeptide molecules, e.g. cytokines or chemokines, linked to larger targeting moiety and/or connected via larger joining regions. In some embodiments, a subject that is administered the immunomodulatory protein or a cell expressing the immunomodulatory protein does not exhibit or exhibits a reduced immune response or a particular type or degree of immune response, against the immunomodulatory protein compared to administration of such other alternative molecules or administration of cells expressing such other alternative molecules, respectively. The type of immune response that is reduced may be a detectable immune response, a humoral immune response, and/or a cell-mediated immune response.

In some embodiments, the immunomodulatory polypeptide is provided on or in combination with cells encoding a recombinant receptor, such as a chimeric antigen receptor (CAR), that combines a ligand-binding domain (e.g. antibody or antibody fragment) that provides specificity for a desired antigen (e.g., tumor antigen) with an activating intracellular domain portion, such as a T cell activating domain, providing a primary activation signal. In some embodiments, the provided immunomodulatory polypeptides and recombinant receptors, when genetically engineered into immune cells can modulate T cell stimulation and/or activation, thereby resulting in genetically engineered cells with improved longevity, survival and/or persistence in vivo, such as for use in adoptive cell therapy methods.

Thus, also provided are cells, such as cells that contain the immunomodulatory polypeptide and/or an engineered recombinant receptor, such as described herein. In some embodiments, the cells are capable of secreting or are designed to secrete the immunomodulatory peptide, such as the cytokine, such as the modified IL-12 polypeptide. Methods for engineering cells to secrete polypeptides are described, for example, in Pegram et al. (2012) Blood, 119:4133-4141; U.S. publ. No. US20160045551 and U.S. publ. No. US20100178276.

In some embodiments, the engineered cell secretes the immunomodulatory polypeptide that exhibits increased binding to a target cell expressing the target molecule as compared with its binding to a cell not expressing the target molecule, and/or exhibits increased binding to the target cell and/or increased efficacy as compared to a cell expressing a cytokine, e.g., IL-12, that is otherwise the same or substantially the same or similar to the immunomodulatory polypeptide, but that does not contain modifications, is not a single-chain molecule, does not include a linker, is not a heterodimeric single chain molecule, and/or does not have the targeting moiety. In some aspects, the engineered cell effects increased killing of a target cell expressing the target molecule compared to killing of cells not expressing the target molecule.

In some cases, the immunomodulatory polypeptides and recombinant receptors can be expressed in cells to produce genetically engineered T cells that, when administered to a subject, exhibit one or more properties that are improved compared to a reference cell composition that does not express or secrete the immunomodulatory protein. In some instances, the increased persistence, activity, binding, and/or killing is greater than effected by a reference composition comprising an engineered cell not expressing an immunomodulatory polypeptide or expressing or secreting an immunomodulatory polypeptide comprising a polypeptide linker between subunits but not comprising the targeting moiety. Thus, in some cases, one or more properties of administered genetically engineered cells that can be improved or increased or greater compared to administered cells of a reference composition include decreased immunogenicity, increased activation, and increased survival and/or persistence.

In some embodiments, engineered cells containing the immunomodulatory polypeptide and a recombinant receptor exhibit increased persistence and/or survival compared to cells not engineered or compared to cells comprising a recombinant receptor but not the immunomodulatory polypeptide. In some embodiments, a genetically engineered cell with increased persistence exhibits better potency in a subject to which it is administered. In some aspects, the persistence of administered cells is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

Also provided are methods and uses of the immunomodulatory polypeptides and engineered cells containing or secreting the immunomodulatory polypeptides, such as for use in adoptive therapy in the treatment of cancers. Further provided are methods for engineering, preparing, and producing the immunomodulatory polypeptides and cells, compositions containing the immunomodulatory polypeptides and cells, and kits and devices containing and for using, producing and administering the compositions or cells. Also provided are methods, compounds, and compositions for producing the engineered cells. Provided are nucleic acids, such as constructs, e.g., viral vectors encoding the immunomodulatory polypeptides and/or genetically engineered recombinant receptors, and methods for introducing such nucleic acids into the cells, such as by transduction. Also provided are compositions containing the immunomodulatory polypeptides and engineered cells, and methods, kits, and devices for administering the cells and compositions to subjects, such as for adoptive cell therapy. In some aspects, the cells are isolated from a subject, engineered, and administered to the same subject. In other aspects, they are isolated from one subject, engineered, and administered to another subject.

I. Immunomodulatory Polypeptides

Provided in some embodiments are immunomodulatory polypeptides, such as those containing a first peptide, a second peptide and a joining region connecting the first and second peptides. In some embodiments, the first and second peptide can be or are derived from a cytokine or chemokine, a subunit of a cytokine or chemokine or a functional portion of a cytokine or chemokine thereof. In some embodiments, the first peptide is a first subunit of a cytokine or chemokine or a functional portion thereof and the second peptide is a second subunit of the cytokine or chemokine or a functional portion thereof, which are joined by a joining region connecting the first and second subunits. In some embodiments, the term "functional portion" may mean a sufficient portion of a cytokine or chemokine or a subunit of a cytokine or chemokine that is capable of binding to its cognate receptor to transduce their signal, and effect immunomodulation activity. A functional portion typically contains at least or about at least 30%, 40%, 50%, 60%, 70%, 80%, 90%, 95% or more of the full length sequence, such as the full length mature sequence lacking the signal peptide. In some embodiments, the provided immunomodulatory polypeptides or cells containing such a peptide exhibit increased or decreased activity to stimulate or suppress the activity or response of a cognate receptor, compared to a reference polypeptide, wherein the reference polypeptide is the polypeptide, such as a recombinant protein, not containing the joining region or the reference polypeptide is a recombinant protein containing the joining region, but not containing a targeting moiety. In some embodiments, the immunomodulatory polypeptide exhibits increased affinity for one or more cognate receptor and exhibits increased activity to stimulate via the one or more cognate receptor, compared to the reference polypeptide. In other embodiments, the immunomodulatory polypeptide exhibits decreased affinity for one or more cognate receptor and exhibits decreased stimulation via the one or more cognate receptor, compared to the reference polypeptide. In some embodiments, the immunomodulatory receptor modulates activity by exhibiting increased or decreased binding affinity for the cognate receptor, compared to the reference polypeptide.

In some embodiments, the immunomodulatory polypeptide exhibits a binding affinity for the target molecule with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from or from about $10^{-5}$ M to or to about $10^{-15}$ M, such as from or from about $10^{-6}$ M to or to about $10^{-12}$ M, from or from about $10^{-7}$ M to or to about $10^{-11}$ M, from or from about $10^{-6}$ M to or to about $10^{-8}$ M, or from or from about $10^{-7}$ M to or to about $10^{-8}$ M. In some embodiments, the $K_D$ of the targeting moiety to the target molecule is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, 1, 0.5, or 0.1 nM, such as between at or about 0.1 nM and at or about 15 nM, e.g., between at or about 1 and at or about 10 nM. In some embodiments, the $K_D$ of the targeting moiety to the target molecule is at or about or less than at or about 1 nM, 100 picomolar (pM), 90 pM, 80 pM, 70 pM, 60 pM, 50 pM, 40 pM, 30 pM, 25 pM, 20 pM, 15 pM, 10 pM, or 1 pM, such as between at or about 10 pM and at or about 100 pM, e.g., between at or about 25 pM and at or about 75 pM.

In some aspects, the increased activity and/or binding is greater or less than the activity and/or binding effected by a reference immunomodulatory polypeptide containing a polypeptide linker between subunits but not containing a targeting moiety. In some such aspects, the increase is by greater than 1.2-fold, greater than 1.5-fold, greater than 2.0-fold, greater than 3.0-fold, greater than 4.0-fold, greater than 5.0-fold or greater than 10.0-fold.

In some embodiments, the immunomodulatory polypeptide specifically or preferentially binds to a target molecule expressed by a cell associated with the disease or disorder. In some cases, the joining region contains a targeting moiety that binds to a target molecule. In some instances, the joining region further contains at least one polypeptide linker linking the targeting moiety to the first or second subunit.

A. Cytokines/Chemokines

In some embodiments, the cytokine or chemokine or a subunit or functional portion thereof is a cytokine or chemokine that binds to a receptor on an immune cell, such as a T cell, NK cell, macrophage, dendritic cell or other immune cell. In some embodiments, the immune cell is a T cell, such as a CD4+ or CD8+ T cell.

In some embodiments, the first or second cytokine or chemokine or a first or second subunit of a cytokine or chemokine or a functional portion thereof is independently selected from IL-12, IL-15, IL-2, IL-18, GM-CSF, IL-7, IL-21, IFNα, IFNβ, IFNγ, IL-17, IL-23, IL-3, IL-4, IL-5, IL-6, IL-9, IL-11, IL-13, IL-27, Erythropoietin, G-CSF, Growth hormone, prolactin, oncostatin M, leukemia inhibitory factor, IL-22, and IL-10, or a subunit or functional portion thereof. In some embodiments, it is mammalian, such as is human. Non-limiting examples of exemplary cytokines and chemokines of a provided immunomodulatory protein are set forth in Table 1. In some embodiments, the first and second peptide, such as a first and second cytokine or chemokine, subunit of a cytokine or chemokine or functional portion thereof, does not contain a signal peptide or propeptide.

In some embodiments, the first or second peptide, such as a first or second cytokine or chemokine, subunit of a cytokine or chemokine or functional portion thereof independently contains a sequence of amino acids set forth in any of SEQ ID NOs:10, 11 and 30-69 or a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOs:10, 11 and 30-69.

TABLE 1

Exemplary cytokine and chemokine sequences

| Name | Sequence | UniProt ID | SEQ ID NO. |
|---|---|---|---|
| IL-12 alpha (p35), IL-35 alpha | RNLPVATPDPGMFPCLHHSQNLLRAVSNMLQKARQ TLEFYPCTSEEIDHEDITKDKTSTVEACLPLELTK NESCLNSRETSFITNGSCLASRKTSFMMALCLSSI YEDLKMYQVEFKTMNAKLLMDPKRQIFLDQNMLAV IDELMQALNFNSETVPQKSSLEEPDFYKTKIKLCI LLHAFRIRAVTIDRVMSYLNAS | P29459 | 10 |
| IL-12 beta (p40) | IWELKKDVYVVELDWYPDAPGEMVVLTCDTPEEDG ITWTLDQSSEVLGSGKTLTIQVKEFGDAGQYTCHK GGEVLSHSLLLLHKKEDGIWSTDILKDQKEPKNKT FLRCEAKNYSGRFTCWWLTTISTDLTFSVKSSRGS SDPQGVTCGAATLSAERVRGDNKEYEYSVECQEDS ACPAAEESLPIEVMVDAVHKLKYENYTSSFFIRDI IKPDPPKNLQLKPLKNSRQVEVSWEYPDTWSTPHS YFSLTFCVQVQGKSKREKKDRVFTDKTSATVICRK NASISVRAQDRYYSSSWSEWASVPCS | P29460 | 11 |
| IL-15 | GIHVFILGCFSAGLPKTEANWVNVISDLKKIEDLI QSMHIDATLYTESDVHPSCKVTAMKCFLLELQVIS LESGDASIHDTVENLIILANNSLSSNGNVTESGCK ECEELEEKNIKEFLQSFVHIVQMFINTS | P40933 | 30 |
| IL-2 | APTSSSTKKTQLQLEHLLLDLQMILNGINNYKNPK LTRMLTFKFYMPKKATELKHLQCLEEELKPLEEVL NLAQSKNFHLRPRDLISNINVIVLELKGSETTFMC EYADETATIVEFLNRWITFCQSIISTLT | P60568 | 31 |
| IL-18 | MAAEPVEDNCINFVAMKFIDNTLYFIAEDDENLES DYFGKLESKLSVIRNLNDQVLFIDQGNRPLFEDMT DSDCRDNAPRTIFIISMYKDSQPRGMAVTISVKCE KISTLSCENKIISFKEMNPPDNIKDTKSDIIFFQR SVPGHDNKMQFESSSYEGYFLACEKERDLFKLILK KEDELGDRSIMFTVQNED | Q14116 | 32 |
| GM-CSF | APARSPSPSTQPWEHVNAIQEARRLLNLSRDTAAE MNETVEVISEMFDLQEPTCLQTRLELYKQGLRGSL TKLKGPLTMMASHYKQHCPPTPETSCATQIITFES FKENLKDFLLVIPFDCWEPVQE | P04141 | 33 |
| IL-7 | DCDIEGKDGKQYESVLMVSIDQLLDSMKEIGSNCL NNEFNFFKRHICDANKEGMFLFRAARKLRQFLKMN STGDFDLHLLKVSEGTTILLNCTGQVKGRKPAALG EAQPTKSLEENKSLKEQKKLNDLCFLKRLLQEIKT CWNKILMGTKEH | P13232 | 34 |
| IL-21 | QGQDRHMIRMRQLIDIVDQLKNYVNDLVPEFLPAP EDVETNCEWSAFSCFQKAQLKSANTGNNERIINVS IKKLKRKPPSTNAGRRQKHRLTCPSCDSYEKKPPK EFLERFKSLLQKMIHQHLSSRTHGSEDS | Q9HBE4 | 35 |
| IFN alpha-1/13 | CDLPETHSLDNRRTLMLLAQMSRISPSSCLMDRHD FGFPQEEFDGNQFQKAPAISVLHELIQQIFNLFTT KDSSAAWDEDLLDKFCTELYQQLNDLEACVMQEER VGETPLMNADSILAVKKYFRRITLYLTEKKYSPCA WEVVRAEIMRSLSLSTNLQERLRRKE | P01562 | 36 |
| IFN alpha-2 | CDLPQTHSLGSRRTLMLLAQMRKISLFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRAEIMRSFSLSTNLQESLRSKE | P01563 | 37 |
| IFN alpha-4 | CDLPQTHSLGNRRALILLAQMGRISHFSCLKDRHD FGFPEEEFDGHQFQKAQAISVLHEMIQQTFNLFST EDSSAAWEQSLLEKFSTELYQQLNDLEACVIQEVG VEETPLMNEDSILAVRKYFQRITLYLTEKKYSPCA WEVVRAEIMRSLSFSTNLQKRLRRKD | P05014 | 38 |

TABLE 1-continued

Exemplary cytokine and chemokine sequences

| Name | Sequence | UniProt ID | SEQ ID NO. |
|---|---|---|---|
| IFN alpha-5 | LGCDLPQTHSLSNRRTLMIMAQMGRISPFSCLKDR HDFGFPQEEFDGNQFQKAQAISVLHEMIQQTFNLF STKDSSATWDETLLDKFYTELYQQLNDLEACMMQE VGVEDTPLMNVDSILTVRKYFQRITLYLTEKKYSP CAWEVVRAEIMRSFSLSANLQERLRRKE | P01569 | 39 |
| IFN alpha-6 | SLDCDLPQTHSLGHRRTMMLLAQMRRISLFSCLKD RHDFRFPQEEFDGNQFQKAEAISVLHEVIQQTFNL FSTKDSSVAWDERLLDKLYTELYQQLNDLEACVMQ EVWVGGTPLMNEDSILAVRKYFQRITLYLTEKKYS PCAWEVVRAEIMRSFSSSRNLQERLRRKE | P05013 | 40 |
| IFN alpha-7 | CDLPQTHSLRNRRALILLAQMGRISPFSCLKDRHE FRFPEEEFDGHQFQKTQAISVLHEMIQQTFNLFST EDSSAAWEQSLLEKFSTELYQQLNDLEACVIQEVG VEETPLMNEDFILAVRKYFQRITLYLMEKKYSPCA WEVVRAEIMRSFSFSTNLKKGLRRKD | P01567 | 41 |
| IFN alpha-8 | CDLPQTHSLGNRRALILLAQMRRISPFSCLKDRHD FEFPQEEFDDKQFQKAQAISVLHEMIQQTFNLFST KDSSAALDETLLDEFYIELDQQLNDLESCVMQEVG VIESPLMYEDSILAVRKYFQRITLYLTEKKYSSCA WEVVRAEIMRSFSLSINLQKRLKSKE | P32881 | 42 |
| IFN alpha-10 | CDLPQTHSLGNRRALILLGQMGRISPFSCLKDRHD FRIPQEEFDGNQFQKAQAISVLHEMIQQTFNLFST EDSSAAWEQSLLEKFSTELYQQLNDLEACVIQEVG VEETPLMNEDSILAVRKYFQRITLYLIERKYSPCA WEVVRAEIMRSLSFSTNLQKRLRRKD | P01566 | 43 |
| IFN alpha-14 | CNLSQTHSLNNRRTLMLMAQMRRISPFSCLKDRHD FEFPQEEFDGNQFQKAQAISVLHEMMQQTFNLFST KNSSAAWDETLLEKFYIELFQQMNDLEACVIQEVG VEETPLMNEDSILAVKKYFQRITLYLMEKKYSPCA WEVVRAEIMRSLSFSTNLQKRLRRKD | P01570 | 44 |
| IFN alpha-16 | CDLPQTHSLGNRRALILLAQMGRISHFSCLKDRYD FGFPQEVFDGNQFQKAQAISAFHEMIQQTFNLFST KDSSAAWDETLLDKFYIELFQQLNDLEACVTQEVG VEEIALMNEDSILAVRKYFQRITLYLMGKKYSPCA WEVVRAEIMRSFSFSTNLQKGLRRKD | P05015 | 45 |
| IFN alpha-17 | CDLPQTHSLGNRRALILLAQMGRISPFSCLKDRHD FGLPQEEFDGNQFQKTQAISVLHEMIQQTFNLFST EDSSAAWEQSLLEKFSTELYQQLNNLEACVIQEVG MEETPLMNEDSILAVRKYFQRITLYLTEKKYSPCA WEVVRAEIMRSLSFSTNLQKILRRKD | P01571 | 46 |
| IFN alpha-21 | CDLPQTHSLGNRRALILLAQMGRISPFSCLKDRHD FGFPQEEFDGNQFQKAQAISVLHEMIQQTFNLFST KDSSATWEQSLLEKFSTELNQQLNDLEACVIQEVG VEETPLMNVDSILAVKKYFQRITLYLTEKKYSPCA WEVVRAEIMRSFSLSKIFQERLRRKE | P01568 | 47 |
| IFN beta-1 | MSYNLLGFLQRSSNFQCQKLLWQLNGRLEYCLKDR MNFDIPEEIKQLQQFQKEDAALTIYEMLQNIFAIF RQDSSSTGWNETIVENLLANVYHQINHLKTVLEEK LEKEDFTRGKLMSSLHLKRYYGRILHYLKAKEYSH CAWTIVRVEILRNFYFINRLTGYLRN | P01574 | 48 |
| IFN gamma | QDPYVKEAENLKKYFNAGHSDVADNGTLFLGILKN WKEESDRKIMQSQIVSFYFKLFKNFKDDQSIQKSV ETIKEDMNVKFFNSNKKKRDDFEKLTNYSVTDLNV QRKAIHELIQVMAELSPAAKTGKRKRSQMLFRGRR ASQ | P01579 | 49 |
| IL-17A | GITIPRNPGCPNSEDKNFPRTVMVNLNIHNRNTNT NPKRSSDYYNRSTSPWNLHRNEDPERYPSVIWEAK CRHLGCINADGNVDYHMNSVPIQQEILVLRREPPH CPNSFRLEKILVSVGCTCVTPIVHHVA | Q16552 | 50 |
| IL-17F | RKIPKVGHTFFQKPESCPPVPGGSMKLDIGIINEN QRVSMSRNIESRSTSPWNYTVTWDPNRYPSEVVQA QCRNLGCINAQGKEDISMNSVPIQQETLVVRRKHQ GCSVSFQLEKVLVTVGCTCVTPVIHHVQ | Q96PD4 | 51 |

TABLE 1-continued

Exemplary cytokine and chemokine sequences

| Name | Sequence | UniProt ID | SEQ ID NO. |
| --- | --- | --- | --- |
| IL-23 alpha (p19) | RAVPGGSSPAWTQCQQLSQKLCTLAWSAHPLVGHM DLREEGDEETTNDVPHIQCGDGCDPQGLRDNSQFC LQRIHQGLIFYEKLLGSDIFTGEPSLLPDSPVGQL HASLLGLSQLLQPEGHHWETQQIPSLSPSQPWQRL LLRFKILRSLQAFVAVAARVFAHGAATLSP | Q9NPF7 | 52 |
| IL-3 | APMTQTTPLKTSWVNCSNMIDEIITHLKQPPLPLL DFNNLNGEDQDILMENNLRRPNLEAFNRAVKSLQN ASAIESILKNLLPCLPLATAAPTRHPIHIKDGDWN EFRRKLTFYLKTLENAQAQQTTLSLAIF | P08700 | 53 |
| IL-4 | HKCDITLQEIIKTLNSLTEQKTLCTELTVTDIFAA SKNTTEKETFCRAATVLRQFYSHHEKDTRCLGATA QQFHRHKQLIRFLKRLDRNLWGLAGLNSCPVKEAN QSTLENFLERLKTIMREKYSKCSS | P05112 | 54 |
| IL-5 | IPTEIPTSALVKETLALLSTHRTLLIANETLRIPV PVHKNHQLCTEEIFQGIGTLESQTVQGGTVERLFK NLSLIKKYIDGQKKKCGEERRRVNQFLDYLQEFLG VMNTEWIIES | P05113 | 55 |
| IL-6 | VPPGEDSKDVAAPHRQPLTSSERIDKQIRYILDGI SALRKETCNKSNMCESSKEALAENNLNLPKMAEKD GCFQSGFNEETCLVKIITGLLEFEVYLEYLQNRFE SSEEQARAVQMSTKVLIQFLQKKAKNLDAITTPDP TTNASLLTKLQAQNQWLQDMTTHLILRSFKEFLQS SLRALRQM | P05231 | 56 |
| IL-9 | QGCPTLAGILDINFLINKMQEDPASKCHCSANVTS CLCLGIPSDNCTRPCFSERLSQMTNTTMQTRYPLI FSRVKKSVEVLKNNKCPYFSCEQPCNQTTAGNALT FLKSLLEIFQKEKMRGMRGKI | P15248 | 57 |
| IL-11 | PGPPPGPPRVSPDPRAELDSTVLLTRSLLADTRQL AAQLRDKFPADGDHNLDSLPTLAMSAGALGALQLP GVLTRLRADLLSYLRHVQWLRRAGGSSLKTLEPEL GTLQARLDRLLRRLQLLMSRLALPQPPPDPPAPPL APPSSAWGGIRAAHAILGGLHLTLDWAVRGLLLLK TRL | P20809 | 58 |
| IL-13 | LTCLGGFASPGPVPPSTALRELIEELVNITQNQKA PLCNGSMVWSINLTAGMYCAALESLINVSGCSAIE KTQRMLSGFCPHKVSAGQFSSLHVRDTKIEVAQFV KDLLLHLKKLFREGRFN | P35225 | 59 |
| IL-27 alpha (p28) | FPRPPGRPQLSLQELRREFTVSLHLARKLLSEVRG QAHRFAESHLPGVNLYLLPLGEQLPDVSLTFQAWR RLSDPERLCFISTTLQPFHALLGGLGTQGRWTNME RMQLWAMRLDLRDLQRHLRFQVLAAGFNLPEEEEE EEEEEEEERKGLLPGALGSALQGPAQVSWPQLLST YRLLHSLELVLSRAVRELLLLSKAGHSVWPLGFPT LSPQP | Q8NEV9 | 60 |
| IL-27 beta (EBI3), IL-35 beta | RKGPPAALTLPRVQCRASRYPIAVDCSWTLPPAPN STSPVSFIATYRLGMAARGHSWPCLQQTPTSTSCT ITDVQLFSMAPYVLNVTAVHPWGSSSSFVPFITEH IIKPDPPEGVRLSPLAERQLQVQWEPPGSWPFPEI FSLKYWIRYKRQGAARFHRVGPIEATSFILRAVRP RARYYVQVAAQDLTDYGELSDWSLPATATMSLGK | Q14213 | 61 |
| Erythro-poietin | APPRLICDSRVLERYLLEAKEAENITTGCAEHCSL NENITVPDTKVNFYAWKRMEVGQQAVEVWQGLALL SEAVLRGQALLVNSSQPWEPLQLHVDKAVSGLRSL TTLLRALGAQKEAISPPDAASAAPLRTITADTFRK LFRVYSNFLRGKLKLYTGEACRTGDR | P01588 | 62 |
| G-CSF | ATPLGPASSLPQSFLLKCLEQVRKIQGDGAALQEK LVSECATYKLCHPEELVLLGHSLGIPWAPLSSCPS QALQLAGCLSQLHSGLFLYQGLLQALEGISPELGP TLDTLQLDVADFATTIWQQMEELGMAPALQPTQGA MPAFASAFQRRAGGVLVASHLQSFLEVSYRVLRHL AQP | P09919 | 63 |

TABLE 1-continued

Exemplary cytokine and chemokine sequences

| Name | Sequence | UniProt ID | SEQ ID NO. |
|---|---|---|---|
| Growth hormone | FPTIPLSRLFDNAMLRAHRLHQLAFDTYQEFEEAY IPKEQKYSFLQNPQTSLCFSESIPTPSNREETQQK SNLELLRISLLLIQSWLEPVQFLRSVFANSLVYGA SDSNVYDLLKDLEEGIQTLMGRLEDGSPRTGQIFK QTYSKFDTNSHNDDALLKNYGLLYCFRKDMDKVET FLRIVQCRSVEGSCGF | P01241 | 64 |
| Prolactin | LPICPGGAARCQVTLRDLFDRAVVLSHYIHNLSSE MFSEFDKRYTHGRGFITKAINSCHTSSLATPEDKE QAQQMNQKDFLSLIVSILRSWNEPLYHLVTEVRGM QEAPEAILSKAVEIEEQTKRLLEGMELIVSQVHPE TKENEIYPVWSGLPSLQMADEESRLSAYYNLLHCL RRDSHKIDNYLKLLKCRIIHNNNC | P01236 | 65 |
| Oncostatin M | AAIGSCSKEYRVLLGQLQKQTDLMQDTSRLLDPYI RIQGLDVPKLREHCRERPGAFPSEETLRGLGRRGF LQTLNATLGCVLHRLADLEQRLPKAQDLERSGLNI EDLEKLQMARPNILGLRNNIYCMAQLLDNSDTAEP TKAGRGASQPPTPTPASDAFQRKLEGCRFLHGYHR FMHSVGRVFSKWGESPNRSRRHSPHQALRKGVRRT RPSRKGKRLMTRGQLPR | P13725 | 66 |
| Leukemia inhibitory factor | SPLPITPVNATCAIRHPCHNNLMNQIRSQLAQLNG SANALFILYYTAQGEPFPNNLDKLCGPNVTDFPPF HANGTEKAKLVELYRIVVYLGTSLGNITRDQKILN PSALSLHSKLNATADILRGLLSNVLCRLCSKYHVG HVDVTYGPDTSGKDVFQKKKLGCQLLGKYKQIIAV LAQAF | P15018 | 67 |
| IL-22 | APISSHCRLDKSNFQQPYITNRTFMLAKEASLADN NTDVRLIGEKLFHGVSMSERCYLMKQVLNFTLEEV LFPQSDRFQPYMQEVVPFLARLSNRLSTCHIEGDD LHIQRNVQKLKDTVKKLGESGEIKAIGELDLLFMS LRNACI | Q9GZX6 | 68 |
| IL-10 | SPGQGTQSENSCTHFPGNLPNMLRDLRDAFSRVKT FFQMKDQLDNLLLKESLLEDFKGYLGCQALSEMIQ FYLEEVMPQAENQDPDIKAHVNSLGENLKTLRLRL RRCHRFLPCENKSKAVEQVKNAFNKLQEKGIYKAM SEFDIFINYIEAYMTMKIRN | P22301 | 69 |

In some embodiments, at least one of the first or second peptide is a cytokine or chemokine, a subunit of a cytokine or chemokine or a functional portion thereof. In some embodiments, the other of the first or second peptide is a tag or other peptide moiety.

In some embodiments, both of the first and second peptides are a cytokine or chemokine, a subunit of a cytokine or chemokine or a functional portion thereof. In some embodiments, the cytokine or chemokine is a monomer. In some embodiments, the cytokine or chemokine is homodimer or heterodimer and the first or second cytokine is a subunit of the homodimer of heterodimer. In some embodiments, the first and second peptides are the same cytokine or chemokine or functional portion thereof or are the same subunit of the same cytokine or chemokine. In some embodiments, the first and second peptides are a different cytokine or chemokine or functional portion thereof or are a different subunit of the same or different cytokine or chemokine.

In some embodiments, the cytokine or chemokine is a multimeric protein, such as is a homodimer or heterodimer, in which the first peptide is a first subunit of a cytokine or chemokine and the second peptide is a second subunit of the cytokine or chemokine. In some aspects, the joining region containing the targeting moiety connects the first and second subunits, such as the first and second subunits of a cytokine or chemokine that is a homodimer or heterodimer.

In some embodiments, the cytokine or chemokine is interleukin-12 (IL-12). Generally, IL-12 is a heterodimeric cytokine containing a p35 and a p40 subunit covalently linked by a disulfide bridge. In some embodiments, the first subunit of the IL-12 immunomodulatory polypeptide is p35 or p40 or a functional portion thereof and the second subunit is the other of p35 and p40 or a functional portion thereof. In some such cases, the joining region containing the targeting moiety connects or joins the p35 and p40 subunits of IL-12. In some aspects, the p35 subunit has the sequence set forth in SEQ ID NO: 10 or a sequence having at least 85%, 86%, 87%, 88%, 89%, 90%, 91%, 92%, 93%, 94%, 95%, 96%, 97%, 98%, 99% or more sequence identity to SEQ ID NO:10. In some aspects, the p40 subunit has the sequence set forth in SEQ ID NO: 11 or a sequence having at least 85%, 86%, 87%, 88%, 89%, 90%, 91%, 92%, 93%, 94%, 95%, 96%, 97%, 98%, 99% or more sequence identity to SEQ ID NO:11.

In some embodiments, the cytokine or chemokine is interleukin-23 (IL-23). Generally, IL-23 is a heterodimeric cytokine containing an IL-12p40 and an IL-23alpha subunit. In some embodiments, the first subunit of the IL-23 immunomodulatory polypeptide is IL-12p40 or IL-23alpha or a functional portion thereof and the second subunit is the other of IL-12p40 and IL-23alpha or a functional portion thereof. In some such cases, the joining region containing the targeting moiety connects or joins the IL-12p40 and an IL-23alpha subunit of IL-23. In some aspects, the IL-23alpha subunit has the sequence set forth in SEQ ID NO: 52 or a sequence having at least 85%, 86%, 87%, 88%, 89%, 90%, 91%, 92%, 93%, 94%, 95%, 96%, 97%, 98%, 99% or more sequence identity to SEQ ID NO:52. In some aspects, the p40 subunit has the sequence set forth in SEQ ID NO: 11 or a sequence having at least 85%, 86%, 87%, 88%, 89%, 90%, 91%, 92%, 93%, 94%, 95%, 96%, 97%, 98%, 99% or more sequence identity to SEQ ID NO:11.

In some embodiments, the cytokine or chemokine is interleukin-27 (IL-27). Generally, IL-27 is a heterodimeric cytokine containing an IL-27 alpha (p28) and an IL-27 beta (EBI3) subunit. In some embodiments, the first subunit of the IL-27 immunomodulatory polypeptide is p28 or EBI3 or a functional portion thereof and the second subunit is the other of p28 and EBI3 or a functional portion thereof. In some such cases, the joining region containing the targeting moiety connects or joins the p28 and EBI3 subunits of IL-27. In some aspects, the p28 subunit has the sequence set forth in SEQ ID NO: 60 or a sequence having at least 85%, 86%, 87%, 88%, 89%, 90%, 91%, 92%, 93%, 94%, 95%, 96%, 97%, 98%, 99% or more sequence identity to SEQ ID NO:60. In some aspects, the EBI3 subunit has the sequence set forth in SEQ ID NO: 61 or a sequence having at least 85%, 86%, 87%, 88%, 89%, 90%, 91%, 92%, 93%, 94%, 95%, 96%, 97%, 98%, 99% or more sequence identity to SEQ ID NO:61.

In some embodiments, the cytokine or chemokine is interleukin-35 (IL-35). Generally, IL-35 is a heterodimeric cytokine containing an IL-12p35 and an IL-27 beta (EBI3) subunit covalently linked by a disulfide bridge. In some embodiments, the first subunit of the IL-35 immunomodulatory polypeptide is p35 or EBI3 or a functional portion thereof and the second subunit is the other of p35 and EBI3 or a functional portion thereof. In some such cases, the joining region containing the targeting moiety connects or joins the p35 and EBI3 subunits of IL-35. In some aspects, the p35 subunit has the sequence set forth in SEQ ID NO: 10 or a sequence having at least 85%, 86%, 87%, 88%, 89%, 90%, 91%, 92%, 93%, 94%, 95%, 96%, 97%, 98%, 99% or more sequence identity to SEQ ID NO:10. In some aspects, the EBI3 subunit has the sequence set forth in SEQ ID NO: 61 or a sequence having at least 85%, 86%, 87%, 88%, 89%, 90%, 91%, 92%, 93%, 94%, 95%, 96%, 97%, 98%, 99% or more sequence identity to SEQ ID NO:61.

In some embodiments, the cytokine or chemokine is or comprises interleukin-15 (IL-15). Generally, IL-15 is a cytokine and may be soluble or membrane-bound. In some embodiments, IL-15 is monomeric and in other embodiments, IL-15 is heterodimeric. In some embodiments, IL-15 is associated with IL-15Rα. In some embodiments, the first subunit of the IL-15 immunomodulatory polypeptide is IL-15 or IL-15Rα or a functional portion thereof and the second subunit is the other of IL-15 or IL-15Rα or a functional portion thereof. In some such cases, the joining region containing the targeting moiety connects or joins the IL-15 or IL-15Rα peptides.

B. Joining Region

In some embodiments, the immunomodulatory polypeptide contains a joining region that connects the first and second peptides, such as the first and second cytokine or chemokine or the first and second subunit of the cytokine or chemokine or functional portions thereof. In some aspects, the joining region contains a targeting moiety, such as a targeting peptide, that binds to a target molecule. In some embodiments, the targeting moiety is directly connected to at least one of the first and second peptides and, in some cases, both of the first and second peptides. In some embodiments, the targeting moiety is indirectly connected to at least one of the first and second peptides and, in some cases, both of the first and second peptides, such as indirectly connective via a linker. In some cases, the joining region further contains one or more polypeptide linkers connecting the targeting moiety to one or both of the first and second peptide. In some aspects, the targeting moiety is flanked by two polypeptide linkers connecting the first and second peptides.

In some aspects, the immunomodulatory protein comprises: a first peptide, a targeting moiety and a second peptide. In some aspects, the immunomodulatory protein comprises: a first peptide, a linker, a targeting moiety, and a second peptide. In some aspects, the immunomodulatory protein comprises: a first peptide, a targeting moiety, a linker, and a second peptide. In some aspects, the immunomodulatory protein comprises: a first peptide, a linker, a targeting moiety, a linker and a second peptide. In any of such embodiments, the first and second peptide can be reversed in position.

In some embodiments, the joining region does not exceed a maximum length. In some instances, the maximum length of the joining region is or is about no more than 400, 300, 250, 200, 150, 100, 50, 40, 30, 25, 20, 15, 10, or 5 amino acids. In some embodiments, the length of the joining region exceeds 400 amino acids. In some aspects, the length of the joining region, such as including the targeting moiety and optionally one or two linkers, is between or between about 5 and 400 amino acids, such as between or between about 10 and 400 amino acids, 10 and 300 amino acids, 10 and 200 amino acids, 10 and 100 amino acids, 10 and 50 amino acids, 10 and 30 amino acids, 10 and 20 amino acids, 20 and 400 amino acids, 20 and 300 amino acids, 20 and 200 amino acids, 20 and 100 amino acids, 20 and 50 amino acids, 20 and 30 amino acids, 30 and 400 amino acids, 30 and 300 amino acids, 30 and 200 amino acids, 30 and 100 amino acids, 30 and 50 amino acids, 50 and 400 amino acids, 50 and 300 amino acids, 50 and 200 amino acids, 50 and 100 amino acids, 100 and 400 amino acids, 100 and 300 amino acids, 100 and 200 amino acids, 200 and 400 amino acids or 200 and 300 amino acids. In some embodiments, the length of the joining region is between or between about 5 and 50 amino acids, such as 5 and 40 amino acids, 5 and 30 amino acids, 5 and 20 amino acids, 5 and 10 amino acids, 10 and 50 amino acids, 10 and 40 amino acids, 10 and 30 amino acids, 10 and 20 amino acids, 20 and 50 amino acids, 20 and 40 amino acids, 20 and 30 amino acids, 30 and 50 amino acids, 30 and 40 amino acids or 40 and 50 amino acids.

1. Targeting Moiety

In some aspects, the joining region contains a targeting moiety, such as a targeting peptide that binds to a target molecule on the surface of a cell. In some cases, the joining region contains two or more targeting moieties. In some such cases, the two or more targeting moieties may be the same or different. In some cases, the targeting moiety is human or is derived from a human protein. In some embodiments, the targeting moiety is a binding peptide. In some embodiments, the targeting moiety is an antibody or antigen-binding fragment thereof.

In some embodiments, the targeting moiety binds to a target molecule that is a protein, glycoprotein or lipid. In some embodiments, the target molecule is associated with a disease or disorder. In some aspects, the disease or disorder is an infectious disease or disorder, an autoimmune disease, an inflammatory disease, or a tumor or a cancer. In some cases, the target molecule is associated with a tumor or present on a tumor. In some aspects, the target molecule is a tumor antigen. In some embodiments, the target molecule is expressed on the surface of a cell, such as a tumor cell.

In some embodiments, the target molecule is selected from among: hepatocyte growth factor (HGF), heparin, VEGF, VEGF-A, VEGFR2, VEGFR3, HER2, PD-1, tenascin-C, CTLA-4, LAGS, PD-L1, EGFR, EPCAM, RANKL, NG2 proteoglycan, CD20, CD52, CD19, CD3, CD30, IL-6, CD38, SLAMF7, GD2, CD13, CD274, CD279, CD40L, and CD47.

In some aspects, the targeting moiety has a length of no more than 400, 300, 250, 200, 150, 100, 50, 40, 30, 25, 20, 15, 10, or 5 amino acids. In some aspects, the length of the targeting moiety is between or between about 5 and 400 amino acids, such as between or between about 10 and 400 amino acids, 10 and 300 amino acids, 10 and 200 amino acids, 10 and 100 amino acids, 10 and 50 amino acids, 10 and 30 amino acids, 10 and 20 amino acids, 20 and 400 amino acids, 20 and 300 amino acids, 20 and 200 amino acids, 20 and 100 amino acids, 20 and 50 amino acids, 20 and 30 amino acids, 30 and 400 amino acids, 30 and 300 amino acids, 30 and 200 amino acids, 30 and 100 amino acids, 30 and 50 amino acids, 50 and 400 amino acids, 50 and 300 amino acids, 50 and 200 amino acids, 50 and 100 amino acids, 100 and 400 amino acids, 100 and 300 amino acids, 100 and 200 amino acids, 200 and 400 amino acids or 200 and 300 amino acids. In some embodiments, the length of the joining region is between or between about 5 and 50 amino acids, such as 5 and 40 amino acids, 5 and 30 amino acids, 5 and 20 amino acids, 5 and 10 amino acids, 10 and 50 amino acids, 10 and 40 amino acids, 10 and 30 amino acids, 10 and 20 amino acids, 20 and 50 amino acids, 20 and 40 amino acids, 20 and 30 amino acids, 30 and 50 amino acids, 30 and 40 amino acids or 40 and 50 amino acids.

In some embodiments, the targeting moiety binds the target molecule with at least a certain affinity, as measured by any of a number of known methods. In some embodiments, the affinity is represented by a dissociation constant ($K_D$) or an association constant ($K_A$). In some embodiments, the affinity is represented by EC50. In some embodiments, the targeting moiety binds, such as specifically binds, to the target molecule with an affinity or $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$.

In some embodiments, the targeting moiety exhibits a binding affinity for the target molecule with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from or from about $10^{-5}$ M to or to about $10^{-15}$ M, such as from or from about $10^{-6}$ M to or to about $10^{-12}$ M, from or from about $10^{-7}$ M to or to about $10^{-11}$ M, from or from about $10^{-6}$ M to or to about $10^{-8}$ M, or from or from about $10^{-7}$ M to or to about $10^{-8}$ M. In some embodiments, the $K_D$ of the targeting moiety to the target molecule is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, 1 nM, such as between at or about 1 nM and at or about 15 nM, e.g., between at or about 5 and at or about 10 nM. In some embodiments, the $K_D$ of the targeting moiety to the target molecule is at or about or less than at or about 1 nM, 100 picomolar (pM), 90 pM, 80 pM, 70 pM, 60 pM, 50 pM, 40 pM, 30 pM, 25 pM, 20 pM, 15 pM, 10 pM, or 1 pM, such as between at or about 10 pM and at or about 100 pM, e.g., between at or about 25 pM and at or about 75 pM.

The on-rate (association rate constant; $k_{on}$ or $k_a$; units of 1/M·sec or $M^{-1}$ $sec^{-1}$) and the off-rate (dissociation rate constant; $k_{off}$ or $k_d$; units of 1/s or $sec^{-1}$) can be determined using any of the assay methods known in the art, for example, surface plasmon resonance (SPR, e.g., using a Biacore instrument). In some embodiments, the targeting moiety binds the target molecule with a higher affinity that the cytokine or chemokine binds its receptor.

In some embodiments, the targeting moiety exhibits a $k_{off}$ rate for binding the target molecule that is about $0.5 \times 10^{-4}$ $sec^{-1}$ or less, about $1 \times 10^{-4}$ $sec^{-1}$ or less, about $2 \times 10^{-4}$ $sec^{-1}$ or less, about $3 \times 10^{-4}$ $sec^{-1}$ or less, about $4 \times 10^{-4}$ $sec^{-1}$ or less, about $5 \times 10^{-4}$ $sec^{-1}$ or less, about $1 \times 10^{-3}$ $sec^{-1}$ or less, about $1.5 \times 10^{-3}$ $sec^{-1}$ or less, about $2 \times 10^{-3}$ $sec^{-1}$ or less, about $3 \times 10^{-3}$ $sec^{-1}$ or less, about $4 \times 10^{-3}$ $sec^{-1}$ or less, about $5 \times 10^{-3}$ $sec^{-1}$ or less, about $1 \times 10^{-2}$ sec or less, or about $5 \times 10^{-1}$ $sec^{-1}$ or less.

In some embodiments, the targeting moiety is or contains a peptide binding motif. In some aspects, the targeting moiety is or is derived from a hepatocyte growth factor (HGF) binding peptide (HGFBP), a heparin binding peptide (HBP) (e.g., BMP4 or fibronectin), a VEGF binding peptide, a VEGF-A binding peptide, a VEGFR (e.g. VEGFR2 or VEGFR3) binding peptide, an EPCAM binding peptide, a HER2 binding peptide, a PD-1 binding peptide, a tenascin-C binding peptide, a CTLA-4 binding peptide, a LAGS binding peptide, a PD-L1 binding peptide, an EGFR binding peptide, a RANKL binding peptide, a CD20 binding peptide, a CD52 binding peptide, a CD19 binding peptide, a CD3 binding peptide, a CD30 binding peptide, a IL-6 binding peptide, a CD38 binding peptide, a SLAMF7 binding peptide, a GD2 binding peptide, a CD274 binding peptide, a CD279 binding peptide, a CD40L binding peptide, a CD47 binding peptide, a CD13 binding peptide, an NGR motif, an RGD motif, or an NG2 proteoglycan binding peptide. In some cases, the targeting moiety is or contains an HGF binding peptide (HGFBP), an HBP or an EGFR binding peptide (EGFRBP). In some instances, the heparin binding peptide (HBP) is derived from fibronectin or BMP4, and/or is of bovine origin. Examples of such binding peptides are known, see e.g. Tam et al. (2009) Journal of Molecular Biology, 385:79-90; Ahsan et al. (2014) Neoplasia, 16:105-14; Binetruy-Tournaire et al. (2000) EMBO J., 19:1525-1533; Vicari et al. (2011) J. Biol. Chem., 286:13612-25; Andersson et al. (2004) FEBS J., 271: 1219-1226; Abcam Cat. No. ab152112 (Cambridge, MA); Chen et al. (2015) BioMed Research International, Article ID 237969; U.S. Pat. No. 8,188,220. Targeting moieties also can be peptides that are identified in binding assays as peptides that bind a selected target molecule.

Table 2 provides non-limiting examples of peptide binding motifs that can be a targeting moiety. In some embodiments, the targeting moiety is or comprises a sequence of amino acids set forth in any of SEQ ID NOS: 13-16 and 27-28 or a sequence of amino acids that exhibits at least 85%, 86%, 87%, 88%, 89%, 89%, 91%, 92%, 93%, 94%, 95%, 96%, 97%, 98%, 99% or more sequence identity to any of SEQ ID NOS: 13-16 and 27-28.

TABLE 2

Peptide Binding Targeting Moiety

| Name | Sequence | SEQ ID NO. |
|---|---|---|
| Heparin binding peptide, BMP4 | RKKNPNCRRH | 13 |
| Heparin binding peptide, fibronectin | KNNQKSEPLIGRKKT | 14 |
| HGF binding peptide | VWNWVCFRDVGCDWVL | 15 |
| EGFR binding peptide (EGFRBP) | SVDNPHVC | 16 |
| EGFR binding peptide | YHWYGYTPQNVI | 108 |
| EGFR binding peptide | YRWYGYTPQNVI | 109 |
| VEGF binding peptide | ATWLPPR | 26 |
| VEGFR binding peptide | ITMQCGIHQGQHPKIRMICEMSF | 27 |
| VEGFR binding peptide | ITMQIMRIKPHQGQHIGEMSF | 118 |
| VEGFR3 binding peptide | PCAIWF | 110 |
| VEGFR3 binding peptide | WVCSGG | 111 |
| bovine origin heparin binding peptide | WQPPRARI | 28 |
| NGR motif (e.g., CD13 binding peptide; angiogenesis targeting peptide | NGRNGRNGR | 112 |
| RGD motif | RGDRGDRGD | 113 |
| NG2 proteoglycan binding peptide | TAASGVRSMH | 114 |
| NG2 proteoglycan binding peptide | LTLRWVGLMS | 115 |
| HER2 binding peptide | NKFNKGMRYWGALGGNGKRGIRGYM | 116 |
| EPCAM binding peptide | YEVHTYYLD | 117 |

In some aspects, the targeting moiety is or comprises an antibody or antibody fragment. Among the antibodies are human antibodies, including any known to bind a targeting molecule as described.

The term "antibody" herein is used in the broadest sense and includes polyclonal and monoclonal antibodies, including intact antibodies and functional (antigen-binding) antibody fragments, including fragment antigen binding (Fab) fragments, F(ab')₂ fragments, Fab' fragments, Fv fragments, recombinant IgG (rIgG) fragments, variable heavy chain (V$_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂; diabodies; linear antibodies; variable heavy chain (V$_H$) regions, single-chain antibody molecules such as scFvs and single-domain V$_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain", when used in reference to an antibody, such as an antibody fragment, refers to the domain of an antibody heavy or light chain that is involved in binding the antibody to antigen. The variable domains of the heavy chain and light chain (V$_H$ and V$_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single V$_H$ or V$_L$ domain may be sufficient to confer antigen-binding specificity. Furthermore, antibodies that bind a particular antigen may be isolated using a V$_H$ or V$_L$ domain from an antibody that binds the antigen to screen a library of complementary V$_L$ or V$_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

In some such aspects, the targeting moiety is or comprises an antibody fragment that is a single chain fragment. In some instances, the antibody fragment comprises antibody variable regions joined by a flexible linker, such as a linker set forth in SEQ ID NO:9, SEQ ID NO:22 or SEQ ID NO:23. In some examples, the antibody fragment is or contains an scFv. Thus, in some instances, the targeting moiety contains a variable heavy (VH) chain and a variable light (VL) chain. In some embodiments, the targeting moiety is or contains a VH chain, but does not contain a VL chain. In some such aspects, the targeting moiety is or contains a high-affinity, e.g., super high-affinity, VH chain. In some embodiments, the targeting moiety is or contains a variable heavy (VH) chain and/or variable light (VL) chain of an antibody.

In some embodiments, the antibody is an anti-hepatocyte growth factor (HGF) antibody, an anti-heparin antibody, and anti-VEGF antibody, and anti-VEGF-A antibody, an anti-VEGFR antibody, an anti-VEGFR2 antibody, an anti-HER2 antibody, an anti-PD-1 antibody, an anti-tenascin-C antibody, an anti-CTLA-4, an anti-LAG3 antibody, an anti-PD-L1 antibody, an anti-EGFR antibody, an anti-EPCAM antibody, an anti-RANKL antibody, and anti-CD20 antibody, an anti-CD52 antibody, an anti-CD19 antibody, an anti-CD3 antibody, an anti-CD30 antibody, an anti-IL-6 antibody, an anti-CD38 antibody, an anti-SLAMF7 antibody, an anti-GD2 antibody, an anti-CD274 antibody, an anti-CD279 antibody, an anti-CD40L antibody, and an anti-CD47-antibody or antigen-binding fragments thereof.

In some such cases, the antibody is or is derived from a VH and/or a VL chain of trastuzumab, pertuzumab, ramucirumab, atezolizumab, bevacizumab, panitumumab, cetuximab, necitumumab, denosumab, nivolumab, pembrolizumab, rituximab, ofatumumab, obinutuzumab, alemtuzumab, blinatumomab, brentuximab vedotin, siltuximab, ipilimumab, daratumumab, elotuzumab, dinutuximab, or catumaxomab or antigen-binding fragments thereof.

In some instances, the targeting moiety is or contains an anti-EPCAM antibody. In some embodiments, the targeting moiety has the sequence set forth in SEQ ID NO: 17, or a sequence that has at least 85%, 86%, 87%, 88%, 89%, 90%, 91%, 92%, 93%, 94%, 95%, 96%, 97%, 98%, 99%, or more sequence identity to such a sequence and binds to the target molecule.

2. Polypeptide Linker

In some embodiments, the joining region further contains at least one polypeptide linker linking the targeting moiety to the first or second peptide, such as the first or second subunit of the cytokine or chemokine. In some cases, the joining region contains two polypeptide linkers. In some such cases, one of the polypeptide linkers links the first peptide, such as the first subunit of the cytokine or chemokine, to the targeting moiety and the other polypeptide linker links the second peptide, such as the second subunit of the cytokine or chemokine, to the targeting moiety. Thus, in some cases, the targeting moiety is contained between a first and a second polypeptide linker, which together form the joining region.

In some embodiments, the polypeptide linker contains from about 2 to about 20 amino acids, such as about 5 to about 15 amino acids, such as 15 or about 15 amino acids. In some cases, the polypeptide linker has the sequence GGGGS(n), wherein n is greater than or equal to one. For example, in some instances, where n=1, the polypeptide linker has the sequence set forth in SEQ ID NO: 7. In some cases, where n=2, the polypeptide linker has the sequence set forth in SEQ ID NO: 8. In some aspects, where n=3, the polypeptide linker has the sequence set forth in SEQ ID NO: 9.

C. Exemplary Immunomodulatory Polypeptides

In some aspects, the immunomodulatory polypeptide is or contains an IL-12 polypeptide. In some embodiments, the immunomodulatory polypeptide contains a p35 subunit of IL-12, a p40 subunit of IL-12, and a joining region connecting the p35 and p40 subunits. In some such embodiments, the joining region contains a targeting moiety that binds to a target molecule.

In some instances, the joining region further contains at least one polypeptide linker linking the targeting moiety to the p35 subunit or the p40 subunit. For example, in some aspects, the p40 subunit is connected to a first polypeptide linker that is also attached to a first end of the targeting moiety, and the second end of the targeting moiety is connected to a second polypeptide linker that is also attached to one end of the p35 subunit.

In some embodiments, the IL-12 immunomodulatory polypeptide exhibits increased activity to stimulate via the IL-12R compared to a recombinant IL-12 not comprising the joining region. In some aspects, the immunomodulatory polypeptide exhibits increased binding to a target cell expressing the target molecule as compared with its binding to a cell not expressing the target molecule. In some embodiments, the IL-12 immunomodulatory polypeptides or cells containing such a peptide exhibit increased or decreased activity to stimulate via the IL-12R compared to a recombinant IL-12 not containing the joining region.

In some embodiments, the IL-12 immunomodulatory polypeptide exhibits an increased binding affinity for the IL-12R. In some embodiments, the IL-12 immunomodulatory polypeptide exhibits a decreased binding affinity for the IL-12R. In some examples, the equilibrium dissociation constant $K_D$ of the IL-12 immunomodulatory polypeptide and the IL-12R is from or from about $10^{-5}$ M to or to about $10^{-15}$ M, such as from or from about $10^{-6}$ M to or to about $10^{-12}$ M, from or from about $10^{-7}$ M to or to about $10^{-11}$ M, from or from about $10^{-6}$ M to or to about $10^{-8}$ M, or from or from about $10^{-7}$ M to or to about $10^{-8}$ M. In some embodiments, the $K_D$ of the IL-12 immunomodulatory polypeptide and the IL-12R is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, 1 nM, such as between at or about 1 nM and at or about 15 nM, e.g., between at or about 5 and at or about 10 nM. In some embodiments, the $K_D$ of the IL-12 immunomodulatory polypeptide and the IL-12R is at or about or less than at or about 1 nM, 100 picomolar (pM), 90 pM, 80 pM, 70 pM, 60 pM, 50 pM, 40 pM, 30 pM, 25 pM, 20 pM, 15 pM, 10 pM, or 1 pM, such as between at or about 10 pM and at or about 100 pM, e.g., between at or about 25 pM and at or about 75 pM.

In some aspects, the increased activity and/or binding is greater than effected by a reference immunomodulatory polypeptide containing a polypeptide linker between subunits but not containing the targeting moiety. In some such aspects, the increase is by greater than 1.2-fold, greater than 1.5-fold, greater than 2.0-fold, greater than 3.0-fold, greater than 4.0-fold, greater than 5.0-fold or greater than 10.0-fold.

In some embodiments, the immunomodulatory protein contains: a p35 subunit that has the sequence of amino acids set forth in SEQ ID NO: 10 or a sequence that has at least 85%, 86%, 87%, 88%, 89%, 90%, 91%, 92%, 93%, 94%, 95%, 96%, 97%, 98%, 99% sequence identity to SEQ ID NO:10; a joining region comprising a targeting moiety set forth in SEQ ID NO:13 (HBP BMP4); and a p40 subunit that has the sequence of amino acids set forth in SEQ ID NO: 11 or a sequence that has at least 85%, 86%, 87%, 88%, 89%, 90%, 91%, 92%, 93%, 94%, 95%, 96%, 97%, 98%, 99% sequence identity to SEQ ID NO:11. The components can be in the order as specified or the reverse order. In some embodiments, the joining region contains the targeting moiety flanked on either side by a linker each independently set forth in SEQ ID NO:29, such as set forth in SEQ ID NO:7. In some embodiments, the immunomodulatory protein comprises the sequence of amino acids set forth in SEQ ID NO:2 or a sequence of amino acids that has at least 85%, 86%, 87%, 88%, 89%, 90%, 91%, 92%, 93%, 94%, 95%, 96%, 97%, 98%, 99% sequence identity to SEQ ID NO:2.

In some embodiments, the immunomodulatory protein contains: a p35 subunit that has the sequence of amino acids set forth in SEQ ID NO: 10 or a sequence that has at least 85%, 86%, 87%, 88%, 89%, 90%, 91%, 92%, 93%, 94%, 95%, 96%, 97%, 98%, 99% sequence identity to SEQ ID NO:10; a joining region comprising a targeting moiety set forth in SEQ ID NO:14 (HBP FBN); and a p40 subunit that has the sequence of amino acids set forth in SEQ ID NO: 11 or a sequence that has at least 85%, 86%, 87%, 88%, 89%, 90%, 91%, 92%, 93%, 94%, 95%, 96%, 97%, 98%, 99% sequence identity to SEQ ID NO:11. The components can be in the order as specified or the reverse order. In some embodiments, the joining region contains the targeting moiety flanked on either side by a linker each independently set forth in SEQ ID NO:29, such as set forth in SEQ ID NO:7. In some embodiments, the immunomodulatory protein comprises the sequence of amino acids set forth in SEQ ID NO:3 or a sequence of amino acids that has at least 85%, 86%, 87%, 88%, 89%, 90%, 91%, 92%, 93%, 94%, 95%, 96%, 97%, 98%, 99% sequence identity to SEQ ID NO:3.

In some embodiments, the immunomodulatory protein contains: a p35 subunit that has the sequence of amino acids set forth in SEQ ID NO: 10 or a sequence that has at least 85%, 86%, 87%, 88%, 89%, 90%, 91%, 92%, 93%, 94%, 95%, 96%, 97%, 98%, 99% sequence identity to SEQ ID NO:10; a joining region comprising a targeting moiety set forth in SEQ ID NO:15 (HGF binding peptide); and a p40 subunit that has the sequence of amino acids set forth in SEQ ID NO: 11 or a sequence that has at least 85%, 86%, 87%, 88%, 89%, 90%, 91%, 92%, 93%, 94%, 95%, 96%, 97%, 98%, 99% sequence identity to SEQ ID NO:11. The components can be in the order as specified or the reverse order. In some embodiments, the joining region contains the targeting moiety flanked on either side by a linker each independently set forth in SEQ ID NO:29, such as set forth in SEQ ID NO:7. In some embodiments, the immunomodulatory protein comprises the sequence of amino acids set forth in SEQ ID NO:4 or a sequence of amino acids that has at least 85%, 86%, 87%, 88%, 89%, 90%, 91%, 92%, 93%, 94%, 95%, 96%, 97%, 98%, 99% sequence identity to SEQ ID NO:4.

In some embodiments, the immunomodulatory protein contains: a p35 subunit that has the sequence of amino acids set forth in SEQ ID NO: 10 or a sequence that has at least 85%, 86%, 87%, 88%, 89%, 90%, 91%, 92%, 93%, 94%, 95%, 96%, 97%, 98%, 99% sequence identity to SEQ ID NO:10; a joining region comprising a targeting moiety set forth in SEQ ID NO:16 (EGFRBP); and a p40 subunit that has the sequence of amino acids set forth in SEQ ID NO: 11 or a sequence that has at least 85%, 86%, 87%, 88%, 89%, 90%, 91%, 92%, 93%, 94%, 95%, 96%, 97%, 98%, 99% sequence identity to SEQ ID NO:11. The components can be in the order as specified or the reverse order. In some embodiments, the joining region contains the targeting moiety flanked on either side by a linker each independently set forth in SEQ ID NO:29, such as set forth in SEQ ID NO:7. In some embodiments, the immunomodulatory protein comprises the sequence of amino acids set forth in SEQ ID NO:5 or a sequence of amino acids that has at least 85%, 86%, 87%, 88%, 89%, 90%, 91%, 92%, 93%, 94%, 95%, 96%, 97%, 98%, 99% sequence identity to SEQ ID NO:5.

In some embodiments, the immunomodulatory protein contains: a p35 subunit that has the sequence of amino acids set forth in SEQ ID NO: 10 or a sequence that has at least 85%, 86%, 87%, 88%, 89%, 90%, 91%, 92%, 93%, 94%, 95%, 96%, 97%, 98%, 99% sequence identity to SEQ ID NO:10; a joining region comprising a targeting moiety that is an anti-EPCAM antibody comprising the VH chain set forth in SEQ ID NO:25 and/or the VL chain set forth in SEQ ID NO: 24, such as an scFv set forth in SEQ ID NO:17 or a sequence of amino acids that exhibits at least 85%, 86%, 87%, 88%, 89%, 90%, 91%, 92%, 93%, 94%, 95%, 96%, 97%, 98%, 99% sequence identity to any of SEQ ID NOS: 17, 24 and 25; and a p40 subunit that has the sequence of amino acids set forth in SEQ ID NO: 11 or a sequence that has at least 85%, 86%, 87%, 88%, 89%, 90%, 91%, 92%, 93%, 94%, 95%, 96%, 97%, 98%, 99% sequence identity to SEQ ID NO:11. The components can be in the order as specified or the reverse order. In some embodiments, the joining region contains the targeting moiety flanked on either side by a linker each independently set forth in SEQ ID NO:29, such as set forth in SEQ ID NO:7. In some embodiments, the immunomodulatory protein comprises the sequence of amino acids set forth in SEQ ID NO:6 or a sequence of amino acids that has at least 85%, 86%, 87%, 88%, 89%, 90%, 91%, 92%, 93%, 94%, 95%, 96%, 97%, 98%, 99% sequence identity to SEQ ID NO:6.

II. Recombinant Receptors

In some embodiments, the immunomodulatory polypeptides are used in combination with and/or are expressed in or from engineered cells expressing recombinant receptors.

Thus, provided are engineered or recombinant receptors and cells expressing such receptors. In some embodiments, the engineered or recombinant receptors include chimeric receptors, including those containing ligand-binding domains or binding fragments thereof, such as functional non-TCR antigen receptors, such as chimeric antigen receptors (CARs), and also include T cell receptors (TCRs), such as transgenic TCRs, and components thereof. The chimeric receptor, such as a CAR, generally includes the extracellular antigen (or ligand) binding domain linked to one or more intracellular signaling components, in some aspects via linkers and/or transmembrane domain(s).

In particular embodiments, the recombinant receptor, such as chimeric receptor, contains an intracellular signaling domain, which includes an activating cytoplasmic signaling domain (also interchangeably called an intracellular signaling region), such as an activating cytoplasmic (intracellular) domain capable of inducing a primary activation signal in a T cell, for example, a cytoplasmic signaling domain of a T cell receptor (TCR) component (e.g. a cytoplasmic signaling domain of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.*, 2012 October; 24(5): 633-39; Wu et al., *Cancer*, 2012 Mar. 18(2): 160-75. In some embodiments, the genetically engineered antigen receptors include a CAR as described in U.S. Pat. No. 7,446,190, and those described in International Patent Application Publication No.: WO/2014055668 A1. In some embodiments, similar methods for the construction and introduction or transfer into immune cells can be employed for the provided chimeric receptors.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the antigen (or a ligand) is a tumor antigen or cancer marker.

In certain embodiments, the antigen is αvβ6 integrin (avb6 integrin), B cell maturation antigen (BCMA), B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C-C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, fetal acetylcholine receptor, ganglioside GD2, O-acetylated GD2 (OGD2), ganglioside GD3, glycoprotein 100 (gp100), Her2/neu (receptor tyrosine kinase erbB2), Her3 (erb-B3), Her4 (erb-B4), erbB dimers, Human high molecular weight-melanoma-associated antigen (HMW-MAA), hepatitis B surface antigen, Human leukocyte antigen A1 (HLA-AI), Human leukocyte antigen A2 (HLA-A2), IL-22 receptor alpha(IL-22Ra), IL-13 receptor alpha 2 (IL-13Ra2), kinase insert domain receptor (kdr), kappa light chain, L1 cell adhesion molecule (L1CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen is a pathogen-specific antigen. In some embodiments, the antigen is a viral antigen (such as a viral antigen from HIV, HCV, HBV, etc.), bacterial antigens, and/or parasitic antigens.

A. Ligand Binding Domain

In some embodiments, the recombinant receptor, e.g. antigen receptor, contains a ligand-binding domain, such as an antigen-binding domain. In some embodiments, the recombinant receptor is a chimeric antigen receptor (CAR).

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

In some embodiments, the CAR contains an antibody or an antigen-binding fragment (e.g. scFv) that specifically recognizes an antigen, such as an intact antigen, expressed on the surface of a cell.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally CD8$^+$ T cells, but in some cases CD4+ T cells. In some embodiments, MHC class II molecules deliver peptides originating in the vesicular system to the cell surface, where they are typically recognized by CD4$^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFV or other antibody forms can be generated, for example, in which members of the library are mutated at one or more residues of a CDR or CDRs. Exemplary of such methods are known in the art (see e.g. US published application No. US20020150914, US2014/0294841; and Cohen C J. et al. (2003) *J Mol. Recogn.* 16:324-332).

1. T cell Receptors (TCRs)

In some embodiments, the recombinant receptors include recombinant T cell receptors (TCRs) and/or TCRs cloned from naturally occurring T cells.

In some embodiments, a T cell receptor (TCR) contains a variable α and β chains (also known as TCRα and TCRβ, respectively) or a variable γ and δ chains (also known as TCRγ and TCRδ, respectively), or a functional fragment thereof such that the molecule is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al., *Immunobiology: The Immune System in Health and Disease*, 3$^{rd}$ Ed., Current Biology Publications, p. 4:33, 1997). For example, in some embodiments, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

Unless otherwise stated, the term "TCR" should be understood to encompass functional TCR fragments thereof. The term also encompasses intact or full-length TCRs, including TCRs in the αβ form or γδ form. Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., *Proc. Nat'l Acad. Sci. U.S.A.* 87:9138, 1990; Chothia et al., EMBO J. 7:3745, 1988; see also Lefranc et al., *Dev. Comp. Immunol.* 27:55, 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_\alpha$ or $V_\beta$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_\alpha$, typically amino acids 117 to 259 based on Kabat, β-chain constant domain or $C_\beta$, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chain contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354. In some embodiments, the TCR or antigen-binding portion thereof can be synthetically generated from knowledge of the sequence of the TCR.

In some embodiments, after the T-cell clone is obtained, the TCR alpha and beta chains are isolated and cloned into a gene expression vector. In some embodiments, the TCR alpha and beta genes are linked via a picornavirus 2A ribosomal skip peptide so that both chains are coexpressed. In some embodiments, genetic transfer of the TCR is accomplished via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy: The Journal of the American Society of Gene Therapy. 18:1748-1757; an Hackett et al. (2010) Molecular Therapy: The Journal of the American Society of Gene Therapy. 18:674-683.

B. Transmembrane and Intracellular Domains

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the spacer has the sequence set forth in SEQ ID NO: 70, and is encoded by the sequence set forth in SEQ ID NO: 71. In some embodiments, the spacer has the sequence set forth in SEQ ID NO: 72. In some embodiments, the spacer has the sequence set forth in SEQ ID NO: 73.

In some embodiments, the constant region or portion is of IgD. In some embodiments, the spacer has the sequence set forth in SEQ ID NO:74. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 70, 72, 73 and 74.

The antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the CAR is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3-ζ) or Fc receptor γ and CD8, CD4, CD25 or CD16.

In some embodiments, upon ligation of the CAR, the cytoplasmic domain or intracellular signaling domain of the CAR activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668).

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor may further include a marker or the cell may further express a marker, such as a surrogate marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 75 or 101 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 75 or 101. An exemplary T2A linker sequence comprises the sequence of amino acids set forth in SEQ ID NO: 76 or 96 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 76 or 96.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 77 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:77; in some embodiments, the transmembrane-domain containing portion of the recombinant receptor comprises the sequence of amino acids set forth in SEQ ID NO: 78 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 79 or 80 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 79 or 80. In some embodiments, the intracellular domain comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 81 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 81.

In some embodiments, the intracellular signaling domain comprises a human CD3 zeta stimulatory signaling domain or functional variant thereof, such as a 112 AA cytoplasmic domain of isoform 3 of human CD3ζ (Accession No.: P20963.2) or a CD3 zeta signaling domain as described in U.S. Pat. No. 7,446,190 or 8,911,993. In some embodiments, the intracellular signaling domain comprises the sequence of amino acids set forth in SEQ ID NO: 82, 83 or 84 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 82, 83 or 84.

In some aspects, the spacer contains only a hinge region of an IgG, such as only a hinge of IgG4 or IgG1, such as the hinge only spacer set forth in SEQ ID NO:70. In other embodiments, the spacer is an Ig hinge, e.g., and IgG4 hinge, linked to a CH2 and/or CH3 domains. In some embodiments, the spacer is an Ig hinge, e.g., an IgG4 hinge, linked to CH2 and CH3 domains, such as set forth in SEQ ID NO:73. In some embodiments, the spacer is an Ig hinge, e.g., an IgG4 hinge, linked to a CH3 domain only, such as set forth in SEQ ID NO:72. In some embodiments, the spacer is or comprises a glycine-serine rich sequence or other flexible linker such as known flexible linkers.

For example, in some embodiments, the CAR includes an antigen-binding domain, e.g. scFvs, a spacer such as any of the Ig-hinge containing spacers, a CD28 transmembrane domain, a CD28 intracellular signaling domain, and a CD3 zeta signaling domain. In some embodiments, the CAR includes the antigen-binding domain, e.g. scFv, a spacer such as any of the Ig-hinge containing spacers, a CD28 transmembrane domain, a CD28 intracellular signaling domain, and a CD3 zeta signaling domain. In some embodiments, such CAR constructs further includes a T2A ribosomal skip element and/or a tEGFR sequence, e.g., downstream of the CAR.

III. Nucleic Acids, Vectors, and Engineered Cells

Also provided are polynucleotides (nucleic acid molecules) encoding the immunomodulatory peptides and recombinant receptors, vectors for genetically engineering cells to express such polypeptides and receptors, and methods for producing the immunomodulatory polypeptides, recombinant receptors, and genetically engineered cells.

A. Polynucleotides

In some embodiments, provided are polynucleotides that encode any of the immunomodulatory polypeptides provided herein. In some aspects, the polynucleotide contains a signal nucleic acid sequence, such as a nucleic acid sequence encoding the immunomodulatory polypeptide. In other instances, the polynucleotide contains a first nucleic acid sequence encoding the immunomodulatory polypeptide and a second nucleic acid sequence encoding a recombinant receptor. In some aspects, the recombinant receptor is or contains a chimeric antigen receptor (CAR). In some aspects, the recombinant receptor is or contains a T cell receptor (TCR), e.g., a transgenic TCR.

Any of the provided polynucleotides can be modified to remove CpG motifs and/or to optimize codons for translation in a particular species, such as human, canine, feline, equine, ovine, bovine, etc. species. In some embodiments, the polynucleotides are optimized for human codon usage (i.e., human codon-optimized). In some embodiments, the polynucleotides are modified to remove CpG motifs. In other embodiments, the provided polynucleotides are modified to remove CpG motifs and are codon-optimized, such as human codon-optimized. Methods of codon optimization and CpG motif detection and modification are well-known. Typically, polynucleotide optimization enhances transgene expression, increases transgene stability and preserves the amino acid sequence of the encoded polypeptide. Exemplary optimized polynucleotide sequences, encoding exemplary immunomodulatory polypeptides, are set forth in SEQ ID NOs: 102-107.

In some cases, the polynucleotide contains a signal sequence that encodes a signal peptide. For example, the signal sequence may encode a signal peptide derived from CD33, IL-12p40 or IL-12p35. Some such CD33, IL-12p40 or IL-12p35 signal peptides may have the sequence set forth in SEQ ID NO: 18, 12, or 19, respectively, or a sequence that has at least 95% sequence identity to such a sequence.

In some embodiments, the polynucleotide encoding the immunomodulatory polypeptide and/or recombinant receptor contains at least one promoter that is operatively linked to control expression of the immunomodulatory polypeptide and/or recombinant receptor. In some examples, the polynucleotide contains two, three, or more promoters operatively linked to control expression of the immunomodulatory polypeptide and/or recombinant receptor.

In some embodiments, expression of the immunomodulatory polypeptide and/or recombinant receptor is inducible or conditional. Thus, in some aspects, the polynucleotide encoding the immunomodulatory polypeptide and/or recombinant receptor contains a conditional promoter, enhancer, or transactivator. In some such aspects, the conditional promoter, enhancer, or transactivator is an inducible promoter, enhancer, or transactivator or a repressible promoter, enhancer, or transactivator. For example, in some embodiments, an inducible or conditional promoter can be used to restrict expression of the immunomodulatory polypeptide and/or recombinant receptor to a specific microenvironment, such as a tumor microenvironment. The tumor microenvironment includes conditions such as hypoxia and low glucose. In some embodiments, the inducible or conditional promoter is active in the presence of one or more conditions in the tumor microenvironment, such as hypoxia, low glucose, acidic pH, and/or oxidative stress. In other embodiments, expression driven by the inducible or conditional promoter is regulated by exposure to an exogenous agent, such as heat, radiation, or drug.

In some embodiments, expression of the immunomodulatory polypeptide and/or recombinant receptor is limited to hypoxic conditions. For example, hypoxia-inducible transcription factor-1 alpha (HIF-1 alpha)-mediated transcription binds to DNA motifs known as hypoxia response elements (HREs) under hypoxic conditions. Hence, HREs can be used to drive transgene expression specifically within areas of hypoxia, such as tumors. For example, a promoter yielding hypoxia-inducible gene expression can be constructed by combining one or more hypoxia response elements (HRE), from HIF-1-responsive genes, having the consensus core sequence 5'-(A/G)CGT(G/C)(G/C)-3' with a promoter, such as a basal promoter (e.g., CMV, SV40, or elongation factor-1 (EF-1) promoter). Exemplary HIF-1-responsive genes include erythropoietin (Epo), VEGF-A, phosphoglycerate kinase 1 (PGK1), lactate dehydrogenase A (LDH A), aldolase A (ALDA) and glyceraldehyde 3-phosphate dehydrogenase (GAPDH) and their respective HREs are set forth in SEQ ID NOs: 85-90.

In some embodiments, expression of the immunomodulatory polypeptide and/or recombinant receptor is restricted to conditions of low glucose. In such examples, a glucose-responsive promoter can be used to drive transgene expression in cells exposed to low glucose conditions, such as cells present in a tumor environment. Exemplary glucose-responsive promoters include the glucose-regulated protein GRP78 promoter and the hexokinase II promoter.

In some embodiments, exogenously controlled inducible promoters can be used to regulate expression of modulatory polypeptide and/or recombinant receptor. For example, radiation-inducible promoters, heat-inducible promoters, and/or drug-inducible promoters can be used to selectively drive transgene expression in, for example, targeted regions. In such embodiments, the location, duration, and level of transgene expression can be regulated by the administration of the exogenous source of induction.

In some embodiments transgene expression is limited to a radiation field upon application of radiation therapy, using a radiation inducible promoter. Methods of radiation therapy, such as conformal radiation therapy, interstitial radiation therapy, brachytherapy, or targeted delivery of radioisotopes can be exploited to induce localized expression of the immunomodulatory polypeptide and/or recombinant receptor under the regulation of a radiation-inducible promoter. In response to ionizing radiation, cells activate transcription of a variety of genes, such as c-jun, NFP, EGR-1 and p21(WAF-1). Exemplary radiation-inducible promoters include: EGR-1, Waf-1, RecA, and cIAP2 promoters. CArG elements of the EGR-1 promoter contain the consensus sequence $CC(A+T \text{ rich})_6GG$ motif (e.g., CCTT-ATTTGG; SEQ ID NO: 91), and also confer dose-dependent expression in response to exposure to radiation. Exemplary synthetic promoters can contain 1 or more CArG elements, such as 1, 2, 4, 6, 8, 10, 12, 14, or more CArG elements. Exemplary synthetic CArG-containing promoters are set forth in SEQ ID NOS: 92-95. When radiation inducible promoters are employed, cells provided herein, containing the constructs provided herein, containing a radiation-inducible promoter.

In some embodiments, expression of the immunomodulatory polypeptide and/or recombinant receptor is regulated by a heat inducible promoter. The cellular response to hyperthermia is associated with the synthesis of heat shock proteins (HSPs). Thus, expression of the modulatory polypeptide and/or recombinant receptor can be regulated by an HSP promoter, such as an HSP70B promoter, which will selectively activate transgene expression following hyperthermia treatment, thereby controlling the location, duration and level of expression of the transgene. In some embodiments, heat shock elements (HSE) can be introduced into the HSP promoter or other promoter to enhance the transcriptional response to heat. Gadd 153 is another exemplary heat-inducible promoter. Ultrasound and electromagnetic fields can also be used to stimulate transgene expression under the regulation of an HSP promoter. Temperatures and other exogenous forms of energy transfer, such as ultrasound and electromagnetic radiation, resulting in transgene expression in such systems can be empirically determined. In some embodiments, feedback loops can be incorporated to enhance transgene expression (see, e.g., Emilusen et al., Urol Int. 2001; 67(3):216-223).

In some embodiments, expression of the immunomodulatory polypeptide and/or recombinant receptor is regulated using or a drug-inducible promoter. For example, in some cases, the promoter, enhancer, or transactivator comprises a Lac operator sequence, a tetracycline operator sequence, a galactose operator sequence, a doxycycline operator sequence, a rapamycin operator sequence, a tamoxifen operator sequence, or a hormone-responsive operator sequence, or an analog thereof. In some instances, the inducible promoter comprises a tetracycline response element (TRE). In some embodiments, the inducible promoter comprises an estrogen response element (ERE), which can activate gene expression in the presence of tamoxifen. In some instances a drug-inducible element, such as a TRE, can be combined with a selected promoter to enhance transcription in the presence of drug, such as doxycycline. In some embodiments, the drug-inducible promoter is a small molecule-inducible promoter. Typically, a drug-inducible operator, such as a tetracycline operator, is an allosteric-on system, in which administration of a selected drug, such as doxycycline, initiates transcription of an otherwise silent transgene. In some embodiments, the multidrug resistance (mdr1) gene promoter, which contains drug-inducible response elements, can be employed to drive drug-dependent expression of the transgene. Effective doses of drug or hormone to achieve desired levels of transgene expression can be empirically determined, and methods of determining effective doses are well-known.

In some aspects, the expression of the immunomodulatory polypeptide is effected in the presence of an immune cell, e.g., T cell, activation, such as by a T cell activation factor. For example, in some instances, the promoter, enhancer or other response element or portion thereof is recognized by a transcription factor to drive expression of a gene whose activity is normally turned on by T cell activation. In some embodiments, the T cell activation factor can be a regulatory domain or region (e.g. promoter, enhancer or other response element) of a transcription factor whose activity is turned on by T cell activation. In some embodiments, the T cell activation factor is responsive to one or more of T cell activation, signal strength of TCR signaling and/or quality of TCR signaling.

In some embodiments, the T cell activation factor can be a regulatory element, such as a promoter, enhancer or response element or elements, that contains a binding site for a T cell transcription factor, and that thereby is associated with the downstream activity of a T cell transcription factor. In some embodiments, the transcription factor is nuclear factor of activated T-cells (NFAT), C/EBP, STAT1, STAT2, or NFκB. For example, in some embodiments, the T cell activation factor contains a response element or elements recognized by a nuclear factor of activated T-cells (NFAT), C/EBP, STAT1, STAT2, and NFκB. In some embodiments, the T cell activation factor can contain a regulatory element or elements recognized by or responsive to one or two, and in some cases three or more, unique transcription factors.

It is contemplated that one or more of the inducible, condition-dependent, and/or cell-specific promoters and/or regulatory elements can be combined to restrict and/or sensitize expression of the immunomodulatory polypeptide and/or recombinant receptor provided herein.

In some embodiments, such as those where the polynucleotide contains a first and second nucleic acid sequence, the polynucleotide further contains a nucleic acid sequence encoding a linking peptide between the first and second nucleic acid sequences. In some such cases, the linking peptide separates the translation products of the first and second nucleic acid sequences during or after translation. In some aspects, the linking peptide contains an internal ribosome entry site (IRES), a self-cleaving peptide, or a peptide that causes ribosome skipping, such as a T2A peptide.

In some embodiments, the polynucleotide encoding the immunomodulatory polypeptide and/or recombinant receptor is introduced into a composition containing cultured cells, such as by retroviral transduction, transfection, or transformation.

In some embodiments, the polynucleotide (nucleic acid molecule) is one that encodes the immunomodulatory polypeptide and/or recombinant receptor, e.g., chimeric receptor, such as any described above. Also provided are vectors or constructs containing such nucleic acid molecules. In some embodiments, the vectors or constructs contain one or more promoters operatively linked to the nucleotide encoding the polypeptide or receptor to drive expression thereof. In some embodiments, the promoter is operatively linked to one or more than one nucleic acid molecule.

Thus, also provided are vectors, such as those that contain any of the polynucleotides provided herein. In some cases, the vector is a viral vector, such as a retroviral vector, e.g., a lentiviral vector or a gammaretroviral vector.

In some embodiments, the vector or construct can contain a single promoter that drives the expression of one or more nucleic acid molecules. In some embodiments, such promoters can be multicistronic (bicistronic or tricistronic, see e.g., U.S. Pat. No. 6,060,273). For example, in some embodiments, transcription units can be engineered as a bicistronic unit containing an IRES (internal ribosome entry site), which allows coexpression of gene products (e.g. encoding a first and second recombinant receptor) by a message from a single promoter. Alternatively, in some cases, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 100), equine rhinitis A virus (E2A, e.g., SEQ ID NO: 99), Thosea asigna virus (T2A, e.g., SEQ ID NO: 76 or 96), and porcine teschovirus-1 (P2A, e.g., SEQ ID NO: 97 or 98) as described in U.S. Patent Publication No. 20070116690.

B. Cells and Preparation of Cells for Engineering

Also provided are cells, such as cells that contain the immunomodulatory polypeptide and/or an engineered recombinant receptor, such as described herein. In some embodiments, the cells are capable of secreting or are designed to secrete the immunomodulatory peptide. In some embodiments, the engineered cell secretes an immunomodulatory polypeptide that exhibits increased binding to a target cell expressing the target molecule as compared with its binding to a cell not expressing the target molecule. In some aspects, the engineered cell effects increased killing of a target cell expressing the target molecule compared to killing of cells not expressing the target molecule. In some instances, the increased persistence, activity, binding, and/or killing is greater than effected by a reference engineered cell expressing or secreting an immunomodulatory polypeptide comprising a polypeptide linker between subunits but not comprising the targeting moiety.

Also provided are populations of such cells, compositions containing such cells and/or enriched for such cells, such as in which cells expressing the immunomodulatory polypeptide and/or chimeric receptor make up at least 50, 60, 70, 80, 90, 91, 92, 93, 94, 95, 96, 97, 98, 99, or more percent of the total cells in the composition or cells of a certain type such as T cells or CD8+ or CD4+ cells. Among the compositions are pharmaceutical compositions and formulations for administration, such as for adoptive cell therapy. Also provided are therapeutic methods for administering the cells and compositions to subjects, e.g., patients.

Thus, also provided are genetically engineered cells expressing the immunomodulatory polypeptides and/or recombinant receptors e.g., CARs. The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the immunomodulatory polypeptide and/or recombinant receptor, e.g., CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, or pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, CD3$^+$, CD28$^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining T$_{CM}$-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L$^-$CD8$^+$ and/or CD62L$^+$CD8$^+$ fractions, such as using anti-CD8 and anti-CD62L antibodies.

In some embodiments, the enrichment for central memory T (T$_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for T$_{CM}$ cells is carried out by depletion of cells expressing CD4, CD14, CD45RA, and positive selection or enrichment for cells expressing CD62L. In one aspect, enrichment for central memory T (T$_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or ROR1, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L$^+$ and CD45RO$^+$. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood may be automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) *Blood.* 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Vectors and Methods for Genetic Engineering

Various methods for the introduction of genetically engineered components, e.g., immunomodulatory polypeptides and recombinant receptors, e.g., CARs or TCRs, are well known and may be used with the provided methods and compositions. Exemplary methods include those for transfer of nucleic acids encoding the polypeptides or receptors, including via viral vectors, e.g., retroviral or lentiviral, non-viral vectors or transposons, e.g. Sleeping Beauty transposon system. Methods of gene transfer can include transduction, electroporation or other method that results into gene transfer into the cell.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, it may be desired to safeguard against the potential that overexpression of a stimulatory factor (for example, a lymphokine or a cytokine) could potentially result in an unwanted outcome or lower efficacy in a subject, such as a factor associated with toxicity in a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphoribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) Blood. 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with an immunomodulatory polypeptide, a T cell receptor (TCR), or a chimeric antigen receptor (CAR). This transfection for the introduction of the gene of the desired polypeptide or receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

IV. Compositions, Formulations and Methods of Administration

Also provided are compositions containing the chimeric receptor, such as CAR or TCR, and compositions containing the engineered cells, including pharmaceutical compositions and formulations. Also provided are methods of using and uses of the compositions, such as in the treatment of diseases, conditions, and disorders in which the antigen is expressed, or in detection, diagnostic, and prognostic methods.

A. Compositions/Formulations

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being treated with the cells, preferably those with activities complementary to the cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the cells or antibodies are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and aryl sulfonic acids, for example, p-toluenesulfonic acid.

Active ingredients may be entrapped in microcapsules, in colloidal drug delivery systems (for example, liposomes, albumin microspheres, microemulsions, nanoparticles and nanocapsules) or in macroemulsions. In certain embodiments, the pharmaceutical composition is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The pharmaceutical composition in some embodiments contains immunomodulatory polypeptides and/or engineered cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The immunomodulatory polypeptides and/or engineered cells may be administered using standard administration techniques, formulations, and/or devices. Provided are formulations and devices, such as syringes and vials, for storage and administration of the compositions. Administration of the engineered cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

B. Methods of Administration

Provided are methods of administering the immunomodulatory polypeptides, engineered cells, and compositions, and uses of such immunomodulatory polypeptides, engineered cells, and compositions to treat or prevent diseases, conditions, and disorders, including cancers. In some embodiments, the immunomodulatory polypeptides, engineered cells, and compositions are administered to a subject or patient having the particular disease or condition to be treated, e.g., via adoptive cell therapy, such as adoptive T cell therapy. In some embodiments, provided cells and compositions are administered to a subject, such as a subject having or at risk for the disease or condition. In some aspects, the methods thereby treat, e.g., ameliorate one or more symptom of, the disease or condition, such as by lessening tumor burden in a cancer expressing an antigen recognized by an engineered T cell.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) *Nat Biotechnol.* 31(10): 928-933; Tsukahara et al. (2013) *Biochem Biophys Res Commun* 438(1): 84-9; Davila et al. (2013) *PLoS ONE* 8(4): e61338.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or transgenic TCR, specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

The provided methods and uses include methods and uses for adoptive cell therapy. In some embodiments, the methods include administration of the engineered cells or a composition containing the cells to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or super type as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $1\times10^8$ total recombinant receptor (e.g., CAR)-expressing cells, T cells, or peripheral blood mononuclear cells (PBMCs), e.g., in the range of about $1\times10^6$ to $1\times10^8$ such cells, such as $2\times10^6$, $5\times10^6$, $1\times10^7$, $5\times10^7$, or $1\times10^8$ or total such cells, or the range between any two of the foregoing values.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

V. Definitions

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof.

As used herein, a subject includes any living organism, such as humans and other mammals. Mammals include, but are not limited to, humans, and non-human animals, including farm animals, sport animals, rodents and pets.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, "operably linked" or "operatively linked" refers to the association of components, such as a DNA sequence, e.g. a heterologous nucleic acid) and a regulatory sequence(s), in such a way as to permit gene expression when the appropriate molecules (e.g. transcriptional activator proteins) are bound to the regulatory sequence. Hence, it means that the components described are in a relationship permitting them to function in their intended manner.

As used herein, "percent (%) sequence identity" and "percent identity" when used with respect to a nucleotide sequence (reference nucleotide sequence) or amino acid sequence (reference amino acid sequence) is defined as the percentage of nucleotide residues or amino acid residues, respectively, in a candidate sequence that are identical with the residues in the reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as lentiviral vectors.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

VI. Exemplary Embodiments

Among the provided embodiments are:
1. An immunomodulatory polypeptide comprising:
   a) a first peptide;
   b) a second peptide; and
   c) a joining region connecting the first and second peptides, wherein the joining region comprises a targeting moiety that binds to a target molecule.
2. The immunomodulatory polypeptide of embodiment 1, wherein at least one of the first and second peptide is a cytokine or chemokine, a subunit a cytokine or chemokine, or is a functional portion of the cytokine or chemokine.
3. The immunomodulatory polypeptide of embodiment 1 or embodiment 2, wherein the first peptide is a cytokine or chemokine, a subunit of a cytokine or chemokine, or is a functional portion of the cytokine or chemokine.
4. The immunomodulatory polypeptide of any of embodiments 1-3, wherein the second peptide is a cytokine or chemokine, a subunit of a cytokine or chemokine, or is a functional portion of the cytokine or chemokine.
5. The immunomodulatory polypeptide of any of embodiments 1-4, wherein both the first and second peptide are independently a cytokine or chemokine, a subunit of a cytokine or chemokine or a functional portion of the cytokine or chemokine.
6. The immunomodulatory polypeptide of any of embodiments 1-5, wherein the first peptide and the second peptide are the same cytokine or chemokine, or functional portions thereof, or are the same subunit of the same cytokine or chemokine.
7. The immunomodulatory polypeptide of any of embodiments 1-5, wherein the first and second peptide are a different cytokine or chemokine, or functional portions thereof, or are a different subunit of the same or different cytokine or chemokine.
8. The immunomodulatory polypeptide of any of embodiments 1-7, wherein the first peptide is a first subunit of a cytokine or chemokine and the second peptide is a second subunit of the cytokine or chemokine.
9. The immunomodulatory polypeptide of any of embodiments 1-7, wherein the cytokine or chemokine is a monomer.
10. The immunomodulatory polypeptide of any of embodiments 1-8, wherein the first and/or second peptide independently comprise a subunit of a cytokine or chemokine that is a multimeric protein.
11. The immunomodulatory polypeptide of any of embodiments 1-4, wherein the first or second peptide is a tag or label.
12. An immunomodulatory polypeptide comprising:
   a) a first peptide comprising a first subunit of a cytokine or chemokine or a functional portion thereof;
   b) a second peptide comprising a second subunit of the cytokine or chemokine or a functional portion thereof; and
   c) a joining region connecting the first and second peptides, wherein the joining region comprises a targeting moiety that binds to a target molecule.
13. The immunomodulatory polypeptide of any of embodiments 1-8, 10 and 12, wherein the cytokine or chemokine is a homodimer or heterodimer.
14. The immunomodulatory polypeptide of any of embodiments 1-13, wherein the joining region further comprises at least one polypeptide linker linking the targeting moiety to the first or second peptide.
15. The immunomodulatory polypeptide of any of embodiments 2-14, wherein the cytokine or chemokine or subunit or functional portion thereof is selected from the group consisting of: IL-12, IL-15, IL-2, IL-18, GM-CSF, IL-7, IL-21, IFNα, IFNβ, IFNγ, IL-17, IL-23, IL-3, IL-4, IL-5, IL-6, IL-9, IL-11, IL-13, IL-27, Erythropoietin, G-CSF, Growth hormone, Prolactin, Oncostatin M, and Leukemia inhibitory factor or a subunit or functional portion thereof.
16. The immunomodulatory polypeptide of any of embodiments 1-15, wherein the first or second peptide independently comprises a subunit of a cytokine or chemokine selected from IL-12, IL-23, IL-27 and IL-35 or a functional portion thereof.

17. The immunomodulatory polypeptide of any of embodiments 1-7 and 9-16, wherein the first or second peptide is independently a subunit of IL-12 or a functional portion thereof.

18. The immunomodulatory polypeptide of embodiment 17, wherein the first peptide comprises an IL-12 p35 subunit or an IL-12 p40 subunit or a functional portion thereof and the second peptide comprises the other of the IL-12 p35 subunit and the IL-12 p40 subunit or a functional portion thereof.

19. An immunomodulatory polypeptide comprising:
    a) a first peptide comprising a p35 subunit of IL-12 or a functional portion thereof;
    b) a second peptide comprising a p40 subunit of IL-12 or a functional portion thereof; and
    c) a joining region connecting the first and second peptides, wherein the joining region comprises a targeting moiety that binds to a target molecule.

20. The immunomodulatory peptide of embodiment 18 or embodiment 19, wherein the p35 subunit comprises the sequence of amino acids set forth in SEQ ID NO: 10 or a sequence that has at least 95% sequence identity thereto and/or the p40 subunit comprises the sequence of amino acids set forth in SEQ ID NO: 11 or a sequence that has at least 95% sequence identity thereto.

21. The immunomodulatory polypeptide of any of embodiments 18-20 wherein the joining region further comprises at least one polypeptide linker linking the targeting moiety to the p35 subunit or the p40 subunit.

22. The immunomodulatory polypeptide of any of embodiments 14-18 and 21, wherein the polypeptide linker comprises from about 2 to about 20 amino acids.

23. The immunomodulatory polypeptide of any of embodiments 14-18 and 21-22, wherein the polypeptide linker comprises the sequence GGGGS(n), wherein n is 1-5 (SEQ ID NO:29).

24. The immunomodulatory polypeptide of embodiment 23, wherein the polypeptide linker comprises the sequence set forth in any of SEQ ID NOs: 7-9.

25. The immunomodulatory polypeptide of any of embodiments 1-24, wherein the joining region comprises two polypeptide linkers.

26. The immunomodulatory polypeptide of any of embodiments 1-25, wherein the targeting moiety is comprised between a first polypeptide linker and a second polypeptide linker.

27. The immunomodulatory polypeptide of any of embodiments 1-26, wherein the target molecule is associated with a disease or disorder.

28. The immunomodulatory polypeptide of embodiment 27, wherein the disease or disorder is an infectious disease or disorder, an autoimmune disease, an inflammatory disease, or a tumor or a cancer.

29. The immunomodulatory polypeptide of any of embodiments 1-28, wherein the target molecule is associated with a tumor or present on a tumor.

30. The immunomodulatory polypeptide of any of embodiments 1-29, wherein the target molecule is a tumor antigen.

31. The immunomodulatory polypeptide of any of embodiments 1-30, wherein the target molecule is selected from the group consisting of: hepatocyte growth factor (HGF), hepatocyte growth factor receptor (HGFR), heparin, VEGF, VEGF-A, VEGFR2, VEGFR3, HER2, PD-1, tenascin-C, CTLA-4, LAGS, PD-L1, EGFR, EPCAM, RANKL, NG2 proteoglycan, CD20, CD52, CD19, CD3, CD30, IL-6, CD38, SLAMF7, GD2, CD13, CD274, CD279, CD40L, and CD47.

32. The immunomodulatory polypeptide of any of embodiments 1-31, wherein the targeting moiety comprises from about 3 to about 300 amino acids, about 3 to about 100 amino acids, about 3 to about 20 amino acids, about 6 to about 20 amino acids, or about 10 amino acids.

33. The immunomodulatory polypeptide of any of embodiments 1-32, wherein the targeting moiety exhibits a $k_{off}$ rate for binding the target molecule that is about $0.5 \times 10^{-4}$ sec$^{-1}$ or greater, about $1 \times 10^{-4}$ sec$^{-1}$ or greater, about $2 \times 10^{-4}$ sec$^{-1}$ or greater, about $3 \times 10^{-4}$ sec$^{-1}$ or greater, about $4 \times 10^{-4}$ sec$^{-1}$ of greater, about $5 \times 10^{-4}$ sec$^{-1}$ or greater, about $1 \times 10^{-3}$ sec$^{-1}$ or greater, about $1.5 \times 10^{-3}$ sec$^{-1}$ or greater, about $2 \times 10^{-3}$ sec$^{-1}$ or greater, about $3 \times 10^{-3}$ sec$^{-1}$ or greater, about $4 \times 10^{-3}$ sec$^{-1}$, about $5 \times 10^{-3}$ sec$^{-1}$ or greater, about $1 \times 10^{-2}$ sec or greater, or about $5 \times 10^{-1}$ sec$^{-1}$ or greater.

34. The immunomodulatory polypeptide of any of embodiments 1-33, wherein the targeting moiety is or comprises an antibody or antibody fragment.

35. The immunomodulatory polypeptide of embodiment 34, wherein the antibody fragment is a single chain fragment.

36. The immunomodulatory polypeptide of embodiment 34 or embodiment 35, wherein the antibody fragment is a single domain antibody comprising the variable heavy chain region.

37. The immunomodulatory polypeptide of embodiment 34 or embodiment 35, wherein the antibody fragment comprises antibody variable regions joined by a flexible linker.

38. The immunomodulatory polypeptide of any of embodiments 34-37, wherein the antibody fragment comprises an scFv.

39. The immunomodulatory polypeptide of any of embodiments 1-38, wherein the targeting moiety comprises a variable heavy (VH) chain and/or variable light (VL) chain of an antibody selected from the group consisting of: trastuzumab, pertuzumab, ramucirumab, atezolizumab, bevacizumab, panitumumab, cetuximab, necitumumab, denosumab, nivolumab, pembrolizumab, rituximab, ofatumumab, obinutuzumab, alemtuzumab, blinatumomab, brentuximab vedotin, siltuximab, ipilimumab, daratumumab, elotuzumab, dinutuximab, Catumaxomab.

40. The immunomodulatory polypeptide of any of embodiments 1-39, wherein the targeting moiety comprises a $V_H$ chain and/or $V_L$ chain of an anti-EPCAM antibody.

41. The immunomodulatory polypeptide of any of embodiments 1-40, wherein the targeting moiety comprises the sequence set forth in SEQ ID NO: 17, 24 or 25, or a sequence that has at least 95% sequence identity to SEQ ID NO: 17, 24 or 25 and binds to the target molecule.

42. The immunomodulatory polypeptide of any of embodiments 1-41, wherein the immunomodulatory polypeptide comprises the sequence set forth in SEQ ID NO: 6, or a sequence that has at least 95% sequence identity to such a sequence.

43. The immunomodulatory polypeptide of any of embodiments 1-33, wherein the targeting moiety is or comprises a peptide binding motif.

44. The immunomodulatory polypeptide of any of embodiments 1-33 and 43, wherein the targeting moiety is a heparin binding peptide.
45. The immunomodulatory polypeptide of embodiment 44, wherein the heparin binding peptide (HBP) is derived from fibronectin or BMP4, and/or is of bovine origin.
46. The immunomodulatory polypeptide of any of embodiments 1-33, and 43, wherein the targeting moiety is selected from the group consisting of: a hepatocyte growth factor (HGF) binding peptide, a VEGF binding peptide, a VEGF-A binding peptide, a VEGFR2 binding peptide, an EPCAM binding peptide, a HER2 binding peptide, a PD-1 binding peptide, a tenascin-C binding peptide, a CTLA-4 binding peptide, a LAGS binding peptide, a PD-L1 binding peptide, a EGFR binding peptide, a RANKL binding peptide, a CD20 binding peptide, a CD52 binding peptide, a CD19 binding peptide, a CD3 binding peptide, a CD30 binding peptide, a IL-6 binding peptide, a CD38 binding peptide, a SLAMF7 binding peptide, a GD2 binding peptide, a CD274 binding peptide, a CD279 binding peptide, a CD40L binding peptide, and a CD47 binding peptide.
47. The immunomodulatory polypeptide of any of embodiments 1-33, 43 and 46 wherein the targeting moiety comprises an HGF binding peptide or an EGFR binding peptide (EGFRBP).
48. The immunomodulatory polypeptide of any of embodiments 1-33 and 43-47 wherein the targeting moiety comprises the sequence set forth in any of SEQ ID NOs: 13, 14, 15, 16, 26, 27 or 28, or a sequence that has at least 95% sequence identity to any of SEQ ID NOs: 13, 14, 15, 16, 26, 27 or 28 and binds to the target molecule.
49. The immunomodulatory polypeptide of any of embodiments 1-33 and 43-48, wherein the immunomodulatory polypeptide comprises the sequence set forth in any of SEQ ID NOs: 1-5, or a sequence that has at least 95% sequence identity to any of SEQ ID NOs: 1-5.
50. The immunomodulatory polypeptide of any of embodiments 1-49, wherein the immunomodulatory polypeptide exhibits increased activity to stimulate via the IL-12R compared to a reference IL-12.
51. The immunomodulatory polypeptide of embodiment 50, wherein the reference IL-12 does not comprise a joining region or comprises a joining region that consists of the sequence set forth in any one of SEQ ID NOs 7-9.
52. The immunomodulatory polypeptide of any of embodiments 1-51, wherein the immunomodulatory polypeptide exhibits increased binding to a target cell expressing the target molecule as compared with its binding to a cell not expressing the target molecule.
53. The immunomodulatory polypeptide of any of embodiments 50-52, wherein the increased activity and/or binding is by greater than 1.2-fold, greater than 1.5-fold, greater than 2.0-fold, greater than 3.0-fold, greater than 4.0-fold, greater than 5.0-fold or greater than 10.0-fold.
54. The immunomodulatory polypeptide of any of embodiments 1-53, wherein the immunomodulatory polypeptide binds one or more cognate receptor(s) with increased, decreased, or similar binding affinity as a recombinant immunomodulatory polypeptide not containing the joining region.
55. The immunomodulatory polypeptide of any of embodiments 1-54, wherein, the immunomodulatory polypeptide binds the one or more cognate receptor(s) with an equilibrium dissociation constant ($K_D$) that ranges from or from about $10^{-5}$ M to or to about $10^{-15}$ M, $10^{-6}$ M to or to about $10^{-12}$ M, from or from about $10^{-7}$ M to or to about $10^{-11}$ M, from or from about $10^{-6}$ M to or to about $10^{-8}$ M, or from or from about $10^{-7}$ M to or to about $10^{-8}$ M.
56. The immunomodulatory polypeptide of any of embodiments 1-54, wherein, the immunomodulatory polypeptide binds the one or more cognate receptor(s) with a $K_D$ that is at or about or less than at or about 100, 50, 40, 30, 25, 20, 19, 18, 17, 16, 15, 14, 13, 12, 11, 10, 9, 8, 7, 6, 5, 4, 3, 2, 1, 0.5, or 0.1 nM; or is at or about or less than at or about 1 nM, 100 picomolar (pM), 90 pM, 80 pM, 70 pM, 60 pM, 50 pM, 40 pM, 30 pM, 25 pM, 20 pM, 15 pM, 10 pM, or 1 pM.
57. A polynucleotide encoding the immunomodulatory polypeptide of any of embodiments 1-56.
58. The polynucleotide of embodiment 57, further comprising a signal sequence.
59. The polynucleotide of embodiment 58, wherein the signal sequence encodes a signal peptide derived from CD33.
60. The polynucleotide of embodiment 59, wherein the signal peptide comprises the sequence set forth in SEQ ID NO: 18, or a sequence that has at least 95% sequence identity to such a sequence.
61. The polynucleotide of any of embodiments 57-60, wherein the polynucleotide further comprises at least one promoter, enhancer or transactivator that is operatively linked to control expression of the immunomodulatory polypeptide.
62. The polynucleotide of embodiment 61, wherein the expression of the immunomodulatory polypeptide is inducible or conditional.
63. The polynucleotide of embodiment 61 or 62, wherein the promoter, enhancer or transactivator is a T cell activation factor.
64. The polynucleotide of any of embodiments 61-63, wherein the promoter, enhancer or transactivator contains a binding site for one or more T cell transcription factor(s).
65. The polynucleotide of embodiment 64, wherein the T cell transcription factor is nuclear factor of activated T-cells (NFAT), C/EBP, STAT1, STAT2, and/or NFκB.
66. The polynucleotide of embodiment 61 or embodiment 62, wherein activation of the promoter, enhancer, or transactivator is conditional, optionally an inducible promoter, enhancer, or transactivator or a repressible promoter, enhance or transactivator.
67. The polynucleotide of any of embodiments 61, 62, or 66, wherein the promoter, enhancer or transactivator is active in the presence of one or more conditions present in the tumor microenvironment.
68. The polynucleotide of embodiment 67, wherein the one or more conditions present in the tumor microenvironment is selected from hypoxia, low glucose, acidic pH or oxidative stress.
69. The polynucleotide of embodiment 67 or 68, wherein the one or more conditions present in the tumor microenvironment is hypoxia.
70. The polynucleotide of any of embodiments 61, 62, or 66-69, wherein the polynucleotide is operatively linked to a promoter, and the promoter is a HIF-1-alpha-responsive promoter.

71. The polynucleotide of any of embodiments 61, 62, or 66-70, wherein the polynucleotide is operatively linked to a promoter, and the promoter comprises one or more hypoxia response element.

72. The polynucleotide of embodiment 71, wherein the hypoxia response element comprises the sequence 5'-(A/G)CGT(G/C)(G/C)-3'.

73. The polynucleotide of any of embodiments 70-72, wherein the promoter is an erythropoietin (Epo), VEGF-A, phosphoglycerate kinase 1 (PGK1), lactate dehydrogenase A (LDH A), aldolase A (ALDA) or glyceraldehyde 3-phosphate dehydrogenase (GAPDH) promoter.

74. The polynucleotide of embodiment 73 wherein the promoter is set forth in any of SEQ ID NOs: 85-90.

75. The polynucleotide of embodiment 67 or 68, wherein the one or more conditions present in the tumor micorenvironment is low glucose.

76. The polynucleotide of any of embodiments 61, 62, 66-68, or 75, wherein the polynucleotide is operatively linked to a promoter that is a GRP78 or hexokinase II promoter.

77. The polynucleotide of any of embodiments 61, 62, or 66, wherein the promoter, enhancer, or transactivator is inducible by radiation, heat or in the presence of a drug.

78. The polynucleotide of embodiment 77, wherein the promoter is a radiation-inducible promoter.

79. The polynucleotide of embodiment 77, wherein the radiation-inducible promoter comprises a CArG element or a CC(A+T rich)$_6$GG motif.

80. The polynucleotide of embodiment 78 or 79, wherein the radiation-inducible promoter is an EGR-1, Waf-1, RecA, or cIAP2 promoter or is a synthetic promoter.

81. The polynucleotide of any of embodiments 78-80, wherein the radiation-inducible promoter is a synthetic promoter that comprises the any of the sequences set forth in SEQ ID NOs 92-95.

82. The polynucleotide of embodiment 77, wherein the promoter, enhancer or transactivator is heat-inducible promoter, enhancer or transactivator.

83. The polynucleotide of embodiment 82, wherein the heat-inducible promoter, enhancer, or transactivator comprises a heat shock element (HSE).

84. The polynucleotide of embodiment 83, wherein the heat-inducible promoter, enhancer, or transactivator is a heat shock promoter (HSP).

85. The polynucleotide of embodiment 84h, wherein the HSP is an HSP70B promoter.

86. The polynucleotide of embodiment 73, wherein the heat-inducible promoter, enhancer, or transactivator is a Gadd 153 promoter.

87. The polynucleotide of embodiment 77, wherein the promoter, enhancer, or transactivator is a drug-inducible promoter, enhancer, or transactivator.

88. The polynucleotide of embodiment 66 or embodiment 87, wherein the inducible promoter, enhancer, or transactivator comprises a Lac operator sequence, a tetracycline operator sequence, a galactose operator sequence or a doxycycline operator sequence, a rapamycin operator sequence, a tamoxifen operator sequence, or a hormone-responsive operator sequence, or an analog thereof.

89. The polynucleotide of any of embodiments 66, 87 or 88, wherein the inducible promoter comprises a tetracycline response element (TRE).

90. The polynucleotide of embodiment 87, wherein the drug-inducible promoter, enhancer, or transactivator comprises a multidrug resistance (mdr1) gene promoter.

91. The polynucleotide of any of embodiments 57-90, wherein the polynucleotide comprises a single nucleic acid sequence.

92. The polynucleotide of any of embodiments 57-90, comprising a first nucleic acid sequence encoding the immunomodulatory polypeptide and a second nucleic acid sequence encoding a recombinant receptor.

93. The polynucleotide of embodiment 92, wherein the recombinant receptor is or comprises a chimeric antigen receptor (CAR).

94. The polynucleotide of embodiment 92 or embodiment 93, further comprising at least one promoter that is operatively linked to control expression of the immunomodulatory polypeptide and/or the recombinant receptor.

95. The polynucleotide of any of embodiments 92-94, further comprising an internal ribosome entry site (IRES) or a nucleic acid sequence encoding a linking peptide between the first and second nucleic acid sequences, wherein the linking peptide separates the translation products of the first and second nucleic acid sequences during or after translation.

96. The polynucleotide of embodiment 95, wherein the linking peptide comprises a self-cleaving peptide, or a peptide that causes ribosome skipping, optionally a T2A peptide.

97. The polynucleotide of any of embodiments 57-96 that is optimized to remove CpG motifs and/or is codon-optimized.

98. The polynucleotide of embodiment 97, that is human codon-optimized.

99. A vector, comprising the polynucleotide of any of embodiments 57-98.

100. The vector of embodiment 99 that is a viral vector.

101. The vector of embodiment 99 or embodiment 100 that is a retroviral vector.

102. The vector of any of embodiments 99-101 that is a lentiviral vector or a gammaretroviral vector.

103. An engineered cell comprising the immunomodulatory polypeptide of any of embodiments 1-56.

104. An engineered cell comprising the polynucleotide of any of embodiments 57-98.

105. An engineered cell comprising the vector of any of embodiments 99-102.

106. The engineered cell of any of embodiments 103-105, wherein the engineered cell secretes the immunomodulatory polypeptide.

107. The engineered cell of any of embodiments 103-106, further comprising a recombinant receptor.

108. The engineered cell of embodiment 107, wherein the recombinant receptor binds to a target antigen that is associated with a disease or disorder.

109. The engineered cell of embodiment 108, wherein the disease or disorder is an infectious disease or disorder, an autoimmune disease, an inflammatory disease, or a tumor or a cancer.

110. The engineered cell of embodiment 108 or embodiment 109, wherein the target antigen is a tumor antigen.

111. The engineered cell of any of embodiments 108-110, wherein the target antigen is selected from the group consisting of ROR1, Her2, L1-CAM, CD19, CD20, CD22, mesothelin, CEA, hepatitis B surface antigen, anti-folate receptor, CD23, CD24, CD30, CD33, CD38, CD44, EGFR, EGP-2, EGP-4, EPHa2, ErbB2, ErbB3, ErbB4, FBP, fetal acetylcholine receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, TAG72, VEGF-R2, VEGFR3, carcinoembryonic antigen (CEA), prostate specific antigen, PSMA, estrogen receptor, progesterone receptor, ephrinB2, CD123, CS-1, c-Met, GD-2, MAGE A3, CE7, Wilms Tumor 1 (WT-1), and cyclin A1 (CCNA1).

112 The engineered cell of any of embodiments 103-111, wherein the targeting moiety is human or is derived from a human protein.

113. The engineered cell of any of embodiments 103-112, wherein the immunomodulatory protein is not immunogenic and/or does not induce an immune response in a subject in which it is administered.

114. The engineered cell of any of embodiments 107-113, wherein the recombinant receptor is a functional non-TCR antigen receptor or a transgenic TCR.

115. The engineered cell of any of embodiments 107-114, wherein the recombinant receptor is a chimeric antigen receptor (CAR).

116. The engineered cell of any of embodiments 107-115, wherein the recombinant receptor comprises an extracellular portion comprising an antigen-binding domain.

117. The engineered cell of embodiment 116, wherein the antigen-binding domain is or comprises an antibody or an antibody fragment.

118. The engineered cell of embodiment 117, wherein the antibody fragment is a single chain fragment.

119. The engineered cell of embodiment 117 or embodiment 118, wherein the fragment comprises antibody variable regions joined by a flexible linker.

120. The engineered cell of any of embodiments 117-119, wherein the fragment comprises an scFv.

121. The engineered cell of any of embodiments 107-120, wherein the recombinant receptor comprises an intracellular signaling region.

122. The engineered cell of embodiment 121, wherein the intracellular signaling region comprises an intracellular signaling domain.

123. The engineered cell of embodiment 122, wherein the intracellular signaling domain is or comprises a primary signaling domain, a signaling domain that is capable of inducing a primary activation signal in a T cell, a signaling domains of a T cell receptor (TCR) component, and/or a signaling domain comprising an immunoreceptor tyrosine-based activation motif (ITAM).

124. The engineered cell of embodiment 122, wherein the intracellular signaling domain is or comprises an intracellular signaling domain of a CD3 chain, optionally a CD3-zeta (CD3ζ) chain, or a signaling portion thereof.

125. The engineered cell of any of embodiments 122-124, further comprising a transmembrane domain disposed between the extracellular portion and the intracellular signaling region.

126. The engineered cell of any of embodiments 122-125, wherein the intracellular signaling region further comprises a costimulatory signaling domain.

127. The engineered cell of embodiment 126, wherein the costimulatory signaling domain comprises an intracellular signaling domain of a T cell costimulatory molecule or a signaling portion thereof.

128. The engineered cell of embodiment 126 or embodiment 127, wherein the costimulatory signaling domain comprises an intracellular signaling domain of a CD28, a 4-1BB or an ICOS, or a signaling portion thereof.

129. The engineered cell of any of embodiments 126-128, wherein the costimulatory signaling domain is between the transmembrane domain and the intracellular signaling domain.

130. The engineered cell of any of embodiments 103-129, wherein the engineered cell is a T cell.

131. The engineered cell of any of embodiments 103-130 that is a CD8+ T cell or a CD4+ T cell.

132. The engineered cell of any of embodiments 103-131, wherein the engineered cell exhibits increased persistence and/or survival compared to cells not engineered or compared to cells comprising a recombinant receptor but not the immunomodulatory polypeptide.

133. The engineered cell of any of embodiments 103-132, wherein the engineered cell exhibits increased activity to stimulate via the IL-12R compared to a reference IL-12.

134. The engineered cell of embodiment 133, wherein the reference IL-12 does not comprise a joining region or comprises a joining region that consists of any of the sequences set forth in SEQ ID NOs 7-9.

135. The engineered cell of any of embodiments 103-134, wherein the engineered cell secretes an immunomodulatory polypeptide that exhibits increased binding to a target cell expressing the target molecule as compared with its binding to a cell not expressing the target molecule.

136. The engineered cell of any of embodiments 103-135, wherein the engineered cell effects increased killing of a target cell expressing the target molecule compared to killing of cells not expressing the target molecule.

137. The engineered cell of any of embodiments 132-136, wherein the increased persistence, activity, binding, and/or killing is greater than effected by a reference engineered cell expressing or secreting an immunomodulatory polypeptide comprising a polypeptide linker between subunits but not comprising the targeting moiety.

138. A composition comprising the immunomodulatory polypeptide of any of embodiments 1-56.

139. A composition comprising the engineered cell of any of embodiments 103-137.

140. The composition of embodiment 138 or embodiment 139, further comprising a pharmaceutically acceptable excipient.

141. A method of treatment comprising administering the immunomodulatory polypeptide of any of embodiments 1-56 the engineered cell of any of embodiments 103-137, or the composition of any of embodiments 138-140 to a subject having a disease or disorder.

142. The method of embodiment 141, wherein the immunomodulatory polypeptide specifically binds to a target molecule expressed by a cell associated with the disease or disorder.

143. The method of treatment of embodiment 141 or embodiment 142, wherein the engineered cell expresses a recombinant receptor that specifically binds to an antigen associated with the disease or condition.

144. The method of any of embodiments 141-143, wherein the disease or disorder is a cancer, a tumor, an autoimmune disease or disorder, or an infectious disease.

VII. Examples

The following examples are included for illustrative purposes only and are not intended to limit the scope of the invention.

Example 1: Design of IL-12 Immunomodulatory Polypeptides

Single chain IL-12 (scIL-12) immunomodulatory polypeptides were designed that included one or more targeting moieties that specifically bind to a particular target molecule or motif, for example, for use in targeting, localizing, or orienting the polypeptide in or near or in a particular orientation with respect to a cell expressing the target molecule or motif. The constructs were synthesized as single-chain sequences encoding the p35 subunit (set forth in SEQ ID NO:10) and p40 subunit (set forth in SEQ ID NO:11) of IL-12 joined by a polypeptide linker containing the targeting moiety and, optionally, one or more G4S(3) peptide linkers (SEQ ID NO:7) joining the targeting moiety to the IL-12 subunits.

Table 3 sets forth the sequences of exemplary IL-12 immunomodulatory polypeptides containing various targeting moieties derived from either: a heparin binding peptide of BMP4 (HBP BMP4; SEQ ID NO:13), a heparin binding peptide of fibronectin (HBP FBN, SEQ ID NO:14), a hepatocyte growth factor binding peptide (HGFBP, SEQ ID NO:15), an epidermal growth factor receptor binding peptide (EGFRBP; SEQ ID NO:16) or an anti-EPCAM scFv antibody (SEQ ID NO:17). A control polypeptide in which the polypeptide linker contained a G4S(3) linker alone (set forth in SEQ ID NO:9) and no targeting moiety joining the subunits also was designed (designated scIL-12). Each sequence also was designed to encode an N-terminal signal sequence derived from CD33 (MPLLLLLPLLWAGALAM, SEQ ID NO:18) for secretion of the immunomodulatory protein when expressed in a cell. In some cases, one or more tags were included at the C-terminus (e.g. 6×His-tag, SEQ ID NO:20 or Strep-Tag® II, SEQ ID NO:21).

TABLE 3

Exemplary IL-12 Immunomodulatory Polypeptides

| Name | Targeting moiety/ moieties | Sequence | SEQ ID NO. |
|---|---|---|---|
| scIL-12 | None | IWELKKDVYVVELDWYPDAPGEMVVLTCDTPEEDGITWTLDQSS<br>EVLGSGKTLTIQVKEFGDAGQYTCHKGGEVLSHSLLLLHKKEDG<br>IWSTDILKDQKEPKNKTFLRCEAKNYSGRFTCWWLTTISTDLTF<br>SVKSSRGSSDPQGVTCGAATLSAERVRGDNKEYEYSVECQEDSA<br>CPAAEESLPIEVMVDAVHKLKYENYTSSFFIRDIIKPDPPKNLQ<br>LKPLKNSRQVEVSWEYPDTWSTPHSYFSLTFCVQVQGKSKREKK<br>DRVFTDKTSATVICRKNASISVRAQDRYYSSSWSEWASVPCSGG<br>GGSGGGGSGGGGSRNLPVATPDPGMFPCLHHSQNLLRAVSNMLQ<br>KARQTLEFYPCTSEEIDHEDITKDKTSTVEACLPLELTKNESCL<br>NSRETSFITNGSCLASRKTSFMMALCLSSIYEDLKMYQVEFKTM<br>NAKLLMDPKRQIFLDQNMLAVIDELMQALNFNSETVPQKSSLEE<br>PDFYKTKIKLCILLHAFRIRAVTIDRVMSYLNAS | 1 |
| scIL-12-HBP BMP4 | HBP, BMP4 | IWELKKDVYVVELDWYPDAPGEMVVLTCDTPEEDGITWTLDQSS<br>EVLGSGKTLTIQVKEFGDAGQYTCHKGGEVLSHSLLLLHKKEDG<br>IWSTDILKDQKEPKNKTFLRCEAKNYSGRFTCWWLTTISTDLTF<br>SVKSSRGSSDPQGVTCGAATLSAERVRGDNKEYEYSVECQEDSA<br>CPAAEESLPIEVMVDAVHKLKYENYTSSFFIRDIIKPDPPKNLQ<br>LKPLKNSRQVEVSWEYPDTWSTPHSYFSLTFCVQVQGKSKREKK<br>DRVFTDKTSATVICRKNASISVRAQDRYYSSSWSEWASVPCSGG<br>GGSRKKNPNCRRHGGGGSRNLPVATPDPGMFPCLHHSQNLLRAV<br>SNMLQKARQTLEFYPCTSEEIDHEDITKDKTSTVEACLPLELTK<br>NESCLNSRETSFITNGSCLASRKTSFMMALCLSSIYEDLKMYQV<br>EFKTMNAKLLMDPKRQIFLDQNMLAVIDELMQALNFNSETVPQK<br>SSLEEPDFYKTKIKLCILLHAFRIRAVTIDRVMSYLNAS | 2 |
| scIL-12-HBP FBN | HBP FBN | IWELKKDVYVVELDWYPDAPGEMVVLTCDTPEEDGITWTLDQSS<br>EVLGSGKTLTIQVKEFGDAGQYTCHKGGEVLSHSLLLLHKKEDG<br>IWSTDILKDQKEPKNKTFLRCEAKNYSGRFTCWWLTTISTDLTF<br>SVKSSRGSSDPQGVTCGAATLSAERVRGDNKEYEYSVECQEDSA<br>CPAAEESLPIEVMVDAVHKLKYENYTSSFFIRDIIKPDPPKNLQ<br>LKPLKNSRQVEVSWEYPDTWSTPHSYFSLTFCVQVQGKSKREKK<br>DRVFTDKTSATVICRKNASISVRAQDRYYSSSWSEWASVPCSGG<br>GGSKNNQKSEPLIGRKKTGGGGSRNLPVATPDPGMFPCLHHSQN<br>LLRAVSNMLQKARQTLEFYPCTSEEIDHEDITKDKTSTVEACLP<br>LELTKNESCLNSRETSFITNGSCLASRKTSFMMALCLSSIYEDL<br>KMYQVEFKTMNAKLLMDPKRQIFLDQNMLAVIDELMQALNFNSE<br>TVPQKSSLEEPDFYKTKIKLCILLHAFRIRAVTIDRVMSYLNAS | 3 |
| scIL-12-HGFBP | HGFBP | IWELKKDVYVVELDWYPDAPGEMVVLTCDTPEEDGITWTLDQSS<br>EVLGSGKTLTIQVKEFGDAGQYTCHKGGEVLSHSLLLLHKKEDG<br>IWSTDILKDQKEPKNKTFLRCEAKNYSGRFTCWWLTTISTDLTF<br>SVKSSRGSSDPQGVTCGAATLSAERVRGDNKEYEYSVECQEDSA<br>CPAAEESLPIEVMVDAVHKLKYENYTSSFFIRDIIKPDPPKNLQ<br>LKPLKNSRQVEVSWEYPDTWSTPHSYFSLTFCVQVQGKSKREKK<br>DRVFTDKTSATVICRKNASISVRAQDRYYSSSWSEWASVPCSGG<br>GGSVWNWVCFRDVGCDWVLGGGGSRNLPVATPDPGMFPCLHHSQ<br>NLLRAVSNMLQKARQTLEFYPCTSEEIDHEDITKDKTSTVEACL | 4 |

TABLE 3-continued Exemplary IL-12 Immunomodulatory Polypeptides

| Name | Targeting moiety/ moieties | Sequence | SEQ ID NO. |
|---|---|---|---|
| | | PLELTKNESCLNSRETSFITNGSCLASRKTSFMMALCLSSIYED LKMYQVEFKTMNAKLLMDPKRQIFLDQNMLAVIDELMQALNFNS ETVPQKSSLEEPDFYKTKIKLCILLHAFRIRAVTIDRVMSYLNA S | |
| scIL-12-EGFRBP | EGFRBP | IWELKKDVYVVELDWYPDAPGEMVVLTCDTPEEDGITWTLDQSS EVLGSGKTLTIQVKEFGDAGQYTCHKGGEVLSHSLLLLHKKEDG IWSTDILKDQKEPKNKTFLRCEAKNYSGRFTCWWLTTISTDLTF SVKSSRGSSDPQGVTCGAATLSAERVRGDNKEYEYSVECQEDSA CPAAEESLPIEVMVDAVHKLKYENYTSSFFIRDIIKPDPPKNLQ LKPLKNSRQVEVSWEYPDTWSTPHSYFSLTFCVQVQGKSKREKK DRVFTDKTSATVICRKNASISVRAQDRYYSSSWSEWASVPCSGG GGSSVDNPHVCGGGGSRNLPVATPDPGMFPCLHHSQNLLRAVSN MLQKARQTLEFYPCTSEEIDHEDITKDKTSTVEACLPLELTKNE SCLNSRETSFITNGSCLASRKTSFMMALCLSSIYEDLKMYQVEF KTMNAKLLMDPKRQIFLDQNMLAVIDELMQALNFNSETVPQKSS LEEPDFYKTKIKLCILLHAFRIRAVTIDRVMSYLNAS | 5 |
| scIL-12-Anti EPCAM | Anti EPCAM | IWELKKDVYVVELDWYPDAPGEMVVLTCDTPEEDGITWTLDQSS EVLGSGKTLTIQVKEFGDAGQYTCHKGGEVLSHSLLLLHKKEDG IWSTDILKDQKEPKNKTFLRCEAKNYSGRFTCWWLTTISTDLTF SVKSSRGSSDPQGVTCGAATLSAERVRGDNKEYEYSVECQEDSA CPAAEESLPIEVMVDAVHKLKYENYTSSFFIRDIIKPDPPKNLQ LKPLKNSRQVEVSWEYPDTWSTPHSYFSLTFCVQVQGKSKREKK DRVFTDKTSATVICRKNASISVRAQDRYYSSSWSEWASVPCSGG GGSQVQLVQSGAEVKKPGSSVKVSCKASGGTFSSYAISVVVRQA PGQGLEWMGGIIPIFGTANYAQKFQGRVTITADESTSTAYMELS SLRSEDTAVYYCARGLLWNYWGQGTLVTVSSKLSGSASAPKLEE GEFSEARVETTLTQSPATLSVSPGERATLSCRASQSVSSNLAVV YQQKPGQAPRLLIYGASTRATGIPARFSGSGSGTEFTLTISSLQ SEDPAVYYCQQYNNWPPGFTFGPGTKVDIKGGGGSRNLPVATPD PGMFPCLHHSQNLLRAVSNMLQKARQTLEFYPCTSEEIDHEDIT KDKTSTVEACLPLELTKNESCLNSRETSFITNGSCLASRKTSFM MALCLSSIYEDLKMYQVEFKTMNAKLLMDPKRQIFLDQNMLAVI DELMQALNFNSETVPQKSSLEEPDFYKTKIKLCILLHAFRIRAV TIDRVMSYLNAS | 6 |

Example 2: Assessment of IL-12-Mediated Cell Stimulation by the Immunomodulatory Polypeptides Exemplary IL-12 immunomodulatory polypeptides, scIL-12-HBP FBN (SEQ ID NO:3) and scIL-12-EGFRBP (SEQ ID NO:5), as described in Example 1, were tested for activity to stimulate secretion of cytokines from cells expressing the IL-12 receptor (IL-12R). As a control, scIL-12 (SEQ ID NO:1) that did not contain an integrated targeting moiety in its linker or recombinant human IL-12 (rHuIL-12) (R&D Systems) were used as controls.

Peripheral blood mononuclear cells (PBMCs) were stimulated with phytohemagglutinin (PHA) to generate PHA blasts in order to upregulate surface expression of the IL-12 receptor (IL-12R). PHA blasts were stimulated with increased concentrations of the various immunomodulatory polypeptides or controls at concentrations ranging from 0-25 ng/mL. At 24 hours and 72 hours post-stimulation of cells, supernatant was collected and measured for interferon gamma (IFNγ) of GM-CSF by ELISA. The results are shown in FIG. 1.

As shown in FIG. 1, a dose-dependent increase in IFNγ and GM-CSF was observed following stimulation of the PHA blasts with the IL-12 immunomodulatory polypeptides or controls. At 24 hours post-stimulation, PHA blasts treated with the test polypeptides scIL-12-HBP FBN and scIL-12-EGFRBP as well as the scIL-12 control polypeptide displayed similar levels of IFNγ and GM-CSF as those treated with rHuIL-12 across the various concentrations. However, at 72 hours post-stimulation, the levels of IFNγ and GM-CSF were substantially higher in PHA blasts stimulated with each of the single chain polypeptides (scIL-12-HBP FBN, scIL-12-EGFRBP or sc IL-12 G4S(3) polypeptides) compared to PHA blasts stimulated with rHuIL-12. The results demonstrated that single chain forms of IL-12 immunomodulatory polypeptides comprising the p35 and p40 subunits joined by a polypeptide linker, and optionally comprising a targeting moiety, may be more potent immune cell activators than rHuIL-12.

Example 3: Assessment of T Cell Proliferation Following Stimulation with IL-12 Immunomodulatory Polypeptides T cells were isolated by immunoaffinity-based enrichment from three human donor subjects and cells from each donor were activated and transduced with a viral vector encoding an anti-CD19 CAR. The CAR contained an anti-CD19 scFv, an Ig-derived spacer, a human CD28-derived transmembrane domain, a human 4-1BB-derived intracellular signaling domain and a human CD3 zeta-derived signaling domain. CD19-expressing target cells (K562 cells transduced to express CD19, K562-CD19) at 20,000 cells per well in triplicate in a 96-well poly-D-lysine-coated plate were incubated with the various CAR-expressing T cells (at various effector:target ratios (5:1, 2.5:1, 1:1), alone or in the presence of the exemplary scIL-12-HBP FBN (SEQ ID NO:3) immunomodulatory polypeptide described in Example 1 (either at 0.5 ng/mL or 5 ng/mL). Incubation in the presence of target cells without the scIL2 was used as an "untreated" control.

Figure 2:
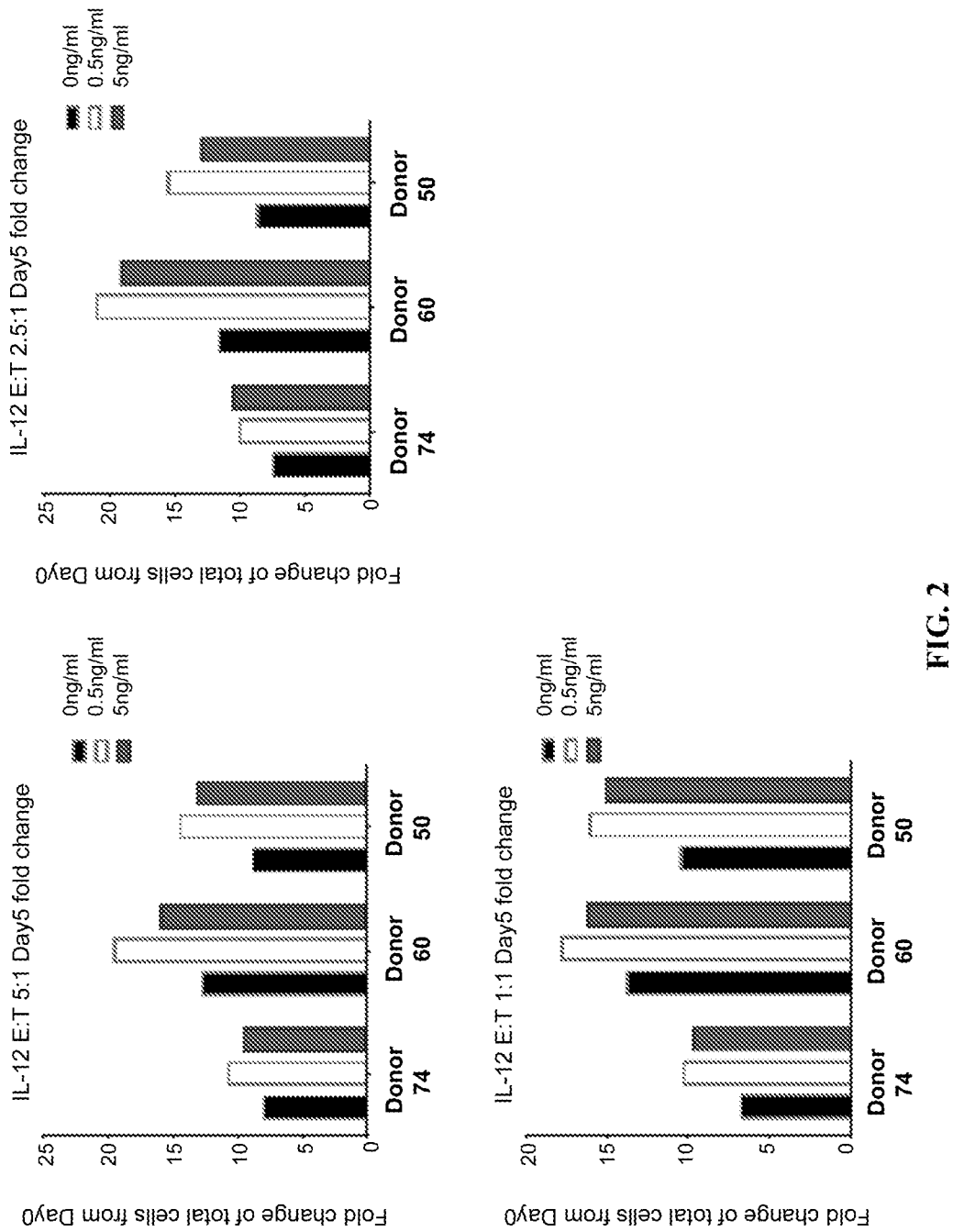
FIG. 2 depicts the fold change in total number of cells following stimulation of cells with the tested IL-12 immunomodulatory protein at various effector target cell ratios.

The fold change in total number of cells at Day 0 prior to stimulation compared to Day 5 post-stimulation was determined. As shown in FIG. 2, a greater increase in cell number was observed in the cells treated in the presence of the scIL-12-HBP FBN, at 0.5 or 5 ng/mL, compared to untreated control cells, at all E:T ratios tested, consistent with the ability of the immunomodulatory polypeptide to enhance cell proliferation and/or survival in the presence of antigen-expressing target cells.

Example 4: T Cell Killing Activity Following Exposure to IL-12 Immunomodulatory Polypeptides CD19-expressing K562-CD19 target cells were co-cultured with anti-CD19-CAR-expressing T cells at various E:T ratios including 5:1, 2.5:1 and 1:1 as described in Example 3. The co-cultures were incubated in the presence of scIL-12-HBP FBN (SEQ ID NO:3) as described in Example 1 at 0.5 or 5 ng/mL or were left untreated. Cell lysis was monitored in real-time over a 0 to about 110-hour time course by adding an IncuCyte™ fluorescent Caspase 3/7 Reagent to the co-cultures to detect cells apoptotic cells. Target cell death was quantitated by automated image analysis over time. The area under the curve (AUC) of fluorescent signal over time for each concentration was determined. A killing index was determined using the formula: 1/AUC.

Figure 3:
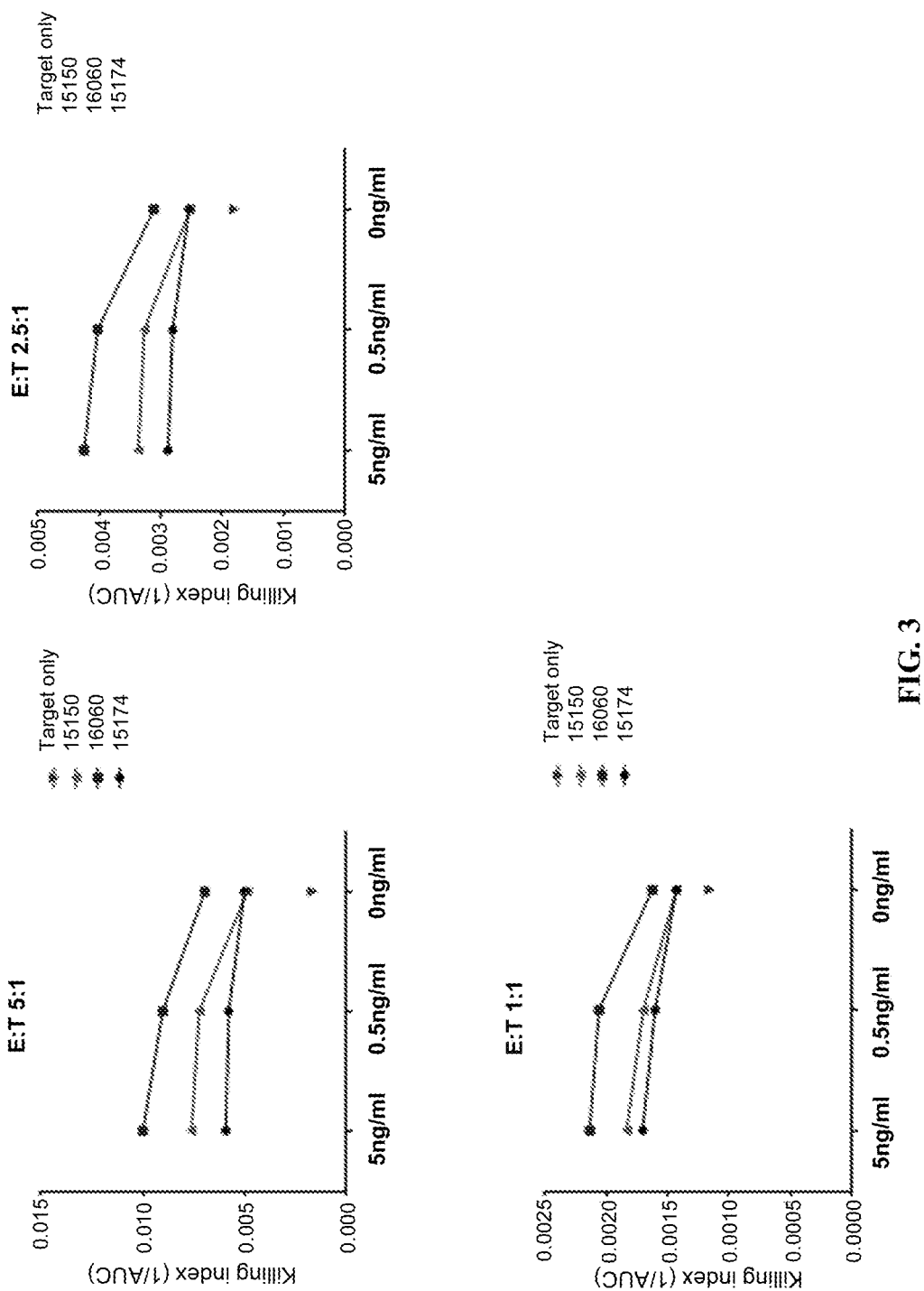
FIG. 3 depicts the killing index of cells following stimulation of cells with the tested IL-12 immunomodulatory protein at various effector target cell ratios.

FIG. 3 sets forth the killing index for each tested condition. As shown in FIG. 3, stimulation of cells in the presence of scIL-12-HBP FBN polypeptides enhanced T cell killing of target cells at all of the E:T ratios as compared to the control, untreated cells.

Example 5: Binding to IL-12 Receptor (IL-12Rb)

Figure 4:
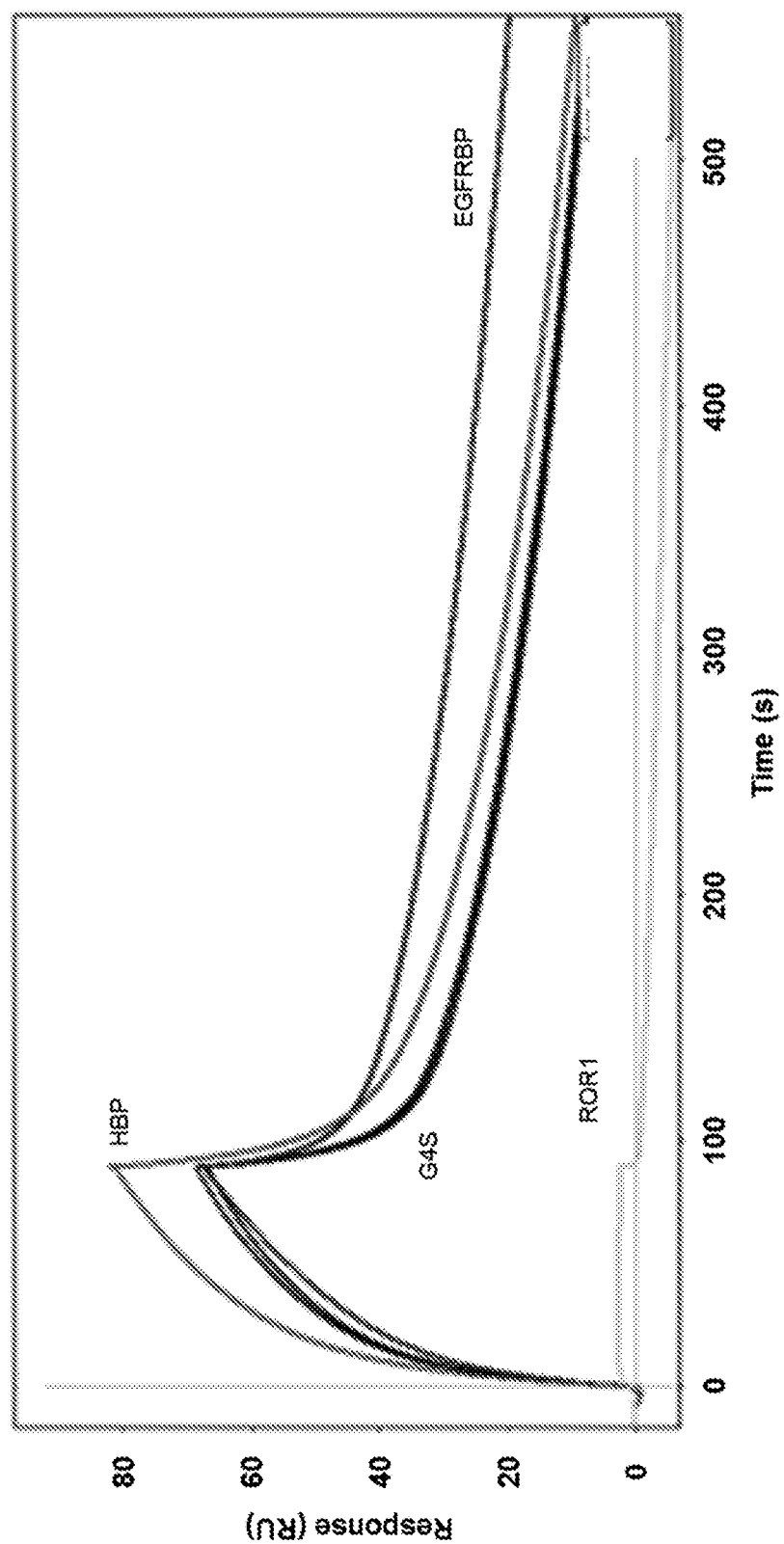
FIG. 4 depicts the binding affinities of IL-12 immunomodulatory proteins as assessed by surface plasmon resonance.

Exemplary single chain IL-12 (scIL-12) immunomodulatory polypeptides, scIL-12-G4S (SEQ ID NO:1), scIL-12-HBP FBN (SEQ ID NO:3), and scIL-12-EGFRBP (SEQ ID NO:5), as described in Example 1, were tested for functional binding to the beta subunit of the IL-12 Receptor (IL-12Rb) by surface plasmon resonance. ROR1-Fc was also assessed for binding to IL-12Rb as a negative control. An anti-hIgG capture chip was used to immobilize IL-12Rb-hIgG1 Fc (purchased from R&D Systems). Approximately 30 nM scIL-12 molecules were flowed over the immobilized IL-12Rb to assess binding using a Biacore surface plasmon resonance instrument. The results are shown in FIG. 4. The results show that scIL-12 containing a linker sequence alone (G4S) or linkers containing a targeting moiety, but not ROR1-Fc, were able to functionally bind to the IL-12 Receptor (IL-12Rb).

Example 6: Binding to Target Molecule-Expressing Cells

Exemplary scIL-12 immunomodulatory polypeptides described in Example 1 are detectably labeled and incubated with target cells known to (or engineered to) express exemplary target molecules (including heparin, EGFR or HGFR), individually capable of being bound by the targeting moiety contained within a given one of the scIL-12 immunomodulatory polypeptides. As controls, the cells also are incubated with control scIL-12 not containing the respective targeting moiety and/or rhIL-12, and/or the scIL-12 containing the targeting moiety is incubated in the presence of cells that do not express the target molecule or motif thereof recognized by the targeting moiety, or do so at lower levels.

Binding is assessed by flow cytometry or other methods as appropriate, and compared between the different conditions; in some aspects, increased binding in the condition involving scIL-12 with a targeting moiety as compared to one or more of the controls, indicates specificity of the engineered single-chain IL-12 reagent for target molecules or motifs recognized by the targeting moiety, further supporting the utility of the scIL-12 in a disease, condition or environment in which the target is or is suspected of being expressed or preferentially expressed.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | Sequence | Name |
|---|---|---|
| 1 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCSGGGGSGGGGSGGGGSRNLPVATPDPGMFPCLHHSQNLL RAVSNMLQKARQTLEFYPCTSEEIDHEDITKDKTSTVEACLPLELTKNES CLNSRETSFITNGSCLASRKTSFMMALCLSSIYEDLKMYQVEFKTMNAKL LMDPKRQIFLDQNMLAVIDELMQALNFNSETVPQKSSLEEPDFYKTKIKL CILLHAFRIRAVTIDRVMSYLNAS | Sc IL-12 G4S(3) |
| 2 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS | Sc IL-12 HBP BMP4 |

| SEQ ID NO. | Sequence | Name |
|---|---|---|
|  | WSEWASVPCSGGGGSRKKNPNCRRHGGGGSRNLPVATPDPGMFPCLHH SQNLLRAVSNMLQKARQTLEFYPCTSEEIDHEDITKDKTSTVEACLPLEL TKNESCLNSRETSFITNGSCLASRKTSFMMALCLSSIYEDLKMYQVEFKT MNAKLLMDPKRQIFLDQNMLAVIDELMQALNFNSETVPQKSSLEEPDFY KTKIKLCILLHAFRIRAVTIDRVMSYLNAS |  |
| 3 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCSGGGGSKNNQKSEPLIGRKKTGGGGSRNLPVATPDPGMFP CLHHSQNLLRAVSNMLQKARQTLEFYPCTSEEIDHEDITKDKTSTVEACL PLELTKNESCLNSRETSFITNGSCLASRKTSFMMALCLSSIYEDLKMYQVE FKTMNAKLLMDPKRQIFLDQNMLAVIDELMQALNFNSETVPQKSSLEEP DFYKTKIKLCILLHAFRIRAVTIDRVMSYLNAS | Sc IL-12 HBP FBN |
| 4 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCSGGGGSVWNWVCFRDVGCDWVLGGGGSRNLPVATPDPG MFPCLHHSQNLLRAVSNMLQKARQTLEFYPCTSEEIDHEDITKDKTSTVE ACLPLELTKNESCLNSRETSFITNGSCLASRKTSFMMALCLSSIYEDLKMY QVEFKTMNAKLLMDPKRQIFLDQNMLAVIDELMQALNFNSETVPQKSSL EEPDFYKTKIKLCILLHAFRIRAVTIDRVMSYLNAS | Sc IL-12 HGFBP |
| 5 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCSGGGGSSVDNPHVCGGGGSRNLPVATPDPGMFPCLHHSQ NLLRAVSNMLQKARQTLEFYPCTSEEIDHEDITKDKTSTVEACLPLELTK NESCLNSRETSFITNGSCLASRKTSFMMALCLSSIYEDLKMYQVEFKTMN AKLLMDPKRQIFLDQNMLAVIDELMQALNFNSETVPQKSSLEEPDFYKT KIKLCILLHAFRIRAVTIDRVMSYLNAS | Sc IL-12 EGFRBP |
| 6 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCSGGGGSQVQLVQSGAEVKKPGSSVKVSCKASGGTFSSYAI SVVVRQAPGQGLEWMGGIIPIFGTANYAQKFQGRVTITADESTSTAYME LSSLRSEDTAVYYCARGLLWNYWGQGTLVTVSSKLSGSASAPKLEEGEF SEARVETTLTQSPATLSVSPGERATLSCRASQSVSSNLAVVYQQKPGQAP RLLIYGASTRATGIPARFSGSGSGTEFTLTISSLQSEDFAVYYCQQYNNWP PGFTFGPGTKVDIKGGGGSRNLPVATPDPGMFPCLHHSQNLLRAVSNML QKARQTLEFYPCTSEEIDHEDITKDKTSTVEACLPLELTKNESCLNSRETS FITNGSCLASRKTSFMMALCLSSIYEDLKMYQVEFKTMNAKLLMDPKRQ IFLDQNMLAVIDELMQALNFNSETVPQKSSLEEPDFYKTKIKLCILLHAFR IRAVTIDRVMSYLNAS | Sc IL-12 Anti EPCAM |
| 7 | GGGGS | G4S linker |
| 8 | GGGGSGGGGS | G4S(2) linker |
| 9 | GGGGSGGGGSGGGGS | G4S(3) linker |
| 10 | RNLPVATPDPGMFPCLHHSQNLLRAVSNMLQKARQTLEFYPCTSEEIDHE DITKDKTSTVEACLPLELTKNESCLNSRETSFITNGSCLASRKTSFMMALC LSSIYEDLKMYQVEFKTMNAKLLMDPKRQIFLDQNMLAVIDELMQALNF NSETVPQKSSLEEPDFYKTKIKLCILLHAFRIRAVTIDRVMSYLNAS | IL-12 p35 UniProt No. P29459 Residues 23-219 |
| 11 | IWELKKDVYVVELDWYPDAPGEMVVLTCDTPEEDGITWTLDQSSEVLG SGKTLTIQVKEFGDAGQYTCHKGGEVLSHSLLLLHKKEDGIWSTDILKD QKEPKNKTFLRCEAKNYSGRFTCWWLTTISTDLTFSVKSSRGSSDPQGVT | IL-12 p40 UniProt No. P29460 residues 23-328 |

| SEQ ID NO. | Sequence | Name |
|---|---|---|
| | CGAATLSAERVRGDNKEYEYSVECQEDSACPAAEESLPIEVMVDAVHKL KYENYTSSFFIRDIIKPDPPKNLQLKPLKNSRQVEVSWEYPDTWSTPHSYF SLTFCVQVQGKSKREKKDRVFTDKTSATVICRKNASISVRAQDRYYSSS WSEWASVPCS | |
| 12 | MCHQQLVISWFSLVFLASPLVA | IL-12p40 signal sequence |
| 13 | RKKNPNCRRH | Heparin binding peptide, BMP4 |
| 14 | KNNQKSEPLIGRKKT | Heparin binding peptide, fibronectin |
| 15 | VWNWVCFRDVGCDWVL | HGF binding peptide |
| 16 | SVDNPHVC | EGFRBP |
| 17 | QVQLVQSGAEVKKPGSSVKVSCKASGGTFSSYAISVVVRQAPGQGLEW MGGIIPIFGTANYAQKFQGRVTITADESTSTAYMELSSLRSEDTAVYYCA RGLLWNYWGQGTLVTVSSKLSGSASAPKLEEGEFSEARVETTLTQSPAT LSVSPGERATLSCRASQSVSSNLAVVYQQKPGQAPRLLIYGASTRATGIP ARFSGSGSGTEFTLTISSLQSEDFAVYYCQQYNNWPPGFTFGPGTKVDIK | Anti-EPCAM scFv |
| 18 | MPLLLLLPLLWAGALAM | CD33 signal sequence |
| 19 | MCPARSLLLVATLVLLDHLSLA | IL-12 p35 signal sequence |
| 20 | HHHHHH | 6x His-tag |
| 21 | WSHPQFEK | Strep-tag® II |
| 22 | KLSGSASAPKLEEGEFSEARV | linker |
| 23 | GSTSGSGKPGSGEGSTKG | linker |
| 24 | QVQLVQSGAEVKKPGSSVKVSCKASGGTFSSYAISVVVRQAPGQGLEW MGGIIPIFGTANYAQKFQGRVTITADESTSTAYMELSSLRSEDTAVYYCA RGLLWNYWGQGTLVTVSS | Anti-EPCAM variable light (VL) |
| 25 | ETTLTQSPATLSVSPGERATLSCRASQSVSSNLAVVYQQKPGQAPRLLIY GASTRATGIPARFSGSGSGTEFTLTISSLQSEDFAVYYCQQYNNWPPGFTF GPGTKVDIK | Anti-EPCAM variable heavy (VH) |
| 26 | ATWLPPR | VEGF binding peptide |
| 27 | ITMQCGIHQGQHPKIRMICEMSF | VEGFR binding peptide |
| 28 | WQPPRARI | bovine origin heparin binding peptide |
| 29 | GGGGS(n) | Linker n is 1 to 5 |
| 30 | GIHVFILGCFSAGLPKTEANWVNVISDLKKIEDLIQSMHIDATLYTESDVH PSCKVTAMKCFLLELQVISLESGDASIHDTVENLIILANNSLSSNGNVTES GCKECEELEEKNIKEFLQSFVHIVQMFINTS | IL-15 Propeptide = amino acids 1-19 |
| 31 | APTSSSTKKTQLQLEHLLLDLQMILNGINNYKNPKLTRMLTFKFYMPKK ATELKHLQCLEEELKPLEEVLNLAQSKNFHLRPRDLISNINVIVLELKGSE TTFMCEYADETATIVEFLNRWITFCQSIISTLT | IL-2 |
| 32 | MAAEPVEDNCINFVAMKFIDNTLYFIAEDDENLESDYFGKLESKLSVIRN LNDQVLFIDQGNRPLFEDMTDSDCRDNAPRTIFIISMYKDSQPRGMAVTI SVKCEKISTLSCENKIISFKEMNPPDNIKDTKSDIIFFQRSVPGHDNKMQFE SSSYEGYFLACEKERDLFKLILKKEDELGDRSIMFTVQNED | IL-19 Propeptide = amino acids 1-36 |

-continued

| SEQ ID NO. | Sequence | Name |
|---|---|---|
| 33 | APARSPSPSTQPWEHVNAIQEARRLLNLSRDTAAEMNETVEVISEMFDLQ EPTCLQTRLELYKQGLRGSLTKLKGPLTMMASHYKQHCPPTPETSCATQI ITFESFKENLKDFLLVIPFDCWEPVQE | GM-CSF |
| 34 | DCDIEGKDGKQYESVLMVSIDQLLDSMKEIGSNCLNNEFNFFKRHICDAN KEGMFLFRAARKLRQFLKMNSTGDFDLHLLKVSEGTTILLNCTGQVKGR KPAALGEAQPTKSLEENKSLKEQKKLNDLCFLKRLLQEIKTCWNKILMG TKEH | IL-7 |
| 35 | QGQDRHMIRMRQLIDIVDQLKNYVNDLVPEFLPAPEDVETNCEWSAFSC FQKAQLKSANTGNNERIINVSIKKLKRKPPSTNAGRRQKHRLTCPSCDSY EKKPPKEFLERFKSLLQKMIHQHLSSRTHGSEDS | IL-21 |
| 36 | CDLPETHSLDNRRTLMLLAQMSRISPSSCLMDRHDFGFPQEEFDGNQFQ KAPAISVLHELIQQIFNLFTTKDSSAAWDEDLLDKFCTELYQQLNDLEAC VMQEERVGETPLMNADSILAVKKYFRRITLYLTEKKYSPCAWEVVRAEI MRSLSLSTNLQERLRRKE | IFN alpha-1/13 |
| 37 | CDLPQTHSLGSRRTLMLLAQMRKISLFSCLKDRHDFGFPQEEFGNQFQK AETIPVLHEMIQQIFNLFSTKDSSAAWDETLLDKFYTELYQQLNDLEACVI QGVGVTETPLMKEDSILAVRKYFQRITLYLKEKKYSPCAWEVVRAEIMR SFSLSTNLQESLRSKE | IFN alpha-2 |
| 38 | CDLPQTHSLGNRRALILLAQMGRISHFSCLKDRHDFGFPEEEFDGHQFQK AQAISVLHEMIQQTFNLFSTEDSSAAWEQSLLEKFSTELYQQLNDLEACV IQEVGVEETPLMNEDSILAVRKYFQRITLYLTEKKYSPCAWEVVRAEIMR SLSFSTNLQKRLRRKD | IFN alpha-4 |
| 39 | LGCDLPQTHSLSNRRTLMIMAQMGRISPFSCLKDRHDFGFPQEEFDGNQF QKAQAISVLHEMIQQTFNLFSTKDSSATWDETLLDKFYTELYQQLNDLE ACMMQEVGVEDTPLMNVDSILTVRKYFQRITLYLTEKKYSPCAWEVVR AEIMRSFSLSANLQERLRRKE | IFN alpha-5 |
| 40 | SLDCDLPQTHSLGHRRTMMLLAQMRRISLFSCLKDRHDFRFPQEEFDGN QFQKAEAISVLHEVIQQTFNLFSTKDSSVAWDERLLDKLYTELYQQLNDL EACVMQEVWVGGTPLMNEDSILAVRKYFQRITLYLTEKKYSPCAWEVV RAEIMRSFSSSRNLQERLRRKE | IFN alpha-6 |
| 41 | CDLPQTHSLRNRRALILLAQMGRISPFSCLKDRHEFRFPEEEFDGHQFQKT QAISVLHEMIQQTFNLFSTEDSSAAWEQSLLEKFSTELYQQLNDLEACVI QEVGVEETPLMNEDFILAVRKYFQRITLYLMEKKYSPCAWEVVRAEIMR SFSFSTNLKKGLRRKD | IFN alpha-7 |
| 42 | CDLPQTHSLGNRRALILLAQMRRISPFSCLKDRHDFEFPQEEFDDKQFQK AQAISVLHEMIQQTFNLFSTKDSSAALDETLLDEFYIELDQQLNDLESCV MQEVGVIESPLMYEDSILAVRKYFQRITLYLTEKKYSSCAWEVVRAEIMR SFSLSINLQKRLKSKE | IFN alpha-8 |
| 43 | CDLPQTHSLGNRRALILLGQMGRISPFSCLKDRHDFRIPQEEFDGNQFQK AQAISVLHEMIQQTFNLFSTEDSSAAWEQSLLEKFSTELYQQLNDLEACV IQEVGVEETPLMNEDSILAVRKYFQRITLYLIERKYSPCAWEVVRAEIMRS LSFSTNLQKRLRRKD | IFN alpha-10 |
| 44 | CNLSQTHSLNNRRTLMLMAQMRRISPFSCLKDRHDFEFPQEEFDGNQFQ KAQAISVLHEMMQQTFNLFSTKNSSAAWDETLLEKFYIELFQQMNDLEA CVIQEVGVEETPLMNEDSILAVKKYFQRITLYLMEKKYSPCAWEVVRAEI MRSLSFSTNLQKRLRRKD | IFN alpha-14 |
| 45 | CDLPQTHSLGNRRALILLAQMGRISHFSCLKDRYDFGFPQEVFDGNQFQK AQAISAFHEMIQQTFNLFSTKDSSAAWDETLLDKFYIELFQQLNDLEACV TQEVGVEEIALMNEDSILAVRKYFQRITLYLMGKKYSPCAWEVVRAEIM RSFSFSTNLQKGLRRKD | IFN alpha-16 |
| 46 | CDLPQTHSLGNRRALILLAQMGRISPFSCLKDRHDFGLPQEEFDGNQFQK TQAISVLHEMIQQTFNLFSTEDSSAAWEQSLLEKFSTELYQQLNNLEACVI QEVGMEETPLMNEDSILAVRKYFQRITLYLTEKKYSPCAWEVVRAEIMR SLSFSTNLQKILRRKD | IFN alpha-17 |
| 47 | CDLPQTHSLGNRRALILLAQMGRISPFSCLKDRHDFGFPQEEFDGNQFQK AQAISVLHEMIQQTFNLFSTEDSSATWEQSLLEKFSTELNQQLNDLEACV IQEVGVEETPLMNVDSILAVKKYFQRITLYLTEKKYSPCAWEVVRAEIMR SFSLSKIFQERLRRKE | IFN alpha-21 |

SEQUENCES

| SEQ ID NO. | Sequence | Name |
|---|---|---|
| 48 | MSYNLLGFLQRSSNFQCQKLLWQLNGRLEYCLKDRMNFDIPEEIKQLQQ FQKEDAALTIYEMLQNIFAIFRQDSSSTGWNETIVENLLANVYHQINHLK TVLEEKLEKEDFTRGKLMSSLHLKRYYGRILHYLKAKEYSHCAWTIVRV EILRNFYFINRLTGYLRN | IFN beta-1 |
| 49 | QDPYVKEAENLKKYFNAGHSDVADNGTLFLGILKNWKEESDRKIMQSQI VSFYFKLFKNFKDDQSIQKSVETIKEDMNVKFFNSNKKKRDDFEKLTNY SVTDLNVQRKAIHELIQVMAELSPAAKTGKRKRSQMLFRGRRASQ | IFN gamma |
| 50 | GITIPRNPGCPNSEDKNFPRTVMVNLNIHNRNTNTNPKRSSDYYNRSTSP WNLHRNEDPERYPSVIWEAKCRHLGCINADGNVDYHMNSVPIQQEILVL RREPPHCPNSFRLEKILVSVGCTCVTPIVHHVA | IL-17A |
| 51 | RKIPKVGHTFFQKPESCPPVPGGSMKLDIGIINENQRVSMSRNIESRSTSP WNYTVTWDPNRYPSEVVQAQCRNLGCINAQGKEDISMNSVPIQQETLV VRRKHQGCSVSFQLEKVLVTVGCTCVTPVIHHVQ | IL-17F |
| 52 | RAVPGGSSPAWTQCQQLSQKLCTLAWSAHPLVGHMDLREEGDEETTND VPHIQCGDGCDPQGLRDNSQFCLQRIHQGLIFYEKLLGSDIFTGEPSLLPD SPVGQLHASLLGLSQLLQPEGHHWETQQIPSLSPSQPWQRLLLRFKILRSL QAFVAVAARVFAHGAATLSP | IL-23 alpha (p19) |
| 53 | APMTQTTPLKTSWVNCSNMIDEIITHLKQPPLPLLDFNNLNGEDQDILME NNLRRPNLEAFNRAVKSLQNASAIESILKNLLPCLPLATAAPTRHPIHIKD GDWNEFRRKLTFYLKTLENAQAQQTTLSLAIF | IL-3 |
| 54 | HKCDITLQEIIKTLNSLTEQKTLCTELTVTDIFAASKNTTEKETFCRAATVL RQFYSHHEKDTRCLGATAQQFHRHKQLIRFLKRLDRNLWGLAGLNSCPV KEANQSTLENFLERLKTIMREKYSKCSS | IL-4 |
| 55 | IPTEIPTSALVKETLALLSTHRTLLIANETLRIPVPVHKNHQLCTEEIFQGIG TLESQTVQGGTVERLFKNLSLIKKYIDGQKKKCGEERRRVNQFLDYLQEF LGVMNTEWIIES | IL-5 |
| 56 | VPPGEDSKDVAAPHRQPLTSSERIDKQIRYILDGISALRKETCNKSNMCES SKEALAENNLNLPKMAEKDGCFQSGFNEETCLVKIITGLLEFEVYLEYLQ NRFESSEEQARAVQMSTKVLIQFLQKKAKNLDAITTPDPTTNASLLTKLQ AQNQWLQDMTTHLILRSFKEFLQSSLRALRQM | IL-6 |
| 57 | QGCPTLAGILDINFLINKMQEDPASKCHCSANVTSCLCLGIPSDNCTRPCF SERLSQMTNTTMQTRYPLIFSRVKKSVEVLKNNKCPYFSCEQPCNQTTA GNALTFLKSLLEIFQKEKMRGMRGKI | IL-9 |
| 58 | PGPPPGPPRVSPDPRAELDSTVLLTRSLLADTRQLAAQLRDKFPADGDHN LDSLPTLAMSAGALGALPGVLTRLRADLLSYLRHVQWLRRAGGSSLK TLEPELGTLQARLDRLLRRLQ LLMSRLALPQPPPDPPAPPLAPPSSAWGGIRAAHAILGGLHLTLDWAVRG LLLLKTRL | IL-11 |
| 59 | LTCLGGFASPGPVPPSTALRELIEELVNITQNQKAPLCNGSMVWSINLTAG MYCAALESLINVSGCSAIEKTQRMLSGFCPHKVSAGQFSSLHVRDTKIEV AQFVKDLLLHLKKLFREGRFN | IL-13 |
| 60 | FPRPPGRPQLSQELRREFTVSLHLARKLLSEVRGQAHRFAESHLPGVNL YLLPLGEQLPDVSLTFQAWRRLSDPERLCFISTTLQPFHALLGGLGTQGR WTNMERMQLWAMRLDLRDLQRHLRFQVLAAGFNLPEEEEEEEEEEEE RKGLLPGALGSALQGPAQVSWPQLLSTYRLLHSLELVLSRAVRELLLLSK AGHSVWPLGFPTLSPQP | IL-27 alpha (p28) |
| 61 | RKGPPAALTLPRVQCRASRYPIAVDCSWTLPPAPNSTSPVSFIATYRLGM AARGHSWPCLQQTPTSTSCTITDVQLFSMAPYVLNVTAVHPWGSSSSFV PFITEHIIKPDPPEGVRLSPLAERQLQVQWEPPGSWPFPEIFSLKYWIRYKR QGAARFHRVGPIEATSFILRAVRPRARYYVQVAAQDLTDYGELSDWSLP ATATMSLGK | IL-27 beta (EBI3), IL-35 beta |
| 62 | APPRLICDSRVLERYLLEAKEAENITTGCAEHCSLNENITVPDTKVNFYA WKRMEVGQQAVEVWQGLALLSEAVLRGQALLVNSSQPWEPLQLHVDK AVSGLRSLTTLLRALGAQKEAISPPDAASAAPLRTITADTFRKLFRVYSNF LRGKLKLYTGEACRTGDR | Erythropoietin |

-continued

| SEQ ID NO. | Sequence | Name |
|---|---|---|
| 63 | ATPLGPASSLPQSFLLKCLEQVRKIQGDGAALQEKLVSECATYKLCHPEE LVLLGHSLGIPWAPLSSCPSQALQLAGCLSQLHSGLFLYQGLLQALEGISP ELGPTLDTLQLDVADFATTIWQQMEELGMAPALQPTQGAMPAFASAFQ RRAGGVLVASHLQSFLEVSYRVLRHLAQP | G-CSF |
| 64 | FPTIPLSRLFDNAMLRAHRLHQLAFDTYQEFEEAYIPKEQKYSFLQNPQTS LCFSESIPTPSNREETQQKSNLELLRISLLLIQSWLEPVQFLRSVFANSLVY GASDSNVYDLLKDLEEG IQTLMGRLEDGSPRTGQIFKQTYSKFDTNSHNDDALLKNYGLLYCFRKD MDKVETFLRIVQCRSVEGSCGF | Growth hormone |
| 65 | LPICPGGAARCQVTLRDLFDRAVVLSHYIHNLSSEMFSEFDKRYTHGRGF ITKAINSCHTSSLATPEDKEQAQQMNQKDFLSLIVSILRSWNEPLYHLVTE VRGMQEAPEAILSKAVEIEEQTKRLLEGMELIVSQVHPETKENEIYPVWS GLPSLQMADEESRLSAYYNLLHCLRRDSHKIDNYLKLLKCRIIHNNNC | Prolactin |
| 66 | AAIGSCSKEYRVLLGQLQKQTDLMQDTSRLLDPYIRIQGLDVPKLREHCR ERPGAFPSEETLRGLGRRGFLQTLNATLGCVLHRLADLEQRLPKAQDLER SGLNIEDLEKLQMARPNILGLRNNIYCMAQLLDNSDTAEPTKAGRGASQ PPTPTPASDAFQRKLEGCRFLHGYHRFMHSVGRVFSKWGESPNRSRRHS PHQALRKGVRRTRPSRKGKRLMTRGQLPR | Oncostatin M |
| 67 | SPLPITPVNATCAIRHPCHNNLMNQIRSQLAQLNGSANALFILYYTAQGEP FPNNLDKLCGPNVTDFPPFHANGTEKAKLVELYRIVVYLGTSLGNITRDQ KILNPSALSLHSKLNATADILRGLLSNVLCRLCSKYHVGHVDVTYGPDTS GKDVFQKKKLGCQLLGKYKQIIAVLAQAF | Leukemia inhibitory factor |
| 68 | APISSHCRLDKSNFQQPYITNRTFMLAKEASLADNNTDVRLIGEKLFHGV SMSERCYLMKQVLNFTLEEVLFPQSDRFQPYMQEVVPFLARLSNRLSTC HIEGDDLHIQRNVQKLKDTVKKLGESGEIKAIGELDLLFMSLRNACI | IL-22 |
| 69 | SPGQGTQSENSCTHFPGNLPNMLRDLRDAFSRVKTFFQMKDQLDNLLLK ESLLEDFKGYLGCQALSEMIQFYLEEVMPQAENQDPDIKAHVNSLGENL KTLRLRLRRCHRFLPCENKSKAVEQVKNAFNKLQEKGIYKAMSEFDIFIN YIEAYMTMKIRN | IL-10 |
| 70 | ESKYGPPCPPCP | spacer (IgG4hinge) |
| 71 | GAATCTAAGTACGGACCGCCCTGCCCCCCTTGCCCT | spacer (IgG4hinge) |
| 72 | ESKYGPPCPPCPGQPREPQVYTLPPSQEEMTKNQVSLTCLVKGFYPSDIA VEWESNGQPENNYKTTPPVLDSDGSFFLYSRLTVDKSRWQEGNVFSCSV MHEALHNHYTQKSLSLSLGK | Hinge-CH3 spacer |
| 73 | ESKYGPPCPPCPAPEFLGGPSVFLFPPKPKDTLMISRTPEVTCVVVDVSQE DPEVQFNWYVDGVEVHNAKTKPREEQFNSTYRVVSVLTVLHQDWLNG KEYKCKVSNKGLPSSIEKTISKAKGQPREPQVYTLPPSQEEMTKNQVSLT CLVKGFYPSDIAVEWESNGQPENNYKTTPPVLDSDGSFFLYSRLTVDKSR WQEGNVFSCSVMHEALHNHYTQKSLSLSLGK | Hinge-CH2-CH3 spacer |
| 74 | RWPESPKAQASSVPTAQPQAEGSLAKATTAPATTRNTGRGGEEKKKEKE KEEQEERETKTPECPSHTQPLGVYLLTPAVQDLWLRDKATFTCFVVGSD LKDAHLTWEVAGKVPTGGVEEGLLERHSNGSQSQHSRLTLPRSLWNAG TSVTCTLNHPSLPPQRLMALREPAAQAPVKLSLNLLASSDPPEAASWLLC EVSGFSPPNILLMWLEDQREVNTSGFAPARPPPQPGSTTFWAWSVLRVPA PPSPQPATYTCVVSHEDSRTLLNASRSLEVSYVTDH | IgD-hinge-Fc |
| 75 | MLLLVTSLLLCELPHPAFLLIPRKVCNGIGIGEFKDSLSINATNIKHFKNCT SISGDLHILPVAFRGDSFTHTPPLDPQELDILKTVKEITGFLLIQAWPENRT DLHAFENLEIIRGRTKQHGQFSLAVVSLNITSLGLRSLKEISDGDVIISGNK NLCYANTINWKKLFGTSGQKTKIISNRGENSCKATGQVCHALCSPEGCW GPEPRDCVSCRNVSRGRECVDKCNLLEGEPREFVENSECIQCHPECLPQA MNITCTGRGPDNCIQCAHYIDGPHCVKTCPAGVMGENNTLVWKYADAG HVCHLCHPNCTYGCTGPGLEGCPTNGPKIPSIATGMVGALLLLLVALGI GLFM | tEGFR |
| 76 | LEGGGEGRGSLLTCGDVEENPGPR | T2A |
| 77 | FWVLVVVGGVLACYSLLVTVAFIIFWV | CD28 (amino acids 153-179 of Accession No. P10747) |

| SEQ ID NO. | Sequence | Name |
|---|---|---|
| 78 | IEVMYPPPYLDNEKSNGTIIHVKGKHLCPSPLFPGPSKP FWVLVVVGGVLACYSLLVTVAFIIFWV | CD28 (amino acids 114-179 of Accession No. P10747) |
| 79 | RSKRSRLLHSDYMNMTPRRPGPTRKHYQPYAPPRDFAAYRS | CD28 (amino acids 180-220 of P10747) |
| 80 | RSKRSRGGHSDYMNMTPRRPGPTRKHYQPYAPPRDFAAYRS | CD28 (LL to GG) |
| 81 | KRGRKKLLYIFKQPFMRPVQTTQEEDGCSCRFPEEEEGGCEL | 4-1BB (amino acids 214-255 of Q07011.1) |
| 82 | RVKFSRSADAPAYQQGQNQLYNELNLGRREEYDVLDKRRGRDPEMGG KPRRKNPQEGLYNELQKDKMAEAYSEIGMKGERRRGKGHDGLY QGLSTATKDTYDALHMQALPPR | CD3 zeta |
| 83 | RVKFSRSAEPPAYQQGQNQLYNELNLGRREEYDVLDKRRGRDPEMGGK PRRKNPQEGLYNELQKDKMAEAYSEIGMKGERRRGKGHDGLY QGLSTATKDTYDALHMQALPPR | CD3 zeta |
| 84 | RVKFSRSADAPAYKQGQNQLYNELNLGRREEYDVLDKRRGRDPEMGG KPRRKNPQEGLYNELQKDKMAEAYSEIGMKGERRRGKGHDGLY QGLSTATKDTYDALHMQALPPR | CD3 zeta |
| 85 | gccctacgtgctgtctcacacagcctgtctgac | Epo HRE |
| 86 | ccacagtgcatacgtgggctccaacaggtcctctt | VEGF-A HRE |
| 87 | gacgtgacaaacgaagccgacgtc | PGK1 HRE |
| 88 | acacgtgggttcccgcacgtccgc | LdhA HRE |
| 89 | gacgtgactcggaccacat | ALDA HRE |
| 90 | gcccacacgctcggtgcgtgcccagttgaac | GAPDH HRE |
| 91 | ccttatttgg | Exemplary CArG motif |
| 92 | cgcgtgatatccttatttggccttatttggccttatttggccttatttgg | Synthetic CArG sequence-containing promoter |
| 93 | cgcgtgatatccttatttggccttatttggccttatttggccttatttgg ccttatttggccttatttgg | Synthetic CArG sequence-containing promoter |
| 94 | cgcgtgatatccttatttggccttatttggccttatttggccttatttgg ccttatttggccttatttggccttatttggccttatttgg | Synthetic CArG sequence-containing promoter |
| 95 | cgcgtgatatccttatttggccttatttggccttatttggccttatttgg ccttatttggccttatttggccttatttggccttatttggccttatttgg ccttatttgg | Synthetic CArG sequence-containing promoter |
| 96 | EGRGSLLTCGDVEENPGP | T2A |
| 97 | GSGATNFSLLKQAGDVEENPGP | P2A |
| 98 | ATNFSLLKQAGDVEENPGP | P2A |
| 99 | QCTNYALLKLAGDVESNPGP | E2A |
| 100 | VKQTLNFDLLKLAGDVESNPGP | F2A |
| 101 | RKVCNGIGIGEFKDSLSINATNIKHFKNCTSISGDLHILPVAFRGDSFTHTP PLDPQELDILKTVKEITGFLLIQAWPENRTDLHAFENLEIIRGRTKQHGQF SLAVVSLNITSLGLRSLKEISDGDVIISGNKNLCYANTINWKKLFGTSGQK TKIISNRGENSCKATGQVCHALCSPEGCWGPEPRDCVSCRNVSRGRECV DKCNLLEGEPREFVENSECIQCHPECLPQAMNITCTGRGPDNCIQCAHYI DGPHCVKTCPAGVMGENNTLVWKYADAGHVCHLCHPNCTYGCTGPGL EGCPTNGPKIPSIATGMVGALLLLLVVALGIGLFM | tEGFR |

-continued

| SEQ ID NO. | Sequence | Name |
|---|---|---|
| 102 | gctagcgccaccatgcccctgctgctgctgctgcctctgctgtgggctgg cgcactggccatctgggagctgaagaaagacgtgtacgtggtcgaactgg actggtatcctgatgccccaggagagatggtggtcctgacttgcgacacc cccgaggaagatggcatcacttggaccctggatcagagctccgaggtgct gggaagcggcaaaacactgactattcaggtcaaggaattcggggacgctg gacagtacacatgtcacaagggaggagaggtgctgagccactccctgctg ctgctgcataagaaagaagacggcatctggagcactgacattctgaaaga tcagaaggagccaaagaacaaaaccttcctgcgctgcgaagcaaaaaatt atagcggccggttcacctgttggtggctgaccacaatcagcacagatctg acttttccgtgaagtctagtagggggtcaagcgacccacagggagtcac atgcggagcagctactctgtccgccgagcgggtgagaggagataacaagg agtacgaatattcagtcgagtgccaggaagacagcgcatgtcctgcagcc gaggaatctctgccaatcgaagtgatggtcgatgccgtgcacaagctgaa atacgaaaactacacatcctctttctttatccgagacatcatcaagccag atcccctaagaacctgcagctgaaaccctgaagaattctcgccaggtg gaggtcagttgggaatacccagacacctggagcacaccccattcatattt cagcctgacttttgcgtgcaggtccagggcaagagtaaaagagagaaga aagacagggtgttcactgataaaaccagcgccacagtcatctgtcggaag aacgcctctattagtgtgcgagctcaggatcggtactatagttcaagctg gtccgaatgggcttctgtgccttgtagtggaggaggaggaagcggaggag gaggatccggaggaggcgggtctagaaatctgcctgtggcaaccccagac cccggcatgttcccatgcctgcaccattcccagaacctgctgcgggcagt gtctaatatgctgcagaaggccagacagaccctggagttttacccctgta catccgaggaaatcgaccacgaggatattaccaaggataaaaacctctaca gtggaagcttgcctgcctctggagctgacaaagaacgaatcatgtctgaa tagcagggagacttccttcatcaccaacggctcttgcctggccagtcgca agaccagcttcatgatggctctgtgcctgtcctct atctacgaggacctgaagatgtatcaggtggaattcaaaaccatgaacgccaagctgctgatgga ccctaaaaggcagatcttctctggatcagaatatgctggctgtgattgacg agctgatgcaggcactgaacttcaatagcgaaacagtccccagaagagt tcactggaggaacctgatttctacaagactaaaatcaagctgtgcattct gctgcacgcttttaggatccgcgcagtgaccattgaccgcgtcatgagtt atctgaatgcctcacaccatcaccattggtcccatccacagttt gagaagtgataactcgag | Sc IL-12 G4S(3) |
| 103 | gctagcgccaccatgcccctgctgctgctgctgcctctgctgtgggctgg cgcactggccatctgggagctgaagaaagacgtgtacgtggtcgaactgg actggtatcctgatgccccaggggagatggtggtcctgacttgcgacacc cccgaggaagatggaatcacttggaccctggatcagagctccgaggtgct ggggtccggaaaaacactgactattcaggtcaaggaattcggggacgctg ggcagtacacatgtcacaagggaggagaggtgctgagccactccctgctg ctgctgcataagaaagaagacggaatctggtctactgacattctgaaaga tcagaaggagcctaagaacaaaaccttcctgcggtgcgaagcaaaaaatt atagcggccggttcacctgttggtggctgaccacaatctctacagatctg acttttagtgtgaagtctagtagggggtcaagcgacccacagggagtcac atgcggagcagctactctgagcgccgagagggtgcgcggggataacaagg agtacgaatattccgtcgagtgccaggaagactctgcatgtcctgcagcc gaggaatccctgccaatcgaagtgatggtcgatgccgtgcacaagctgaa atacgaaaactacacatcctctttctttatagggacatcatcaagccag atcccctaagaacctgcagctgaaaccctgaagaattcacgccaggtg gaggtcagctgggaatacccagacacctggagcacaccccattcatattt cagcctgacttttgcgtgcaggtccagggcaagagcaaacgcgagaga aagaccgagtgttcactgataaaacctccgctacagtcatctgccgcaag aacgcctctattagtgtgagagctcaggataggtactatagttcaagctg gtccgaatgggcatctgtgccatgcagtggaggaggaggaagccggaaga aaaaccctaattgtcggagacacggcggggaggctccagaaatctgcct gtggctaccccagaccccgggatgttcccatgcctgcaccatagtcagaa cctgctgagggcagtgtcaaatatgctgcagaaggcccgccagaccctgg agttttacccatgtacatctgaggaaatcgaccacgaggatattaccaag gataaaaccagtacagtggaagcctgcctgcccctggagctgacaaagaa cgaatcatgtctgaatagccgagagacttccttcatcaccaacggctctt gcctggccagtcgcaagaccagcttcatgatggctctgtgcctgtcctct atctacgaggacctgaagatgtatcaggtggaattcaaaaccatgaacgc caagctgctgatggaccccaaacggcagatcttctctggatcagaatatgc tggctgtgattgacgagctgatgcaggcactgaacttcaattctgaaaca gtccccagaagagttcactggaggaacctgatttctacaagactaaaat caagctgtgcattctgctgcacgcttttgaatccgggcagtgaccattg acagagtcatgagctatctgaatgcctccaccatcaccatcaccattgg agccatcctcagtttgagaagtgataactcgag | Sc IL-12 HBP BMP4 |
| 104 | gctagcgccaccatgcccctgctgctgctgctgcctctgctgtgggctgg cgcactggccatctgggagctgaagaaagacgtgtacgtggtcgaactgg | Sc IL-12 HBP FBN |

| SEQ ID NO. | Sequence | Name |
|---|---|---|
|  | actggtatcctgatgccccaggggagatggtggtcctgacttgcgacacc<br>cccgaggaagatggaatcacttggaccctggatcagagctccgaggtgct<br>ggggagcggaaaaacactgactattcaggtcaaggaattcggcgacgctg<br>ggcagtacacatgtcacaagggaggagaggtgctgagccactccctgctg<br>ctgctgcataagaaagaagacgggatctggtctacagacattctgaaaga<br>tcagaaggagcctaagaacaaaactttcctgcgctgcgaagcaaaaaatt<br>atagcggccggttcacctgttggtggctgaccacaatctctacagatctg<br>acttttagtgtgaagtctagtaggggatcaagcgacccacagggagtcac<br>atgcggagcagctactctgagcgccgagcgggtgagaggcgataacaagg<br>agtacgaatatagtgtcgagtgccaggaagactcagcatgtcctgcagcc<br>gaggaatccctgccaatcgaagtgatggtcgatgccgtgcacaagctgaa<br>atacgaaaactacacatcctcttctcttattcgggacatcatcaagccag<br>atccccctaagaacctgcagctgaaacccctgaagaattcaagacaggtg<br>gaggtcagctgggaatacccagacacctggtccacacccattcatattt<br>cagcctgaccttttgcgtgcaggtccagggcaagtctaaaagagagaaga<br>aagacagggtgttcactgataaaaccagtgctacagtcatctctgagaaag<br>aacgcctctattagtgtgcgagctcaggatcggtactatagttcaagctg<br>gtccgagtgggcatctgtgccctgtagtggaggcggggatccaaaaaca<br>atcagaagtctgaacctctgatcggccggaagaaaactggcggggggaggc<br>agcagaaatctgcctgtggctaccccagatcccggatgttcccatgcct<br>gcaccatagccagaacctgctgagggcagtgtccaatatgctgcagaagg<br>cccgccagaccctggagttttacccatgtacaagcgaggaaatcgaccac<br>gaggatattactaaggacaaaacctccacagtggaagcctgcctgcccct<br>ggagctgaccaagaacgaatcatgtctgaatagccgagagacttccttca<br>tcaccaacggctcttgcctggccagtcgcaagaccagcttcatgatggct<br>ctgtgcctgtcctctatctacgaggacctgaagatgtatcaggtggaatt<br>caaaactatgaacgccaagctgctgatggaccccaaaaggcagatctttc<br>tggatcagaatatgctggctgtgattgacgagctgatgcaggcactgaa<br>ttcaattctgaaaccgtcccccagaagagttcactggaggaacctgattt<br>ctacaagacaaaaatcaagctgtgcattctgctgcacgcttttaggatcc<br>gcgcagtgaccattgaccgcgtcatgagctatctgaatgcctcccaccat<br>caccatcaccattggagccatcctcagtttgagaagtgataactcgag |  |
| 105 | gctagcgccaccatgcccctgctgctgctgctgcctctgctgtgggctgg<br>cgcactggccatctgggagctgaagaaagacgtgtacgtggtcgaactgg<br>actggtatcctgatgccccaggggagatggtggtcctgacttgcgacacc<br>cccgaggaagatggaatcacttggaccctggatcagagctccgaggtgct<br>ggggtccggaaaaacactgactattcaggtcaaggaattcggcgacgctg<br>ggcagtacacatgtcacaagggaggagaggtgctgagccactccctgctg<br>ctgctgcataagaaagaagacgggatctggtctactgacattctgaaaga<br>tcagaaggagccaaagaacaaaaccttcctgcgctgcgaagcaaaaaatt<br>atagcggccggttcacctgttggtggctgaccacaatctctacagatctg<br>acttttagtgtgaagtctagtaggggctcaagcgacccacagggagtcac<br>atgcggagcagctactctgagcgccgagcgggtgagaggggataacaagg<br>agtacgaatattccgtcgagtgccaggaagactctgcatgtcctgcagcc<br>gaggaatccctgccaatcgaagtgatggtcgatgccgtgcacaagctgaa<br>atacgaaaactacacatcctctttctttattcgggacatcatcaagccag<br>atccccctaagaacctgcagctgaaacccctgaagaattcaagacaggtg<br>gaggtcagctgggaatacccagacacctggagcacacccattcatattt<br>cagcctgactttttgcgtgcaggtccagggcaagagcaaaagagagaaga<br>aagacagggtgttcactgataaaacctccgctacagtcatctgcagaaag<br>aacgcctctattagtgtgcgagctcaggatcggtactatagttcaagctg<br>gtccgaatgggcatctgtgccttgtagtggaggcggggaagcgtgtgga<br>actgggctgctttagggacgtgggatgtgattgggtcctgggaggagga<br>ggctcccgcaatctgcctgtggctaccccagatcccggcatgttcccatg<br>cctgcaccatagtcagaacctgctgcgggcagtgtcaaatatgctgcaga<br>aggccagacagaccctggagttttaccctgtacatctgaggaaatcgac<br>cacgaggatattaccaaggacaaaaccagtacagtggaagcctgcctgcc<br>tctggagctgacaaagaacgaatcatgtctgaatagccgagagacttcct<br>tcatcaccaacggctcttgcctggccagtcgcaagaccagcttcatgatg<br>gctctgtgcctgtcctctatctacgaggacctgaagatgtatcaggtgga<br>attcaaaaccatgaacgccaagctgctgatgaccctaaaaggcagatct<br>ttctggatcagaatatgctggctgtgattgacgagctgatgcaggcactg<br>aacttcaattctgaaacagtgccccagaagagttcactggaggaacctga<br>tttctacaagactaaaatcaagctgtgcattctgctgcacgcttttagga<br>tccgcgcagtgaccattgaccgcgtcatgagctatctgaatgcctcccac<br>catcaccatcaccattggagccatccacagtttgagaagtgataactcga<br>g | Sc IL-12 HGFBP |
| 106 | gctagcgccaccatgcccctgctgctgctgctgcctctgctgtgggctgg<br>cgcactggccatctgggagctgaagaaagacgtgtacgtggtcgaactgg<br>actggtatcctgatgccccaggggagatggtggtcctgacttgcgacacc<br>cccgaggaagatggaatcacttggaccctggatcagagctccgaggtgct | Sc IL-12 EGFRBP |

SEQUENCES

| SEQ ID NO. | Sequence | Name |
|---|---|---|
| | ggggagcggaaaaacactgactattcaggtcaaggaattcggcgacgctg<br>ggcagtacacatgtcacaagggcggggaggtgctgtctcacagtctgctg<br>ctgctgcataagaaagaagacggaatctggtctactgacattctgaaaga<br>tcagaaggagcctaagaacaaaaccttcctgcgctgcgaagcaaaaaatt<br>atagcggccggttcacctgttggtggctgaccacaatctcaacagatctg<br>actttagcgtgaagtctagtaggggctcaagcgacccacagggagtcac<br>atgcggagcagctactctgagcgccgagcgggtgagagggataacaagg<br>agtacgaatatagtgtcgagtgccaggaagactcagcatgtcctgcagcc<br>gaggaatccctgccaatcgaagtgatggtcgatgccgtgcacaagctgaa<br>atacgaaaactacacatcctctttctttatccgagacatcatcaagccag<br>atcccctaagaacctgcagctgaaacccctgaagaattcccgccaggtg<br>gaggtctcttgggaatacccagacacctggtccacaccccattcctattt<br>ctctctgacttttttgcgtgcaggtccagggcaagtctaaaagagagaaga<br>aagacagggtgttcactgataaaaccagtgctacagtcatctgccggaag<br>aacgcctcaattagcgtgcgagctcaggaccggtactatagttcaagctg<br>gagtgaatgggcatcagtgccatgcagcggaggaggaggatcctctgtgg<br>ataaccctcacgtctgtggcggaggaggcagcagaaatctgcctgtggct<br>accccagaccccgggatgttcccatgcctgcaccatagccagaacctgct<br>gcgggcagtgtccaatatgctgcagaaggccagacagaccctggagttttt<br>acccatgtacaagcgaggaaatcgaccacgaggatattaccaaggataaa<br>acctccacagtggaagcctgcctgcccctggagctgacaaagaacgaatc<br>ctgtctgaattctagggagactagtttcatcaccaacggctcatgcctgg<br>ccagccgcaaaacttcctttatgatggctctgtgcctgagttcaatctac<br>gaggacctgaagatgtatcaggtggaattcaaaaccatgaacgccaagct<br>gctgatggaccccaaaaggcagatctttctggatcagaatatgctggctg<br>tgattgacgagctgatgcaggcactgaacttcaattctgaaacagtcccc<br>cagaagagctccctggaggaacctgattttacaagactaaaatcaagct<br>gtgcattctgctgcacgcttttaggatccgcgcagtgaccattgaccgcg<br>tcatgtcttatctgaatgccagtcaccatcaccattggagccat<br>cctcagtttgagaagtgataactcgag | |
| 107 | gctagcgccaccatgcctctgctgctgctgctgccactgctgtgggctgg<br>cgcactggccatctgggagctgaagaaagacgtgtacgtgtcgaactgg<br>actggtatcccgatgctcctggggagatggtggtcctgacatgcgacact<br>cccgaggaagatggaatcacatggactctggatcagagctccgaggtcct<br>gggaagcggcaaaaccctgacaattcaggtgaaggaattcggggacgccg<br>gacagtacacatgtcacaagggcggggaggtgctgtctcacagtctgctg<br>ctgctgcataagaaagaagacgggatctggtctaccgacattctgaaaga<br>tcagaaggagcccaagaacaaaacattcctgaggtgcgaagcaaaaatt<br>atagcggacgctttacctgttggtggctgaccacaatcagtaccgatctg<br>acatttttcagtcaagtctagtcggggctcaagcgaccctcagggagtgac<br>atgcggagcagctactctgtctgccgagcgggtcagagggataacaagg<br>agtacgaatattctgtggagtgccaggaagacagtgcttgtccagcagcc<br>gaggaaagcctgcccatcgaggtcatggtggatgcagtgcacaagctgaa<br>atacgaaaactacacatcctctttctttattcgggacatcatcaagccag<br>atcccctaagaacctgcagctgaaacccctgaagaatagcagacaggtc<br>gaggtgtcctgggaatacccgacacttggagcacccctcatagttatttt<br>ctcactgacctttttgcgtccaggtgcagggcaagtctaaaagagagaaga<br>aagacagggtctttcacagataagaccagcgccaccgtgatctgtagaaag<br>aacgcatcaattagcgtgcgagcccaggatcggtactatagttcaagctg<br>gagcgagtgggcctccgtgccatgctctggaggaggaggatcacaggtcc<br>agctggtgcagagcggagcagaagtgaagaaacccggctcctctgtcaaa<br>gtgagttgtaaggcctcaggcgggacttttagttcatacgcaatctctgt<br>ggtcgtgaggcaggcaccaggacagggactggagtggatgggaggcatca<br>ttcctatcttcggcaccgccaactacgctcagaagtttcaggggcgcgtg<br>actattaccgccgatgagtccacatctactgcttatatggagctgagctc<br>cctgagaagcgaagacaccgccgtgtactattgcgcaaggggcctgctgt<br>ggaattactggggccagggggacactggtcaccgtgagcagcaaagctagt<br>ggaagcgccagcgcccctaagctggaggaaggagagttcagtgaagcccg<br>ggtcgagactaccctgacccagtcccctgctacactgtccgtgtctccag<br>gagaacgcgctacactgagctgtcgagcaagtcagtcagtgtcaagcaat<br>ctggctgtcgtgtaccagcagaagccaggccaggcacccagactgctgat<br>ctatgggcaagcacccgggccacaggaattccagctagattcagcggat<br>ccggctctgggaccgagtttaccctgacaatctcctctctgcagtccgaa<br>gacttcgccgtgtactattgccagcagtacaacaattggccacccgggtt<br>cacttttggacccggcaccaaagtcgatattaagggaggagagggtccc<br>ggaacctgcctgtggcaactcctgacccaggcatgttcccatgcctgcac<br>cattcccagaacctgctgcgagccgtgagcaatatgctgcagaaagcacg<br>gcagacactggagttttatccttgtactagcgaggaaatcgaccacgagg<br>atattacaaaggataaaacttccaccgtggaagcctgcctgccactggag<br>ctgactaagaacgaaagctgtctgaattcccgcgagacttctttcatcac<br>caatggcagttgcctggcatcacgaaaaaccagctttatgatggccctgt<br>gcctgagttcaatctacgaggacctgaagatgtatcaggtggaattcaaa | Sc IL-12 anti-EPCAM |

-continued

| SEQ ID NO. | Sequence | Name |
|---|---|---|
| | acaatgaacgccaagctgctgatggaccctaaaaggcagatctttctgga<br>tcagaatatgctggccgtgattgacgagctgatgcaggctctgaacttca<br>atagcgaaactgtgccccagaagagctccctggaggaacctgatttctac<br>aagaccaaaatcaagctgtgcattctgctgcacgcctttaggatccgcgc<br>tgtcaccattgaccgcgtgatgtcctatctgaacgcctctcaccatcacc<br>atcaccattggtcccatccacagtttgagaagtgataactcgag | |
| 108 | YHWYGYTPQNVI | EGFR binding peptide |
| 109 | YRWYGYTPQNVI | EGFR binding peptide |
| 110 | PCAIWF | VEGFR3 binding peptide |
| 111 | WVCSGG | VEGFR3 binding peptide |
| 112 | NGRNGRNGR | NGR motif |
| 113 | RGDRGDRGD | RGD motif |
| 114 | TAASGVRSMH | NG2 proteoglycan binding peptide |
| 115 | LTLRWVGLMS | NG2 proteoglycan binding peptide |
| 116 | NKFNKGMRYWGALGGNGKRGIRGYM | HER2 binding peptide |
| 117 | YEVHTYYLD | EPCAM binding peptide |
| 118 | ITMQIMRIKPHQGQHIGEMSF | VEGFR binding peptide |

The invention claimed is:

1. An immunomodulatory polypeptide comprising:
   a) a first peptide comprising a p35 subunit of IL-12 or a functional portion thereof;
   b) a second peptide comprising a p40 subunit of IL-12 or a functional portion thereof; and
   c) a joining region connecting the first and second peptides, wherein the joining region comprises a targeting moiety;
   wherein:
   the p35 subunit comprises the sequence of amino acids set forth in SEQ ID NO: 10 or a sequence that has at least 95% sequence identity to SEQ ID NO: 10 and the p40 subunit comprises the sequence of amino acids set forth in SEQ ID NO: 11 or a sequence that has at least 95% sequence identity to SEQ ID NO: 11;
   the targeting moiety comprises an antibody or an antibody fragment comprising a variable heavy (VH) chain and a variable light (VL) chain, or a peptide binding motif that is between 5 and 50 amino acids; and
   the targeting moiety binds to a target molecule that is a tumor antigen.

2. The immunomodulatory polypeptide of claim 1, wherein the joining region further comprises at least one polypeptide linker linking the targeting moiety to the p35 subunit or the p40 subunit.

3. The immunomodulatory polypeptide of claim 1, wherein the target molecule is selected from the group consisting of: hepatocyte growth factor (HGF), hepatocyte growth factor receptor (HGFR), heparin, VEGF, VEGF-A, VEGFR2, VEGFR3, HER2, PD-1, tenascin-C, CTLA-4, LAG3, PD-L1, EGFR, EPCAM, RANKL, NG2 proteoglycan, CD20, CD52, CD19, CD3, CD30, IL-6, CD38, SLAMF7, GD2, CD13, CD274, CD279, CD40L, and CD47.

4. The immunomodulatory polypeptide of claim 1, wherein the antibody fragment is a single chain fragment.

5. The immunomodulatory polypeptide of claim 4, wherein the single chain fragment is a single domain antibody comprising the variable heavy chain region or is an ScFv.

6. The immunomodulatory polypeptide of claim 1, wherein the targeting moiety comprises a variable heavy (VH) chain or variable light (VL) chain of an antibody selected from the group consisting of: trastuzumab, pertuzumab, ramucirumab, atezolizumab, bevacizumab, panitumumab, cetuximab, necitumumab, denosumab, nivolumab, pembrolizumab, rituximab, ofatumumab, obinutuzumab, alemtuzumab, blinatumomab, brentuximab vedotin, siltuximab, ipilimumab, daratumumab, elotuzumab, dinutuximab, Catumaxomab.

7. The immunomodulatory polypeptide of claim 1 wherein the targeting moiety comprises an HGF binding peptide or an EGFR binding peptide (EGFRBP).

8. The immunomodulatory polypeptide of claim 1, wherein:
the immunomodulatory polypeptide exhibits increased activity to stimulate via the IL-12R compared to a reference IL-12.

9. The immunomodulatory polypeptide of claim 8, wherein the increased activity is by greater than 1.2-fold.

10. The immunomodulatory peptide of claim 1, wherein the p35 subunit comprises the sequence of amino acids set forth in SEQ ID NO: 10.

11. The immunomodulatory peptide of claim 1, wherein the p40 subunit comprises the sequence of amino acids set forth in SEQ ID NO: 11.

12. The immunomodulatory peptide of claim 1, wherein the p35 subunit comprises the sequence of amino acids set forth in SEQ ID NO: 10 and the p40 subunit comprises the sequence of amino acids set forth in SEQ ID NO: 11.

13. The immunomodulatory peptide of claim 1, wherein the immunomodulatory polypeptide exhibits increased binding to a target cell expressing the target molecule as compared with its binding to a cell not expressing the target molecule.

14. The immunomodulatory polypeptide of claim 1, wherein the targeting moiety comprises a variable heavy (VH) chain and a variable light (VL) chain of an antibody selected from the group consisting of: trastuzumab, pertuzumab, ramucirumab, atezolizumab, bevacizumab, panitumumab, cetuximab, necitumumab, denosumab, nivolumab, pembrolizumab, rituximab, ofatumumab, obinutuzumab, alemtuzumab, blinatumomab, brentuximab vedotin, siltuximab, ipilimumab, daratumumab, elotuzumab, dinutuximab, Catumaxomab.

15. A composition comprising the immunomodulatory polypeptide of claim 1.

* * * * *

SEQUENCE LISTING

<160> NUMBER OF SEQ ID NOS: 118

<210> SEQ ID NO 1
<211> LENGTH: 518
<212> TYPE: PRT
<213> ORGANISM: Artificial Sequence
<220> FEATURE:
<223> OTHER INFORMATION: Sc IL-12 G4S(3)

<400> SEQUENCE: 1

```
Ile Trp Glu Leu Lys Lys Asp Val Tyr Val Val Glu Leu Asp Trp Tyr
1               5                   10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
        35                  40                  45
Ser Gly Lys Thr Leu Thr Ile Gln Val Lys Glu Phe Gly Asp Ala Gly
    50                  55                  60
Gln Tyr Thr Cys His Lys Gly Gly Glu Val Leu Ser His Ser Leu Leu
65                  70                  75                  80
Leu Leu His Lys Lys Glu Asp Gly Ile Trp Ser Thr Asp Ile Leu Lys
                85                  90                  95
```

```
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
        115                 120                 125
Asp Leu Thr Phe Ser Val Lys Ser Ser Arg Gly Ser Ser Asp Pro Gln
    130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
        195                 200                 205
Asp Ile Ile Lys Pro Asp Pro Pro Lys Asn Leu Gln Leu Lys Pro Leu
    210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
            260                 265                 270
Ser Ala Thr Val Ile Cys Arg Lys Asn Ala Ser Ile Ser Val Arg Ala
        275                 280                 285
Gln Asp Arg Tyr Tyr Ser Ser Ser Trp Ser Glu Trp Ala Ser Val Pro
    290                 295                 300
Cys Ser Gly Gly Gly Ser Gly Gly Gly Ser Gly Gly Gly Gly Gly Gly
305                 310                 315                 320
Ser Arg Asn Leu Pro Val Ala Thr Pro Asp Pro Gly Met Phe Pro Cys
                325                 330                 335
Leu His His Ser Gln Asn Leu Leu Arg Ala Val Ser Asn Met Leu Gln
            340                 345                 350
Lys Ala Arg Gln Thr Leu Glu Phe Tyr Pro Cys Thr Ser Glu Glu Ile
        355                 360                 365
Asp His Glu Asp Ile Thr Lys Asp Lys Thr Ser Thr Val Glu Ala Cys
    370                 375                 380
Leu Pro Leu Glu Leu Thr Lys Asn Glu Ser Cys Leu Asn Ser Arg Glu
385                 390                 395                 400
Thr Ser Phe Ile Thr Asn Gly Ser Cys Leu Ala Ser Arg Lys Thr Ser
                405                 410                 415
Phe Met Met Ala Leu Cys Leu Ser Ser Ile Tyr Glu Asp Leu Lys Met
            420                 425                 430
Tyr Gln Val Glu Phe Lys Thr Met Asn Ala Lys Leu Leu Met Asp Pro
        435                 440                 445
Lys Arg Gln Ile Phe Leu Asp Gln Asn Met Leu Ala Val Ile Asp Glu
    450                 455                 460
Leu Met Gln Ala Leu Asn Phe Asn Ser Glu Thr Val Pro Gln Lys Ser
465                 470                 475                 480
Ser Leu Glu Glu Pro Asp Phe Tyr Lys Thr Lys Ile Lys Leu Cys Ile
                485                 490                 495
Leu Leu His Ala Phe Arg Ile Arg Ala Val Thr Ile Asp Arg Val Met
            500                 505                 510
Ser Tyr Leu Asn Ala Ser
```

```
                515

<210> SEQ ID NO 2
<211> LENGTH: 523
<212> TYPE: PRT
<213> ORGANISM: Artificial Sequence
<220> FEATURE:
<223> OTHER INFORMATION: Sc IL-12 HBP BMP4

<400> SEQUENCE: 2

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Ser Arg Lys Lys Asn Pro Asn Cys Arg Arg
305                 310                 315                 320

His Gly Gly Gly Gly Ser Arg Asn Leu Pro Val Ala Thr Pro Asp Pro
                325                 330                 335

Gly Met Phe Pro Cys Leu His His Ser Gln Asn Leu Leu Arg Ala Val
            340                 345                 350

Ser Asn Met Leu Gln Lys Ala Arg Gln Thr Leu Glu Phe Tyr Pro Cys
```

```
                355                 360                 365
Thr Ser Glu Glu Ile Asp His Glu Asp Ile Thr Lys Asp Lys Thr Ser
370                 375                 380
Thr Val Glu Ala Cys Leu Pro Leu Glu Leu Thr Lys Asn Glu Ser Cys
385                 390                 395                 400
Leu Asn Ser Arg Glu Thr Ser Phe Ile Thr Asn Gly Ser Cys Leu Ala
                405                 410                 415
Ser Arg Lys Thr Ser Phe Met Met Ala Leu Cys Leu Ser Ser Ile Tyr
            420                 425                 430
Glu Asp Leu Lys Met Tyr Gln Val Glu Phe Lys Thr Met Asn Ala Lys
            435                 440                 445
Leu Leu Met Asp Pro Lys Arg Gln Ile Phe Leu Asp Gln Asn Met Leu
            450                 455                 460
Ala Val Ile Asp Glu Leu Met Gln Ala Leu Asn Phe Asn Ser Glu Thr
465                 470                 475                 480
Val Pro Gln Lys Ser Ser Leu Glu Glu Pro Asp Phe Tyr Lys Thr Lys
                485                 490                 495
Ile Lys Leu Cys Ile Leu Leu His Ala Phe Arg Ile Arg Ala Val Thr
            500                 505                 510
Ile Asp Arg Val Met Ser Tyr Leu Asn Ala Ser
            515                 520

<210> SEQ ID NO 3
<211> LENGTH: 528
<212> TYPE: PRT
<213> ORGANISM: Artificial Sequence
<220> FEATURE:
<223> OTHER INFORMATION: Sc IL-12 HBP FBN

<400> SEQUENCE: 3

Ile Trp Glu Leu Lys Lys Asp Val Tyr Val Val Glu Leu Asp Trp Tyr
1               5                   10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
        35                  40                  45
Ser Gly Lys Thr Leu Thr Ile Gln Val Lys Glu Phe Gly Asp Ala Gly
    50                  55                  60
Gln Tyr Thr Cys His Lys Gly Gly Glu Val Leu Ser His Ser Leu Leu
65                  70                  75                  80
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
        115                 120                 125
Asp Leu Thr Phe Ser Val Lys Ser Ser Arg Gly Ser Ser Asp Pro Gln
    130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
```

```
                195                 200                 205
Asp Ile Ile Lys Pro Asp Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
290                 295                 300

Cys Ser Gly Gly Gly Ser Lys Asn Asn Gln Lys Ser Glu Pro Leu
305                 310                 315                 320

Ile Gly Arg Lys Lys Thr Gly Gly Gly Ser Arg Asn Leu Pro Val
                325                 330                 335

Ala Thr Pro Asp Pro Gly Met Phe Pro Cys Leu His His Ser Gln Asn
                340                 345                 350

Leu Leu Arg Ala Val Ser Asn Met Leu Gln Lys Ala Arg Gln Thr Leu
                355                 360                 365

Glu Phe Tyr Pro Cys Thr Ser Glu Glu Ile Asp His Glu Asp Ile Thr
370                 375                 380

Lys Asp Lys Thr Ser Thr Val Glu Ala Cys Leu Pro Leu Glu Leu Thr
385                 390                 395                 400

Lys Asn Glu Ser Cys Leu Asn Ser Arg Glu Thr Ser Phe Ile Thr Asn
                405                 410                 415

Gly Ser Cys Leu Ala Ser Arg Lys Thr Ser Phe Met Met Ala Leu Cys
                420                 425                 430

Leu Ser Ser Ile Tyr Glu Asp Leu Lys Met Tyr Gln Val Glu Phe Lys
                435                 440                 445

Thr Met Asn Ala Lys Leu Leu Met Asp Pro Lys Arg Gln Ile Phe Leu
450                 455                 460

Asp Gln Asn Met Leu Ala Val Ile Asp Glu Leu Met Gln Ala Leu Asn
465                 470                 475                 480

Phe Asn Ser Glu Thr Val Pro Gln Lys Ser Leu Glu Glu Pro Asp
                485                 490                 495

Phe Tyr Lys Thr Lys Ile Lys Leu Cys Ile Leu Leu His Ala Phe Arg
                500                 505                 510

Ile Arg Ala Val Thr Ile Asp Arg Val Met Ser Tyr Leu Asn Ala Ser
                515                 520                 525

<210> SEQ ID NO 4
<211> LENGTH: 529
<212> TYPE: PRT
<213> ORGANISM: Artificial Sequence
<220> FEATURE:
<223> OTHER INFORMATION: Sc IL-12 HGFBP

<400> SEQUENCE: 4

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
                20                  25                  30

Glu Asp Gly Ile Thr Trp Thr Leu Asp Gln Ser Ser Glu Val Leu Gly
```

```
                35                  40                  45
Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Ser Val Trp Asn Trp Val Cys Phe Arg Asp
305                 310                 315                 320

Val Gly Cys Asp Trp Val Leu Gly Gly Gly Ser Arg Asn Leu Pro
                325                 330                 335

Val Ala Thr Pro Asp Pro Gly Met Phe Pro Cys Leu His His Ser Gln
            340                 345                 350

Asn Leu Leu Arg Ala Val Ser Asn Met Leu Gln Lys Ala Arg Gln Thr
        355                 360                 365

Leu Glu Phe Tyr Pro Cys Thr Ser Glu Glu Ile Asp His Glu Asp Ile
    370                 375                 380

Thr Lys Asp Lys Thr Ser Thr Val Glu Ala Cys Leu Pro Leu Glu Leu
385                 390                 395                 400

Thr Lys Asn Glu Ser Cys Leu Asn Ser Arg Glu Thr Ser Phe Ile Thr
                405                 410                 415

Asn Gly Ser Cys Leu Ala Ser Arg Lys Thr Ser Phe Met Met Ala Leu
            420                 425                 430

Cys Leu Ser Ser Ile Tyr Glu Asp Leu Lys Met Tyr Gln Val Glu Phe
        435                 440                 445

Lys Thr Met Asn Ala Lys Leu Leu Met Asp Pro Lys Arg Gln Ile Phe
    450                 455                 460
```

-continued

```
Leu Asp Gln Asn Met Leu Ala Val Ile Asp Glu Leu Met Gln Ala Leu
465                 470                 475                 480

Asn Phe Asn Ser Glu Thr Val Pro Gln Lys Ser Ser Leu Glu Glu Pro
                485                 490                 495

Asp Phe Tyr Lys Thr Lys Ile Lys Leu Cys Ile Leu Leu His Ala Phe
            500                 505                 510

Arg Ile Arg Ala Val Thr Ile Asp Arg Val Met Ser Tyr Leu Asn Ala
        515                 520                 525

Ser

<210> SEQ ID NO 5
<211> LENGTH: 521
<212> TYPE: PRT
<213> ORGANISM: Artificial Sequence
<220> FEATURE:
<223> OTHER INFORMATION: Sc IL-12 EGFRBP

<400> SEQUENCE: 5

Ile Trp Glu Leu Lys Lys Asp Val Tyr Val Val Glu Leu Asp Trp Tyr
1               5                  10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285
```

```
Gln Asp Arg Tyr Tyr Ser Ser Ser Trp Ser Glu Trp Ala Ser Val Pro
        290                 295                 300

Cys Ser Gly Gly Gly Ser Ser Val Asp Asn Pro His Val Cys Gly
305                 310                 315                 320

Gly Gly Gly Ser Arg Asn Leu Pro Val Ala Thr Pro Asp Pro Gly Met
                325                 330                 335

Phe Pro Cys Leu His His Ser Gln Asn Leu Leu Arg Ala Val Ser Asn
            340                 345                 350

Met Leu Gln Lys Ala Arg Gln Thr Leu Glu Phe Tyr Pro Cys Thr Ser
        355                 360                 365

Glu Glu Ile Asp His Glu Asp Ile Thr Lys Asp Lys Thr Ser Thr Val
370                 375                 380

Glu Ala Cys Leu Pro Leu Glu Leu Thr Lys Asn Glu Ser Cys Leu Asn
385                 390                 395                 400

Ser Arg Glu Thr Ser Phe Ile Thr Asn Gly Ser Cys Leu Ala Ser Arg
                405                 410                 415

Lys Thr Ser Phe Met Met Ala Leu Cys Leu Ser Ser Ile Tyr Glu Asp
            420                 425                 430

Leu Lys Met Tyr Gln Val Glu Phe Lys Thr Met Asn Ala Lys Leu Leu
        435                 440                 445

Met Asp Pro Lys Arg Gln Ile Phe Leu Asp Gln Asn Met Leu Ala Val
450                 455                 460

Ile Asp Glu Leu Met Gln Ala Leu Asn Phe Asn Ser Glu Thr Val Pro
465                 470                 475                 480

Gln Lys Ser Ser Leu Glu Glu Pro Asp Phe Tyr Lys Thr Lys Ile Lys
                485                 490                 495

Leu Cys Ile Leu Leu His Ala Phe Arg Ile Arg Ala Val Thr Ile Asp
            500                 505                 510

Arg Val Met Ser Tyr Leu Asn Ala Ser
        515                 520

<210> SEQ ID NO 6
<211> LENGTH: 760
<212> TYPE: PRT
<213> ORGANISM: Artificial Sequence
<220> FEATURE:
<223> OTHER INFORMATION: Sc IL-12 Anti EPCAM

<400> SEQUENCE: 6

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125
```

-continued

```
Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Trp Ser Glu Trp Ala Ser Val Pro
    290                 295                 300

Cys Ser Gly Gly Gly Ser Gln Val Gln Leu Val Gln Ser Gly Ala
305                 310                 315                 320

Glu Val Lys Lys Pro Gly Ser Ser Val Lys Val Ser Cys Lys Ala Ser
                325                 330                 335

Gly Gly Thr Phe Ser Ser Tyr Ala Ile Ser Val Val Arg Gln Ala
            340                 345                 350

Pro Gly Gln Gly Leu Glu Trp Met Gly Gly Ile Ile Pro Ile Phe Gly
        355                 360                 365

Thr Ala Asn Tyr Ala Gln Lys Phe Gln Gly Arg Val Thr Ile Thr Ala
    370                 375                 380

Asp Glu Ser Thr Ser Thr Ala Tyr Met Glu Leu Ser Ser Leu Arg Ser
385                 390                 395                 400

Glu Asp Thr Ala Val Tyr Tyr Cys Ala Arg Gly Leu Leu Trp Asn Tyr
                405                 410                 415

Trp Gly Gln Gly Thr Leu Val Thr Val Ser Ser Lys Leu Ser Gly Ser
            420                 425                 430

Ala Ser Ala Pro Lys Leu Glu Glu Gly Glu Phe Ser Glu Ala Arg Val
        435                 440                 445

Glu Thr Thr Leu Thr Gln Ser Pro Ala Thr Leu Ser Val Ser Pro Gly
    450                 455                 460

Glu Arg Ala Thr Leu Ser Cys Arg Ala Ser Gln Ser Val Ser Ser Asn
465                 470                 475                 480

Leu Ala Val Val Tyr Gln Gln Lys Pro Gly Gln Ala Pro Arg Leu Leu
                485                 490                 495

Ile Tyr Gly Ala Ser Thr Arg Ala Thr Gly Ile Pro Ala Arg Phe Ser
            500                 505                 510

Gly Ser Gly Ser Gly Thr Glu Phe Thr Leu Thr Ile Ser Ser Leu Gln
        515                 520                 525

Ser Glu Asp Phe Ala Val Tyr Tyr Cys Gln Gln Tyr Asn Asn Trp Pro
    530                 535                 540

Pro Gly Phe Thr Phe Gly Pro Gly Thr Lys Val Asp Ile Lys Gly Gly
```

```
                545                 550                 555                 560
Gly Gly Ser Arg Asn Leu Pro Val Ala Thr Pro Asp Pro Gly Met Phe
                565                 570                 575
Pro Cys Leu His His Ser Gln Asn Leu Leu Arg Ala Val Ser Asn Met
            580                 585                 590
Leu Gln Lys Ala Arg Gln Thr Leu Glu Phe Tyr Pro Cys Thr Ser Glu
        595                 600                 605
Glu Ile Asp His Glu Asp Ile Thr Lys Asp Lys Thr Ser Thr Val Glu
    610                 615                 620
Ala Cys Leu Pro Leu Glu Leu Thr Lys Asn Glu Ser Cys Leu Asn Ser
625                 630                 635                 640
Arg Glu Thr Ser Phe Ile Thr Asn Gly Ser Cys Leu Ala Ser Arg Lys
                645                 650                 655
Thr Ser Phe Met Met Ala Leu Cys Leu Ser Ser Ile Tyr Glu Asp Leu
            660                 665                 670
Lys Met Tyr Gln Val Glu Phe Lys Thr Met Asn Ala Lys Leu Leu Met
        675                 680                 685
Asp Pro Lys Arg Gln Ile Phe Leu Asp Gln Asn Met Leu Ala Val Ile
    690                 695                 700
Asp Glu Leu Met Gln Ala Leu Asn Phe Asn Ser Glu Thr Val Pro Gln
705                 710                 715                 720
Lys Ser Ser Leu Glu Glu Pro Asp Phe Tyr Lys Thr Lys Ile Lys Leu
                725                 730                 735
Cys Ile Leu Leu His Ala Phe Arg Ile Arg Ala Val Thr Ile Asp Arg
            740                 745                 750
Val Met Ser Tyr Leu Asn Ala Ser
        755                 760

<210> SEQ ID NO 7
<211> LENGTH: 5
<212> TYPE: PRT
<213> ORGANISM: Artificial Sequence
<220> FEATURE:
<223> OTHER INFORMATION: G4S linker

<400> SEQUENCE: 7

Gly Gly Gly Gly Ser
1               5

<210> SEQ ID NO 8
<211> LENGTH: 10
<212> TYPE: PRT
<213> ORGANISM: Artificial Sequence
<220> FEATURE:
<223> OTHER INFORMATION: G4S(2) linker

<400> SEQUENCE: 8

Gly Gly Gly Gly Ser Gly Gly Gly Gly Ser
1               5                   10

<210> SEQ ID NO 9
<211> LENGTH: 15
<212> TYPE: PRT
<213> ORGANISM: Artificial Sequence
<220> FEATURE:
<223> OTHER INFORMATION: G4S(3) linker

<400> SEQUENCE: 9

Gly Gly Gly Gly Ser Gly Gly Gly Gly Ser Gly Gly Gly Gly Ser
1               5                   10                  15
```

<210> SEQ ID NO 10
<211> LENGTH: 197
<212> TYPE: PRT
<213> ORGANISM: Artificial Sequence
<220> FEATURE:
<223> OTHER INFORMATION: IL-12 p35

<400> SEQUENCE: 10

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 11
<211> LENGTH: 306
<212> TYPE: PRT
<213> ORGANISM: Artificial Sequence
<220> FEATURE:
<223> OTHER INFORMATION: IL-12 p40

<400> SEQUENCE: 11

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
```

```
                   100                 105                 110
Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
    195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
    275                 280                 285

Gln Asp Arg Tyr Tyr Ser Ser Ser Trp Ser Glu Trp Ala Ser Val Pro
290                 295                 300

Cys Ser
305

<210> SEQ ID NO 12
<211> LENGTH: 22
<212> TYPE: PRT
<213> ORGANISM: Artificial Sequence
<220> FEATURE:
<223> OTHER INFORMATION: IL-12p40 signal sequence

<400> SEQUENCE: 12

Met Cys His Gln Gln Leu Val Ile Ser Trp Phe Ser Leu Val Phe Leu
1               5                   10                  15

Ala Ser Pro Leu Val Ala
            20

<210> SEQ ID NO 13
<211> LENGTH: 10
<212> TYPE: PRT
<213> ORGANISM: Artificial Sequence
<220> FEATURE:
<223> OTHER INFORMATION: Heparin binding peptide, BMP4

<400> SEQUENCE: 13

Arg Lys Lys Asn Pro Asn Cys Arg Arg His
1               5                   10

<210> SEQ ID NO 14
<211> LENGTH: 15
<212> TYPE: PRT
<213> ORGANISM: Artificial Sequence
<220> FEATURE:
<223> OTHER INFORMATION: Heparin binding peptide, fibronectin

<400> SEQUENCE: 14
```

```
Lys Asn Asn Gln Lys Ser Glu Pro Leu Ile Gly Arg Lys Lys Thr
1               5                   10                  15
```

<210> SEQ ID NO 15
<211> LENGTH: 16
<212> TYPE: PRT
<213> ORGANISM: Artificial Sequence
<220> FEATURE:
<223> OTHER INFORMATION: HGF binding peptide

<400> SEQUENCE: 15

```
Val Trp Asn Trp Val Cys Phe Arg Asp Val Gly Cys Asp Trp Val Leu
1               5                   10                  15
```

<210> SEQ ID NO 16
<211> LENGTH: 8
<212> TYPE: PRT
<213> ORGANISM: Artificial Sequence
<220> FEATURE:
<223> OTHER INFORMATION: EGFRBP

<400> SEQUENCE: 16

```
Ser Val Asp Asn Pro His Val Cys
1               5
```

<210> SEQ ID NO 17
<211> LENGTH: 247
<212> TYPE: PRT
<213> ORGANISM: Artificial Sequence
<220> FEATURE:
<223> OTHER INFORMATION: Anti-EPCAM scFv

<400> SEQUENCE: 17

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Val Arg Gln Ala Pro Gly Gln Gly Leu Glu Trp
        35                  40                  45

Met Gly Gly Ile Ile Pro Ile Phe Gly Thr Ala Asn Tyr Ala Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Gly Leu Leu Trp Asn Tyr Trp Gly Gln Gly Thr Leu Val
            100                 105                 110

Thr Val Ser Ser Lys Leu Ser Gly Ser Ala Ser Ala Pro Lys Leu Glu
        115                 120                 125

Glu Gly Glu Phe Ser Glu Ala Arg Val Glu Thr Thr Leu Thr Gln Ser
    130                 135                 140

Pro Ala Thr Leu Ser Val Ser Pro Gly Glu Arg Ala Thr Leu Ser Cys
145                 150                 155                 160

Arg Ala Ser Gln Ser Val Ser Ser Asn Leu Ala Val Val Tyr Gln Gln
                165                 170                 175

Lys Pro Gly Gln Ala Pro Arg Leu Leu Ile Tyr Gly Ala Ser Thr Arg
            180                 185                 190

Ala Thr Gly Ile Pro Ala Arg Phe Ser Gly Ser Gly Ser Gly Thr Glu
        195                 200                 205
```

-continued

```
Phe Thr Leu Thr Ile Ser Ser Leu Gln Ser Glu Asp Phe Ala Val Tyr
        210                 215                 220

Tyr Cys Gln Gln Tyr Asn Asn Trp Pro Pro Gly Phe Thr Phe Gly Pro
225                 230                 235                 240

Gly Thr Lys Val Asp Ile Lys
                245

<210> SEQ ID NO 18
<211> LENGTH: 17
<212> TYPE: PRT
<213> ORGANISM: Artificial Sequence
<220> FEATURE:
<223> OTHER INFORMATION: CD33 signal sequence

<400> SEQUENCE: 18

Met Pro Leu Leu Leu Leu Leu Pro Leu Leu Trp Ala Gly Ala Leu Ala
1               5                   10                  15

Met

<210> SEQ ID NO 19
<211> LENGTH: 22
<212> TYPE: PRT
<213> ORGANISM: Artificial Sequence
<220> FEATURE:
<223> OTHER INFORMATION: IL-12 p35 signal sequence

<400> SEQUENCE: 19

Met Cys Pro Ala Arg Ser Leu Leu Leu Val Ala Thr Leu Val Leu Leu
1               5                   10                  15

Asp His Leu Ser Leu Ala
            20

<210> SEQ ID NO 20
<211> LENGTH: 6
<212> TYPE: PRT
<213> ORGANISM: Artificial Sequence
<220> FEATURE:
<223> OTHER INFORMATION: 6x His-tag

<400> SEQUENCE: 20

His His His His His His
1               5

<210> SEQ ID NO 21
<211> LENGTH: 8
<212> TYPE: PRT
<213> ORGANISM: Artificial Sequence
<220> FEATURE:
<223> OTHER INFORMATION: Strep-tag(r) II

<400> SEQUENCE: 21

Trp Ser His Pro Gln Phe Glu Lys
1               5

<210> SEQ ID NO 22
<211> LENGTH: 21
<212> TYPE: PRT
<213> ORGANISM: Artificial Sequence
<220> FEATURE:
<223> OTHER INFORMATION: linker

<400> SEQUENCE: 22

Lys Leu Ser Gly Ser Ala Ser Ala Pro Lys Leu Glu Glu Gly Glu Phe
1               5                   10                  15
```

Ser Glu Ala Arg Val
        20

<210> SEQ ID NO 23
<211> LENGTH: 18
<212> TYPE: PRT
<213> ORGANISM: Artificial Sequence
<220> FEATURE:
<223> OTHER INFORMATION: linker

<400> SEQUENCE: 23

Gly Ser Thr Ser Gly Ser Gly Lys Pro Gly Ser Gly Glu Gly Ser Thr
1               5                   10                  15

Lys Gly

<210> SEQ ID NO 24
<211> LENGTH: 116
<212> TYPE: PRT
<213> ORGANISM: Artificial Sequence
<220> FEATURE:
<223> OTHER INFORMATION: Anti-EPCAM

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Val Val Arg Gln Ala Pro Gly Gln Gly Leu Glu Trp
        35                  40                  45

Met Gly Gly Ile Ile Pro Ile Phe Gly Thr Ala Asn Tyr Ala Gln Lys
    50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Gly Leu Leu Trp Asn Tyr Trp Gly Gln Gly Thr Leu Val
            100                 105                 110

Thr Val Ser Ser
        115

<210> SEQ ID NO 25
<211> LENGTH: 110
<212> TYPE: PRT
<213> ORGANISM: Artificial Sequence
<220> FEATURE:
<223> OTHER INFORMATION: Anti-EPCAM variable heavy (VH)

<400> SEQUENCE: 25

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Val Val Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Asn Asn Trp Pro
                85                  90                  95

Pro Gly Phe Thr Phe Gly Pro Gly Thr Lys Val Asp Ile Lys
            100                 105                 110

<210> SEQ ID NO 26
<211> LENGTH: 7
<212> TYPE: PRT
<213> ORGANISM: Artificial Sequence
<220> FEATURE:
<223> OTHER INFORMATION: VEGF binding peptide

<400> SEQUENCE: 26

Ala Thr Trp Leu Pro Pro Arg
1               5

<210> SEQ ID NO 27
<211> LENGTH: 23
<212> TYPE: PRT
<213> ORGANISM: Artificial Sequence
<220> FEATURE:
<223> OTHER INFORMATION: VEGFR binding peptide

<400> SEQUENCE: 27

Ile Thr Met Gln Cys Gly Ile His Gln Gly Gln His Pro Lys Ile Arg
1               5                   10                  15

Met Ile Cys Glu Met Ser Phe
            20

<210> SEQ ID NO 28
<211> LENGTH: 8
<212> TYPE: PRT
<213> ORGANISM: Artificial Sequence
<220> FEATURE:
<223> OTHER INFORMATION: bovine origin heparin binding peptide

<400> SEQUENCE: 28

Trp Gln Pro Pro Arg Ala Arg Ile
1               5

<210> SEQ ID NO 29
<211> LENGTH: 25
<212> TYPE: PRT
<213> ORGANISM: Artificial Sequence
<220> FEATURE:
<223> OTHER INFORMATION: Linker (GGGGS)n; n is 1 to 5
<220> FEATURE:
<221> NAME/KEY: VARIANT
<222> LOCATION: (6)..(10)
<223> OTHER INFORMATION: (Xaa Xaa Xaa Xaa Xaa) = (Gly Gly Gly Gly Ser)
      or null
<220> FEATURE:
<221> NAME/KEY: VARIANT
<222> LOCATION: (11)..(15)
<223> OTHER INFORMATION: (Xaa Xaa Xaa Xaa Xaa) = (Gly Gly Gly Gly Ser)
      or null
<220> FEATURE:
<221> NAME/KEY: VARIANT
<222> LOCATION: (16)..(20)
<223> OTHER INFORMATION: (Xaa Xaa Xaa Xaa Xaa) = (Gly Gly Gly Gly Ser)
      or null
<220> FEATURE:
<221> NAME/KEY: VARIANT
<222> LOCATION: (21)..(25)
<223> OTHER INFORMATION: (Xaa Xaa Xaa Xaa Xaa) = (Gly Gly Gly Gly Ser)
      or null

<400> SEQUENCE: 29

Gly Gly Gly Gly Ser Xaa Xaa Xaa Xaa Xaa Xaa Xaa Xaa Xaa Xaa Xaa
1               5                   10                  15

```
Xaa Xaa Xaa Xaa Xaa Xaa Xaa Xaa
            20              25

<210> SEQ ID NO 30
<211> LENGTH: 133
<212> TYPE: PRT
<213> ORGANISM: Homo sapiens
<220> FEATURE:
<221> NAME/KEY: misc_feature
<223> OTHER INFORMATION: IL-15

<400> SEQUENCE: 30

Gly Ile His Val Phe Ile Leu Gly Cys Phe Ser Ala Gly Leu Pro Lys
1               5                   10                  15

Thr Glu Ala Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser
    130

<210> SEQ ID NO 31
<211> LENGTH: 133
<212> TYPE: PRT
<213> ORGANISM: Homo sapiens
<220> FEATURE:
<221> NAME/KEY: misc_feature
<223> OTHER INFORMATION: IL-2

<400> SEQUENCE: 31

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 32
<211> LENGTH: 193
<212> TYPE: PRT
<213> ORGANISM: Homo sapiens
<220> FEATURE:
<221> NAME/KEY: misc_feature
<223> OTHER INFORMATION: IL-19

<400> SEQUENCE: 32

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 33
<211> LENGTH: 127
<212> TYPE: PRT
<213> ORGANISM: Homo sapiens
<220> FEATURE:
<221> NAME/KEY: misc_feature
<223> OTHER INFORMATION: GM-CSF

<400> SEQUENCE: 33

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp

```
                        100                 105                 110
Phe Leu Leu Val Ile Pro Phe Asp Cys Trp Glu Pro Val Gln Glu
            115                 120                 125

<210> SEQ ID NO 34
<211> LENGTH: 152
<212> TYPE: PRT
<213> ORGANISM: Homo sapiens
<220> FEATURE:
<221> NAME/KEY: misc_feature
<223> OTHER INFORMATION: IL-7

<400> SEQUENCE: 34

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
130                 135                 140

Ile Leu Met Gly Thr Lys Glu His
145                 150

<210> SEQ ID NO 35
<211> LENGTH: 133
<212> TYPE: PRT
<213> ORGANISM: Homo sapiens
<220> FEATURE:
<221> NAME/KEY: misc_feature
<223> OTHER INFORMATION: IL-21

<400> SEQUENCE: 35

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
```

```
                    115                 120                 125

Gly Ser Glu Asp Ser
        130

<210> SEQ ID NO 36
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-1/13

<400> SEQUENCE: 36

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 37
<211> LENGTH: 165
<212> TYPE: PRT
<213> ORGANISM: Homo sapiens
<220> FEATURE:
<221> NAME/KEY: misc_feature
<223> OTHER INFORMATION: IFN alpha-2

<400> SEQUENCE: 37

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
```

```
            100             105             110
Glu Asp Ser Ile Leu Ala Val Arg Lys Tyr Phe Gln Arg Ile Thr Leu
            115             120             125
Tyr Leu Lys Glu Lys Lys Tyr Ser Pro Cys Ala Trp Glu Val Val Arg
            130             135             140
Ala Glu Ile Met Arg Ser Phe Ser Leu Ser Thr Asn Leu Gln Glu Ser
145             150             155             160
Leu Arg Ser Lys Glu
            165

<210> SEQ ID NO 38
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-4

<400> SEQUENCE: 38

Cys Asp Leu Pro Gln Thr His Ser Leu Gly Asn Arg Arg Ala Leu Ile
1               5               10              15
Leu Leu Ala Gln Met Gly Arg Ile Ser His Phe Ser Cys Leu Lys Asp
            20              25              30
Arg His Asp Phe Gly Phe Pro Glu Glu Glu Phe Asp Gly His Gln Phe
            35              40              45
Gln Lys Ala Gln Ala Ile Ser Val Leu His Glu Met Ile Gln Gln Thr
        50              55              60
Phe Asn Leu Phe Ser Thr Glu Asp Ser Ser Ala Ala Trp Glu Gln Ser
65              70              75              80
Leu Leu Glu Lys Phe Ser Thr Glu Leu Tyr Gln Gln Leu Asn Asp Leu
            85              90              95
Glu Ala Cys Val Ile Gln Glu Val Gly Val Glu Glu Thr Pro Leu Met
            100             105             110
Asn Glu Asp Ser Ile Leu Ala Val Arg Lys Tyr Phe Gln Arg Ile Thr
            115             120             125
Leu Tyr Leu Thr Glu Lys Lys Tyr Ser Pro Cys Ala Trp Glu Val Val
            130             135             140
Arg Ala Glu Ile Met Arg Ser Leu Ser Phe Ser Thr Asn Leu Gln Lys
145             150             155             160
Arg Leu Arg Arg Lys Asp
            165

<210> SEQ ID NO 39
<211> LENGTH: 168
<212> TYPE: PRT
<213> ORGANISM: Homo sapiens
<220> FEATURE:
<221> NAME/KEY: misc_feature
<223> OTHER INFORMATION: IFN alpha-5

<400> SEQUENCE: 39

Leu Gly Cys Asp Leu Pro Gln Thr His Ser Leu Ser Asn Arg Arg Thr
1               5               10              15
Leu Met Ile Met Ala Gln Met Gly Arg Ile Ser Pro Phe Ser Cys Leu
            20              25              30
Lys Asp Arg His Asp Phe Gly Phe Pro Gln Glu Glu Phe Asp Gly Asn
            35              40              45
Gln Phe Gln Lys Ala Gln Ala Ile Ser Val Leu His Glu Met Ile Gln
```

```
                50              55              60
Gln Thr Phe Asn Leu Phe Ser Thr Lys Asp Ser Ala Thr Trp Asp
65                  70                  75                  80

Glu Thr Leu Leu Asp Lys Phe Tyr Thr Glu Leu Tyr Gln Gln Leu Asn
                85                  90                  95

Asp Leu Glu Ala Cys Met Met Gln Glu Val Gly Val Glu Asp Thr Pro
            100                 105                 110

Leu Met Asn Val Asp Ser Ile Leu Thr Val Arg Lys Tyr Phe Gln Arg
            115                 120                 125

Ile Thr Leu Tyr Leu Thr Glu Lys Lys Tyr Ser Pro Cys Ala Trp Glu
            130                 135                 140

Val Val Arg Ala Glu Ile Met Arg Ser Phe Ser Leu Ser Ala Asn Leu
145                 150                 155                 160

Gln Glu Arg Leu Arg Arg Lys Glu
                165
```

```
<210> SEQ ID NO 40
<211> LENGTH: 169
<212> TYPE: PRT
<213> ORGANISM: Homo sapiens
<220> FEATURE:
<221> NAME/KEY: misc_feature
<223> OTHER INFORMATION: IFN alpha-6

<400> SEQUENCE: 40

Ser Leu Asp Cys Asp Leu Pro Gln Thr His Ser Leu Gly His Arg Arg
1               5                   10                  15

Thr Met Met Leu Leu Ala Gln Met Arg Arg Ile Ser Leu Phe Ser Cys
                20                  25                  30

Leu Lys Asp Arg His Asp Phe Arg Phe Pro Gln Glu Glu Phe Asp Gly
            35                  40                  45

Asn Gln Phe Gln Lys Ala Glu Ala Ile Ser Val Leu His Glu Val Ile
        50                  55                  60

Gln Gln Thr Phe Asn Leu Phe Ser Thr Lys Asp Ser Ser Val Ala Trp
65                  70                  75                  80

Asp Glu Arg Leu Leu Asp Lys Leu Tyr Thr Glu Leu Tyr Gln Gln Leu
                85                  90                  95

Asn Asp Leu Glu Ala Cys Val Met Gln Glu Val Trp Val Gly Gly Thr
            100                 105                 110

Pro Leu Met Asn Glu Asp Ser Ile Leu Ala Val Arg Lys Tyr Phe Gln
            115                 120                 125

Arg Ile Thr Leu Tyr Leu Thr Glu Lys Lys Tyr Ser Pro Cys Ala Trp
            130                 135                 140

Glu Val Val Arg Ala Glu Ile Met Arg Ser Phe Ser Ser Ser Arg Asn
145                 150                 155                 160

Leu Gln Glu Arg Leu Arg Arg Lys Glu
                165
```

```
<210> SEQ ID NO 41
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-7

<400> SEQUENCE: 41

Cys Asp Leu Pro Gln Thr His Ser Leu Arg Asn Arg Arg Ala Leu Ile
```

```
            1               5                  10                  15
Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
            35                  40                  45

Gln Lys Thr Gln Ala Ile Ser Val Leu His Glu Met Ile Gln Gln Thr
            50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
            85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
            130                 135                 140

Arg Ala Glu Ile Met Arg Ser Phe Ser Phe Ser Thr Asn Leu Lys Lys
145                 150                 155                 160

Gly Leu Arg Arg Lys Asp
            165

<210> SEQ ID NO 42
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-8

<400> SEQUENCE: 42

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
            35                  40                  45

Gln Lys Ala Gln Ala Ile Ser Val Leu His Glu Met Ile Gln Gln Thr
            50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
            85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
            130                 135                 140

Arg Ala Glu Ile Met Arg Ser Phe Ser Leu Ser Ile Asn Leu Gln Lys
145                 150                 155                 160

Arg Leu Lys Ser Lys Glu
            165

<210> SEQ ID NO 43
<211> LENGTH: 166
```

```
<212> TYPE: PRT
<213> ORGANISM: Homo sapiens
<220> FEATURE:
<221> NAME/KEY: misc_feature
<223> OTHER INFORMATION: IFN alpha-10

<400> SEQUENCE: 43

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 44
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-14

<400> SEQUENCE: 44

Cys Asn Leu Ser Gln Thr His Ser Leu Asn Asn Arg Arg Thr Leu Met
1               5                   10                  15

Leu Met Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
        115                 120                 125

Leu Tyr Leu Met Glu Lys Lys Tyr Ser Pro Cys Ala Trp Glu Val Val
    130                 135                 140
```

```
Arg Ala Glu Ile Met Arg Ser Leu Ser Phe Ser Thr Asn Leu Gln Lys
145                 150                 155                 160

Arg Leu Arg Arg Lys Asp
                165
```

<210> SEQ ID NO 45
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-16

<400> SEQUENCE: 45

```
Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
                20                  25                  30

Arg Tyr Asp Phe Gly Phe Pro Gln Glu Val Phe Asp Gly Asn Gln Phe
            35                  40                  45

Gln Lys Ala Gln Ala Ile Ser Ala Phe His Glu Met Ile Gln Gln Thr
        50                  55                  60

Phe Asn Leu Phe Ser Thr Lys Asp Ser Ser Ala Ala Trp Asp Glu Thr
65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Glu Ile Ala Leu Met
            100                 105                 110

Asn Glu Asp Ser Ile Leu Ala Val Arg Lys Tyr Phe Gln Arg Ile Thr
        115                 120                 125

Leu Tyr Leu Met Gly Lys Lys Tyr Ser Pro Cys Ala Trp Glu Val Val
    130                 135                 140

Arg Ala Glu Ile Met Arg Ser Phe Ser Phe Ser Thr Asn Leu Gln Lys
145                 150                 155                 160

Gly Leu Arg Arg Lys Asp
                165
```

<210> SEQ ID NO 46
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-17

<400> SEQUENCE: 46

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
                20                  25                  30

Arg His Asp Phe Gly Leu Pro Gln Glu Phe Asp Gly Asn Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95
```

```
Glu Ala Cys Val Ile Gln Glu Val Gly Met Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 47
<211> LENGTH: 166
<212> TYPE: PRT
<213> ORGANISM: Homo sapiens
<220> FEATURE:
<221> NAME/KEY: misc_feature
<223> OTHER INFORMATION: IFN alpha-21

<400> SEQUENCE: 47

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 48
<211> LENGTH: 166
<212> TYPE: PRT
<213> ORGANISM: Homo sapiens
<220> FEATURE:
<221> NAME/KEY: misc_feature
<223> OTHER INFORMATION: IFN beta-1

<400> SEQUENCE: 48

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45
```

-continued

Gln Phe Gln Lys Glu Asp Ala Ala Leu Thr Ile Tyr Glu Met Leu Gln
         50                  55                  60

Asn Ile Phe Ala Ile Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                 85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 49
<211> LENGTH: 143
<212> TYPE: PRT
<213> ORGANISM: Homo sapiens
<220> FEATURE:
<221> NAME/KEY: misc_feature
<223> OTHER INFORMATION: IFN gamma

<400> SEQUENCE: 49

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly Arg Arg Ala Ser Gln
    130                 135                 140

<210> SEQ ID NO 50
<211> LENGTH: 132
<212> TYPE: PRT
<213> ORGANISM: Homo sapiens
<220> FEATURE:
<221> NAME/KEY: misc_feature
<223> OTHER INFORMATION: IL-17A

<400> SEQUENCE: 50

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
            20                  25                  30

```
Thr Asn Thr Asn Pro Lys Arg Ser Asp Tyr Tyr Asn Arg Ser Thr
            35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                 85                  90                  95

Leu Val Leu Arg Arg Glu Pro His Cys Pro Asn Ser Phe Arg Leu
                100                 105                 110

Glu Lys Ile Leu Val Ser Val Gly Cys Thr Cys Val Thr Pro Ile Val
                115                 120                 125

His His Val Ala
        130

<210> SEQ ID NO 51
<211> LENGTH: 133
<212> TYPE: PRT
<213> ORGANISM: Homo sapiens
<220> FEATURE:
<221> NAME/KEY: misc_feature
<223> OTHER INFORMATION: IL-17F

<400> SEQUENCE: 51

Arg Lys Ile Pro Lys Val Gly His Thr Phe Phe Gln Lys Pro Glu Ser
 1               5                  10                  15

Cys Pro Pro Val Pro Gly Gly Ser Met Lys Leu Asp Ile Gly Ile Ile
                20                  25                  30

Asn Glu Asn Gln Arg Val Ser Met Ser Arg Asn Ile Glu Ser Arg Ser
            35                  40                  45

Thr Ser Pro Trp Asn Tyr Thr Val Thr Trp Asp Pro Asn Arg Tyr Pro
 50                  55                  60

Ser Glu Val Val Gln Ala Gln Cys Arg Asn Leu Gly Cys Ile Asn Ala
 65                  70                  75                  80

Gln Gly Lys Glu Asp Ile Ser Met Asn Ser Val Pro Ile Gln Gln Glu
                 85                  90                  95

Thr Leu Val Val Arg Arg Lys His Gln Gly Cys Ser Val Ser Phe Gln
                100                 105                 110

Leu Glu Lys Val Leu Val Thr Val Gly Cys Thr Cys Val Thr Pro Val
                115                 120                 125

Ile His His Val Gln
        130

<210> SEQ ID NO 52
<211> LENGTH: 170
<212> TYPE: PRT
<213> ORGANISM: Homo sapiens
<220> FEATURE:
<221> NAME/KEY: misc_feature
<223> OTHER INFORMATION: IL-23 alpha (p19)

<400> SEQUENCE: 52

Arg Ala Val Pro Gly Gly Ser Ser Pro Ala Trp Thr Gln Cys Gln Gln
 1               5                  10                  15

Leu Ser Gln Lys Leu Cys Thr Leu Ala Trp Ser Ala His Pro Leu Val
                20                  25                  30

Gly His Met Asp Leu Arg Glu Glu Gly Asp Glu Glu Thr Thr Asn Asp
            35                  40                  45
```

-continued

```
Val Pro His Ile Gln Cys Gly Asp Gly Cys Asp Pro Gln Gly Leu Arg
 50                  55                  60

Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
                100                 105                 110

Ser Gln Leu Leu Gln Pro Glu Gly His His Trp Glu Thr Gln Gln Ile
                115                 120                 125

Pro Ser Leu Ser Pro Ser Gln Pro Trp Gln Arg Leu Leu Leu Arg Phe
130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170
```

<210> SEQ ID NO 53
<211> LENGTH: 133
<212> TYPE: PRT
<213> ORGANISM: Homo sapiens
<220> FEATURE:
<221> NAME/KEY: misc_feature
<223> OTHER INFORMATION: IL-3

<400> SEQUENCE: 53

```
Ala Pro Met Thr Gln Thr Thr Pro Leu Lys Thr Ser Trp Val Asn Cys
 1               5                  10                  15

Ser Asn Met Ile Asp Glu Ile Ile Thr His Leu Lys Gln Pro Pro Leu
                 20                  25                  30

Pro Leu Leu Asp Phe Asn Asn Leu Asn Gly Glu Asp Gln Asp Ile Leu
                 35                  40                  45

Met Glu Asn Asn Leu Arg Arg Pro Asn Leu Glu Ala Phe Asn Arg Ala
 50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Arg Lys Leu Thr
                100                 105                 110

Phe Tyr Leu Lys Thr Leu Glu Asn Ala Gln Ala Gln Gln Thr Thr Leu
                115                 120                 125

Ser Leu Ala Ile Phe
130
```

<210> SEQ ID NO 54
<211> LENGTH: 129
<212> TYPE: PRT
<213> ORGANISM: Homo sapiens
<220> FEATURE:
<221> NAME/KEY: misc_feature
<223> OTHER INFORMATION: IL-4

<400> SEQUENCE: 54

```
His Lys Cys Asp Ile Thr Leu Gln Glu Ile Ile Lys Thr Leu Asn Ser
 1               5                  10                  15

Leu Thr Glu Gln Lys Thr Leu Cys Thr Glu Leu Thr Val Thr Asp Ile
                 20                  25                  30
```

```
Phe Ala Ala Ser Lys Asn Thr Thr Glu Lys Glu Thr Phe Cys Arg Ala
             35                  40                  45

Ala Thr Val Leu Arg Gln Phe Tyr Ser His His Glu Lys Asp Thr Arg
 50                  55                  60

Cys Leu Gly Ala Thr Ala Gln Gln Phe His Arg His Lys Gln Leu Ile
 65                  70                  75                  80

Arg Phe Leu Lys Arg Leu Asp Arg Asn Leu Trp Gly Leu Ala Gly Leu
                 85                  90                  95

Asn Ser Cys Pro Val Lys Glu Ala Asn Gln Ser Thr Leu Glu Asn Phe
                100                 105                 110

Leu Glu Arg Leu Lys Thr Ile Met Arg Glu Lys Tyr Ser Lys Cys Ser
            115                 120                 125

Ser

<210> SEQ ID NO 55
<211> LENGTH: 115
<212> TYPE: PRT
<213> ORGANISM: Homo sapiens

<400> SEQUENCE: 55

Ile Pro Thr Glu Ile Pro Thr Ser Ala Leu Val Lys Glu Thr Leu Ala
 1               5                  10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
 65                  70                  75                  80

Gly Gln Lys Lys Lys Cys Gly Glu Glu Arg Arg Arg Val Asn Gln Phe
                 85                  90                  95

Leu Asp Tyr Leu Gln Glu Phe Leu Gly Val Met Asn Thr Glu Trp Ile
                100                 105                 110

Ile Glu Ser
        115

<210> SEQ ID NO 56
<211> LENGTH: 183
<212> TYPE: PRT
<213> ORGANISM: Homo sapiens
<220> FEATURE:
<221> NAME/KEY: misc_feature
<223> OTHER INFORMATION: IL-6

<400> SEQUENCE: 56

Val Pro Pro Gly Glu Asp Ser Lys Asp Val Ala Ala Pro His Arg Gln
 1               5                  10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
 65                  70                  75                  80

Thr Cys Leu Val Lys Ile Ile Thr Gly Leu Leu Glu Phe Glu Val Tyr
```

```
                          85                  90                  95
Leu Glu Tyr Leu Gln Asn Arg Phe Glu Ser Ser Glu Glu Ala Arg
                100                 105                 110

Ala Val Gln Met Ser Thr Lys Val Leu Ile Gln Phe Leu Lys Lys
            115                 120                 125

Ala Lys Asn Leu Asp Ala Ile Thr Thr Pro Asp Pro Thr Thr Asn Ala
        130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
                180

<210> SEQ ID NO 57
<211> LENGTH: 126
<212> TYPE: PRT
<213> ORGANISM: Homo sapiens
<220> FEATURE:
<221> NAME/KEY: misc_feature
<223> OTHER INFORMATION: IL-9

<400> SEQUENCE: 57

Gln Gly Cys Pro Thr Leu Ala Gly Ile Leu Asp Ile Asn Phe Leu Ile
1               5                   10                  15

Asn Lys Met Gln Glu Asp Pro Ala Ser Lys Cys His Cys Ser Ala Asn
            20                  25                  30

Val Thr Ser Cys Leu Cys Leu Gly Ile Pro Ser Asp Asn Cys Thr Arg
        35                  40                  45

Pro Cys Phe Ser Glu Arg Leu Ser Gln Met Thr Asn Thr Thr Met Gln
    50                  55                  60

Thr Arg Tyr Pro Leu Ile Phe Ser Arg Val Lys Lys Ser Val Glu Val
65                  70                  75                  80

Leu Lys Asn Asn Lys Cys Pro Tyr Phe Ser Cys Glu Gln Pro Cys Asn
                85                  90                  95

Gln Thr Thr Ala Gly Asn Ala Leu Thr Phe Leu Lys Ser Leu Leu Glu
            100                 105                 110

Ile Phe Gln Lys Glu Lys Met Arg Gly Met Arg Gly Lys Ile
        115                 120                 125

<210> SEQ ID NO 58
<211> LENGTH: 178
<212> TYPE: PRT
<213> ORGANISM: Homo sapiens
<220> FEATURE:
<221> NAME/KEY: misc_feature
<223> OTHER INFORMATION: IL-11

<400> SEQUENCE: 58

Pro Gly Pro Pro Gly Pro Pro Arg Val Ser Pro Asp Pro Arg Ala
1               5                   10                  15

Glu Leu Asp Ser Thr Val Leu Leu Thr Arg Ser Leu Leu Ala Asp Thr
            20                  25                  30

Arg Gln Leu Ala Ala Gln Leu Arg Asp Lys Phe Pro Ala Asp Gly Asp
        35                  40                  45

His Asn Leu Asp Ser Leu Pro Thr Leu Ala Met Ser Ala Gly Ala Leu
    50                  55                  60

Gly Ala Leu Gln Leu Pro Gly Val Leu Thr Arg Leu Arg Ala Asp Leu
```

```
                65                  70                  75                  80
Leu Ser Tyr Leu Arg His Val Gln Trp Leu Arg Arg Ala Gly Gly Ser
                85                  90                  95

Ser Leu Lys Thr Leu Glu Pro Glu Leu Gly Thr Leu Gln Ala Arg Leu
                100                 105                 110

Asp Arg Leu Leu Arg Arg Leu Gln Leu Leu Met Ser Arg Leu Ala Leu
                115                 120                 125

Pro Gln Pro Pro Pro Asp Pro Pro Ala Pro Pro Leu Ala Pro Pro Ser
        130                 135                 140

Ser Ala Trp Gly Gly Ile Arg Ala Ala His Ala Ile Leu Gly Gly Leu
145                 150                 155                 160

His Leu Thr Leu Asp Trp Ala Val Arg Gly Leu Leu Leu Leu Lys Thr
                165                 170                 175

Arg Leu

<210> SEQ ID NO 59
<211> LENGTH: 122
<212> TYPE: PRT
<213> ORGANISM: Homo sapiens
<220> FEATURE:
<221> NAME/KEY: misc_feature
<223> OTHER INFORMATION: IL-13

<400> SEQUENCE: 59

Leu Thr Cys Leu Gly Gly Phe Ala Ser Pro Gly Pro Val Pro Pro Ser
1               5                   10                  15

Thr Ala Leu Arg Glu Leu Ile Glu Glu Leu Val Asn Ile Thr Gln Asn
                20                  25                  30

Gln Lys Ala Pro Leu Cys Asn Gly Ser Met Val Trp Ser Ile Asn Leu
            35                  40                  45

Thr Ala Gly Met Tyr Cys Ala Ala Leu Glu Ser Leu Ile Asn Val Ser
        50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
                100                 105                 110

Lys Lys Leu Phe Arg Glu Gly Arg Phe Asn
            115                 120

<210> SEQ ID NO 60
<211> LENGTH: 215
<212> TYPE: PRT
<213> ORGANISM: Homo sapiens
<220> FEATURE:
<221> NAME/KEY: misc_feature
<223> OTHER INFORMATION: IL-27 alpha (p28)

<400> SEQUENCE: 60

Phe Pro Arg Pro Pro Gly Arg Pro Gln Leu Ser Leu Gln Glu Leu Arg
1               5                   10                  15

Arg Glu Phe Thr Val Ser Leu His Leu Ala Arg Lys Leu Leu Ser Glu
                20                  25                  30

Val Arg Gly Gln Ala His Arg Phe Ala Glu Ser His Leu Pro Gly Val
            35                  40                  45

Asn Leu Tyr Leu Leu Pro Leu Gly Glu Gln Leu Pro Asp Val Ser Leu
        50                  55                  60
```

-continued

Thr Phe Gln Ala Trp Arg Arg Leu Ser Asp Pro Glu Arg Leu Cys Phe
65                  70                  75                  80

Ile Ser Thr Thr Leu Gln Pro Phe His Ala Leu Leu Gly Gly Leu Gly
                85                  90                  95

Thr Gln Gly Arg Trp Thr Asn Met Glu Arg Met Gln Leu Trp Ala Met
            100                 105                 110

Arg Leu Asp Leu Arg Asp Leu Gln Arg His Leu Arg Phe Gln Val Leu
        115                 120                 125

Ala Ala Gly Phe Asn Leu Pro Glu Glu Glu Glu Glu Glu Glu Glu Glu
130                 135                 140

Glu Glu Glu Glu Arg Lys Gly Leu Leu Pro Gly Ala Leu Gly Ser Ala
145                 150                 155                 160

Leu Gln Gly Pro Ala Gln Val Ser Trp Pro Gln Leu Leu Ser Thr Tyr
                165                 170                 175

Arg Leu Leu His Ser Leu Glu Leu Val Leu Ser Arg Ala Val Arg Glu
            180                 185                 190

Leu Leu Leu Leu Ser Lys Ala Gly His Ser Val Trp Pro Leu Gly Phe
        195                 200                 205

Pro Thr Leu Ser Pro Gln Pro
    210                 215

<210> SEQ ID NO 61
<211> LENGTH: 209
<212> TYPE: PRT
<213> ORGANISM: Homo sapiens
<220> FEATURE:
<221> NAME/KEY: misc_feature
<223> OTHER INFORMATION: IL-27 beta (EBI3), IL-35 beta

<400> SEQUENCE: 61

Arg Lys Gly Pro Pro Ala Ala Leu Thr Leu Pro Arg Val Gln Cys Arg
1               5                   10                  15

Ala Ser Arg Tyr Pro Ile Ala Val Asp Cys Ser Trp Thr Leu Pro Pro
            20                  25                  30

Ala Pro Asn Ser Thr Ser Pro Val Ser Phe Ile Ala Thr Tyr Arg Leu
        35                  40                  45

Gly Met Ala Ala Arg Gly His Ser Trp Pro Cys Leu Gln Gln Thr Pro
    50                  55                  60

Thr Ser Thr Ser Cys Thr Ile Thr Asp Val Gln Leu Phe Ser Met Ala
65                  70                  75                  80

Pro Tyr Val Leu Asn Val Thr Ala Val His Pro Trp Gly Ser Ser Ser
                85                  90                  95

Ser Phe Val Pro Phe Ile Thr Glu His Ile Ile Lys Pro Asp Pro Pro
            100                 105                 110

Glu Gly Val Arg Leu Ser Pro Leu Ala Glu Arg Gln Leu Gln Val Gln
        115                 120                 125

Trp Glu Pro Pro Gly Ser Trp Pro Phe Pro Glu Ile Phe Ser Leu Lys
    130                 135                 140

Tyr Trp Ile Arg Tyr Lys Arg Gln Gly Ala Ala Arg Phe His Arg Val
145                 150                 155                 160

Gly Pro Ile Glu Ala Thr Ser Phe Ile Leu Arg Ala Val Arg Pro Arg
                165                 170                 175

Ala Arg Tyr Tyr Val Gln Val Ala Ala Gln Asp Leu Thr Asp Tyr Gly
            180                 185                 190

Glu Leu Ser Asp Trp Ser Leu Pro Ala Thr Ala Thr Met Ser Leu Gly 195                 200                 205
Lys

<210> SEQ ID NO 62
<211> LENGTH: 166
<212> TYPE: PRT
<213> ORGANISM: Homo sapiens
<220> FEATURE:
<221> NAME/KEY: misc_feature
<223> OTHER INFORMATION: Erythropoietin

<400> SEQUENCE: 62

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 63
<211> LENGTH: 178
<212> TYPE: PRT
<213> ORGANISM: Homo sapiens
<220> FEATURE:
<221> NAME/KEY: misc_feature
<223> OTHER INFORMATION: G-CSF

<400> SEQUENCE: 63

Ala Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Val Ser Glu Cys Ala Thr Tyr Lys Leu Cys His Pro
        35                  40                  45

Glu Glu Leu Val Leu Leu Gly His Ser Leu Gly Ile Pro Trp Ala Pro
    50                  55                  60

Leu Ser Ser Cys Pro Ser Gln Ala Leu Gln Leu Ala Gly Cys Leu Ser
65                  70                  75                  80

Gln Leu His Ser Gly Leu Phe Leu Tyr Gln Gly Leu Leu Gln Ala Leu
                85                  90                  95

Glu Gly Ile Ser Pro Glu Leu Gly Pro Thr Leu Asp Thr Leu Gln Leu
            100                 105                 110

-continued

```
Asp Val Ala Asp Phe Ala Thr Thr Ile Trp Gln Gln Met Glu Glu Leu
            115                 120                 125

Gly Met Ala Pro Ala Leu Gln Pro Thr Gln Gly Ala Met Pro Ala Phe
        130                 135                 140

Ala Ser Ala Phe Gln Arg Arg Ala Gly Gly Val Leu Val Ala Ser His
145                 150                 155                 160

Leu Gln Ser Phe Leu Glu Val Ser Tyr Arg Val Leu Arg His Leu Ala
                165                 170                 175

Gln Pro

<210> SEQ ID NO 64
<211> LENGTH: 191
<212> TYPE: PRT
<213> ORGANISM: Homo sapiens
<220> FEATURE:
<221> NAME/KEY: misc_feature
<223> OTHER INFORMATION: Growth hormone

<400> SEQUENCE: 64

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 65
<211> LENGTH: 199
<212> TYPE: PRT
<213> ORGANISM: Homo sapiens
<220> FEATURE:
<221> NAME/KEY: misc_feature
<223> OTHER INFORMATION: Prolactin

<400> SEQUENCE: 65

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30
```

```
Ser Ser Glu Met Phe Ser Glu Phe Asp Lys Arg Tyr Thr His Gly Arg
         35                  40                  45

Gly Phe Ile Thr Lys Ala Ile Asn Ser Cys His Thr Ser Ser Leu Ala
 50                  55                  60

Thr Pro Glu Asp Lys Glu Gln Ala Gln Met Asn Gln Lys Asp Phe
 65              70                  75                  80

Leu Ser Leu Ile Val Ser Ile Leu Arg Ser Trp Asn Glu Pro Leu Tyr
             85                  90                  95

His Leu Val Thr Glu Val Arg Gly Met Gln Glu Ala Pro Glu Ala Ile
             100                 105                 110

Leu Ser Lys Ala Val Glu Ile Glu Glu Gln Thr Lys Arg Leu Leu Glu
             115                 120                 125

Gly Met Glu Leu Ile Val Ser Gln Val His Pro Glu Thr Lys Glu Asn
 130                 135                 140

Glu Ile Tyr Pro Val Trp Ser Gly Leu Pro Ser Leu Gln Met Ala Asp
 145                 150                 155                 160

Glu Glu Ser Arg Leu Ser Ala Tyr Tyr Asn Leu Leu His Cys Leu Arg
                 165                 170                 175

Arg Asp Ser His Lys Ile Asp Asn Tyr Leu Lys Leu Leu Lys Cys Arg
                 180                 185                 190

Ile Ile His Asn Asn Asn Cys
             195
```

<210> SEQ ID NO 66
<211> LENGTH: 227
<212> TYPE: PRT
<213> ORGANISM: Homo sapiens
<220> FEATURE:
<221> NAME/KEY: misc_feature
<223> OTHER INFORMATION: Oncostatin M

<400> SEQUENCE: 66

```
Ala Ala Ile Gly Ser Cys Ser Lys Glu Tyr Arg Val Leu Leu Gly Gln
 1               5                  10                  15

Leu Gln Lys Gln Thr Asp Leu Met Gln Asp Thr Ser Arg Leu Leu Asp
             20                  25                  30

Pro Tyr Ile Arg Ile Gln Gly Leu Asp Val Pro Lys Leu Arg Glu His
             35                  40                  45

Cys Arg Glu Arg Pro Gly Ala Phe Pro Ser Glu Glu Thr Leu Arg Gly
 50                  55                  60

Leu Gly Arg Arg Gly Phe Leu Gln Thr Leu Asn Ala Thr Leu Gly Cys
 65                  70                  75                  80

Val Leu His Arg Leu Ala Asp Leu Glu Gln Arg Leu Pro Lys Ala Gln
                 85                  90                  95

Asp Leu Glu Arg Ser Gly Leu Asn Ile Glu Asp Leu Glu Lys Leu Gln
             100                 105                 110

Met Ala Arg Pro Asn Ile Leu Gly Leu Arg Asn Asn Ile Tyr Cys Met
             115                 120                 125

Ala Gln Leu Leu Asp Asn Ser Asp Thr Ala Glu Pro Thr Lys Ala Gly
 130                 135                 140

Arg Gly Ala Ser Gln Pro Pro Thr Pro Thr Pro Ala Ser Asp Ala Phe
 145                 150                 155                 160

Gln Arg Lys Leu Glu Gly Cys Arg Phe Leu His Gly Tyr His Arg Phe
                 165                 170                 175

Met His Ser Val Gly Arg Val Phe Ser Lys Trp Gly Glu Ser Pro Asn
             180                 185                 190
```

Arg Ser Arg Arg His Ser Pro His Gln Ala Leu Arg Lys Gly Val Arg
            195                 200                 205

Arg Thr Arg Pro Ser Arg Lys Gly Lys Arg Leu Met Thr Arg Gly Gln
210                 215                 220

Leu Pro Arg
225

<210> SEQ ID NO 67
<211> LENGTH: 180
<212> TYPE: PRT
<213> ORGANISM: Homo sapiens
<220> FEATURE:
<221> NAME/KEY: misc_feature
<223> OTHER INFORMATION: Leukemia inhibitory factor

<400> SEQUENCE: 67

Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180

<210> SEQ ID NO 68
<211> LENGTH: 146
<212> TYPE: PRT
<213> ORGANISM: Homo sapiens
<220> FEATURE:
<221> NAME/KEY: misc_feature
<223> OTHER INFORMATION: IL-22

<400> SEQUENCE: 68

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

```
Phe Thr Leu Glu Glu Val Leu Phe Pro Gln Ser Asp Arg Phe Gln Pro
 65                  70                  75                  80

Tyr Met Gln Glu Val Val Pro Phe Leu Ala Arg Leu Ser Asn Arg Leu
                 85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
130                 135                 140

Cys Ile
145

<210> SEQ ID NO 69
<211> LENGTH: 160
<212> TYPE: PRT
<213> ORGANISM: Homo sapiens
<220> FEATURE:
<221> NAME/KEY: misc_feature
<223> OTHER INFORMATION: IL-10

<400> SEQUENCE: 69

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
             20                  25                  30

Val Lys Thr Phe Phe Gln Met Lys Asp Gln Leu Asp Asn Leu Leu Leu
         35                  40                  45

Lys Glu Ser Leu Leu Glu Asp Phe Lys Gly Tyr Leu Gly Cys Gln Ala
     50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 70
<211> LENGTH: 12
<212> TYPE: PRT
<213> ORGANISM: Artificial Sequence
<220> FEATURE:
<223> OTHER INFORMATION: spacer (IgG4hinge)

<400> SEQUENCE: 70

Glu Ser Lys Tyr Gly Pro Pro Cys Pro Pro Cys Pro
1               5                   10

<210> SEQ ID NO 71
<211> LENGTH: 36
<212> TYPE: PRT
<213> ORGANISM: Artificial Sequence
<220> FEATURE:
```

<223> OTHER INFORMATION: spacer (IgG4hinge)

<400> SEQUENCE: 71

```
Gly Ala Ala Thr Cys Thr Ala Ala Gly Thr Ala Cys Gly Gly Ala Cys
1               5                   10                  15
Cys Gly Cys Cys Cys Thr Gly Cys Cys Cys Cys Thr Thr Gly
            20                  25                  30
Cys Cys Cys Thr
        35
```

<210> SEQ ID NO 72
<211> LENGTH: 119
<212> TYPE: PRT
<213> ORGANISM: Artificial Sequence
<220> FEATURE:
<223> OTHER INFORMATION: Hinge-CH3 spacer

<400> SEQUENCE: 72

```
Glu Ser Lys Tyr Gly Pro Pro Cys Pro Pro Cys Pro Gly Gln Pro Arg
1               5                   10                  15
Glu Pro Gln Val Tyr Thr Leu Pro Pro Ser Gln Glu Glu Met Thr Lys
            20                  25                  30
Asn Gln Val Ser Leu Thr Cys Leu Val Lys Gly Phe Tyr Pro Ser Asp
        35                  40                  45
Ile Ala Val Glu Trp Glu Ser Asn Gly Gln Pro Glu Asn Asn Tyr Lys
    50                  55                  60
Thr Thr Pro Pro Val Leu Asp Ser Asp Gly Ser Phe Phe Leu Tyr Ser
65                  70                  75                  80
Arg Leu Thr Val Asp Lys Ser Arg Trp Gln Glu Gly Asn Val Phe Ser
                85                  90                  95
Cys Ser Val Met His Glu Ala Leu His Asn His Tyr Thr Gln Lys Ser
            100                 105                 110
Leu Ser Leu Ser Leu Gly Lys
        115
```

<210> SEQ ID NO 73
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 73

```
Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
```

```
            115                 120                 125
Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Lys
225

<210> SEQ ID NO 74
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 74

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
                35                  40                  45

Glu Lys Glu Glu Gln Glu Glu Arg Glu Thr Lys Thr Pro Glu Cys Pro
        50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
```

```
                    245                 250                 255
Cys Val Val Ser His Glu Asp Ser Arg Thr Leu Leu Asn Ala Ser Arg
            260                 265                 270

Ser Leu Glu Val Ser Tyr Val Thr Asp His
            275                 280

<210> SEQ ID NO 75
<211> LENGTH: 357
<212> TYPE: PRT
<213> ORGANISM: Artificial Sequence
<220> FEATURE:
<223> OTHER INFORMATION: tEGFR

<400> SEQUENCE: 75

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
            290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
```

-continued

```
                        325                 330                 335
Thr Gly Met Val Gly Ala Leu Leu Leu Leu Val Val Ala Leu Gly
            340                 345                 350

Ile Gly Leu Phe Met
        355

<210> SEQ ID NO 76
<211> LENGTH: 24
<212> TYPE: PRT
<213> ORGANISM: Artificial Sequence
<220> FEATURE:
<223> OTHER INFORMATION: T2A

<400> SEQUENCE: 76

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 77
<211> LENGTH: 27
<212> TYPE: PRT
<213> ORGANISM: Homo sapiens
<220> FEATURE:
<221> NAME/KEY: misc_feature
<223> OTHER INFORMATION: CD28 (amino acids 153-179 of Accession No.
      P10747)

<400> SEQUENCE: 77

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 78
<211> LENGTH: 66
<212> TYPE: PRT
<213> ORGANISM: Homo sapiens
<220> FEATURE:
<221> NAME/KEY: misc_feature
<223> OTHER INFORMATION: CD28 (amino acids 114-179 of Accession No.
      P10747)

<400> SEQUENCE: 78

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 79
<211> LENGTH: 41
<212> TYPE: PRT
<213> ORGANISM: Homo sapiens
<220> FEATURE:
<221> NAME/KEY: misc_feature
<223> OTHER INFORMATION: CD28 (amino acids 180-220 of P10747)

<400> SEQUENCE: 79
```

-continued

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 80
<211> LENGTH: 41
<212> TYPE: PRT
<213> ORGANISM: Artificial Sequence
<220> FEATURE:
<223> OTHER INFORMATION: CD28 (LL to GG)

<400> SEQUENCE: 80

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 81
<211> LENGTH: 42
<212> TYPE: PRT
<213> ORGANISM: Homo sapiens
<220> FEATURE:
<221> NAME/KEY: misc_feature
<223> OTHER INFORMATION: 4-1BB (amino acids 214-255 of Q07011.1)

<400> SEQUENCE: 81

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 82
<211> LENGTH: 112
<212> TYPE: PRT
<213> ORGANISM: Artificial Sequence
<220> FEATURE:
<223> OTHER INFORMATION: CD3 zeta

<400> SEQUENCE: 82

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 83
<211> LENGTH: 112
<212> TYPE: PRT
<213> ORGANISM: Artificial Sequence
<220> FEATURE:
<223> OTHER INFORMATION: CD3 zeta

<400> SEQUENCE: 83
```

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 84
<211> LENGTH: 112
<212> TYPE: PRT
<213> ORGANISM: Artificial Sequence
<220> FEATURE:
<223> OTHER INFORMATION: CD3 zeta

<400> SEQUENCE: 84
```

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 85
<211> LENGTH: 33
<212> TYPE: DNA
<213> ORGANISM: Homo sapiens
<220> FEATURE:
<221> NAME/KEY: misc_feature
<223> OTHER INFORMATION: Epo HRE

<400> SEQUENCE: 85
gccctacgtg ctgtctcaca cagcctgtct gac                              33

<210> SEQ ID NO 86
<211> LENGTH: 35
```

```
<212> TYPE: DNA
<213> ORGANISM: Homo sapiens
<220> FEATURE:
<221> NAME/KEY: misc_feature
<223> OTHER INFORMATION: VEGF-A HRE

<400> SEQUENCE: 86
ccacagtgca tacgtgggct ccaacaggtc ctctt                          35

<210> SEQ ID NO 87
<211> LENGTH: 24
<212> TYPE: DNA
<213> ORGANISM: Homo sapiens
<220> FEATURE:
<221> NAME/KEY: misc_feature
<223> OTHER INFORMATION: PGK1 HRE

<400> SEQUENCE: 87
gacgtgacaa acgaagccga cgtc                                      24

<210> SEQ ID NO 88
<211> LENGTH: 24
<212> TYPE: DNA
<213> ORGANISM: Homo sapiens
<220> FEATURE:
<221> NAME/KEY: misc_feature
<223> OTHER INFORMATION: LdhA HRE

<400> SEQUENCE: 88
acacgtgggt tcccgcacgt ccgc                                      24

<210> SEQ ID NO 89
<211> LENGTH: 19
<212> TYPE: DNA
<213> ORGANISM: Homo sapiens
<220> FEATURE:
<221> NAME/KEY: misc_feature
<223> OTHER INFORMATION: ALDA HRE

<400> SEQUENCE: 89
gacgtgactc ggaccacat                                            19

<210> SEQ ID NO 90
<211> LENGTH: 31
<212> TYPE: DNA
<213> ORGANISM: Homo sapiens

<400> SEQUENCE: 90
gcccacacgc tcggtgcgtg cccagttgaa c                              31

<210> SEQ ID NO 91
<211> LENGTH: 10
<212> TYPE: DNA
<213> ORGANISM: Artificial Sequence
<220> FEATURE:
<223> OTHER INFORMATION: Exemplary CArG

<400> SEQUENCE: 91
ccttatttgg                                                      10

<210> SEQ ID NO 92
<211> LENGTH: 50
<212> TYPE: DNA
<213> ORGANISM: Artificial Sequence
<220> FEATURE:
<223> OTHER INFORMATION: Synthetic CArG sequence-containing promoter
```

```
<400> SEQUENCE: 92
cgcgtgatat ccttatttgg ccttatttgg ccttatttgg ccttatttgg            50

<210> SEQ ID NO 93
<211> LENGTH: 70
<212> TYPE: DNA
<213> ORGANISM: Artificial Sequence
<220> FEATURE:
<223> OTHER INFORMATION: Synthetic CArG sequence-containing promoter

<400> SEQUENCE: 93
cgcgtgatat ccttatttgg ccttatttgg ccttatttgg ccttatttgg ccttatttgg   60
ccttatttgg                                                         70

<210> SEQ ID NO 94
<211> LENGTH: 90
<212> TYPE: DNA
<213> ORGANISM: Artificial Sequence
<220> FEATURE:
<223> OTHER INFORMATION: Synthetic CArG sequence-containing promoter

<400> SEQUENCE: 94
cgcgtgatat ccttatttgg ccttatttgg ccttatttgg ccttatttgg ccttatttgg   60
ccttatttgg ccttatttgg ccttatttgg                                   90

<210> SEQ ID NO 95
<211> LENGTH: 110
<212> TYPE: DNA
<213> ORGANISM: Artificial Sequence
<220> FEATURE:
<223> OTHER INFORMATION: Synthetic CArG sequence-containing promoter

<400> SEQUENCE: 95
cgcgtgatat ccttatttgg ccttatttgg ccttatttgg ccttatttgg ccttatttgg   60
ccttatttgg ccttatttgg ccttatttgg ccttatttgg ccttatttgg            110

<210> SEQ ID NO 96
<211> LENGTH: 18
<212> TYPE: PRT
<213> ORGANISM: Artificial Sequence
<220> FEATURE:
<223> OTHER INFORMATION: T2A

<400> SEQUENCE: 96

Glu Gly Arg Gly Ser Leu Leu Thr Cys Gly Asp Val Glu Glu Asn Pro
1               5                   10                  15

Gly Pro

<210> SEQ ID NO 97
<211> LENGTH: 22
<212> TYPE: PRT
<213> ORGANISM: Artificial Sequence
<220> FEATURE:
<223> OTHER INFORMATION: P2A

<400> SEQUENCE: 97

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 98
```

```
<211> LENGTH: 19
<212> TYPE: PRT
<213> ORGANISM: Artificial Sequence
<220> FEATURE:
<223> OTHER INFORMATION: P2A

<400> SEQUENCE: 98

Ala Thr Asn Phe Ser Leu Leu Lys Gln Ala Gly Asp Val Glu Glu Asn
1               5                   10                  15

Pro Gly Pro

<210> SEQ ID NO 99
<211> LENGTH: 20
<212> TYPE: PRT
<213> ORGANISM: Artificial Sequence
<220> FEATURE:
<223> OTHER INFORMATION: E2A

<400> SEQUENCE: 99

Gln Cys Thr Asn Tyr Ala Leu Leu Lys Leu Ala Gly Asp Val Glu Ser
1               5                   10                  15

Asn Pro Gly Pro
            20

<210> SEQ ID NO 100
<211> LENGTH: 22
<212> TYPE: PRT
<213> ORGANISM: Artificial Sequence
<220> FEATURE:
<223> OTHER INFORMATION: F2A

<400> SEQUENCE: 100

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 101
<211> LENGTH: 335
<212> TYPE: PRT
<213> ORGANISM: Artificial Sequence
<220> FEATURE:
<223> OTHER INFORMATION: tEGFR

<400> SEQUENCE: 101

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125
```

```
Ile Ile Ser Gly Asn Lys Asn Leu Cys Tyr Ala Asn Thr Ile Asn Trp
130                 135                 140
Lys Lys Leu Phe Gly Thr Ser Gly Gln Lys Thr Lys Ile Ile Ser Asn
145                 150                 155                 160
Arg Gly Glu Asn Ser Cys Lys Ala Thr Gly Gln Val Cys His Ala Leu
                165                 170                 175
Cys Ser Pro Glu Gly Cys Trp Gly Pro Glu Pro Arg Asp Cys Val Ser
                180                 185                 190
Cys Arg Asn Val Ser Arg Gly Arg Glu Cys Val Asp Lys Cys Asn Leu
                195                 200                 205
Leu Glu Gly Glu Pro Arg Glu Phe Val Glu Asn Ser Glu Cys Ile Gln
210                 215                 220
Cys His Pro Glu Cys Leu Pro Gln Ala Met Asn Ile Thr Cys Thr Gly
225                 230                 235                 240
Arg Gly Pro Asp Asn Cys Ile Gln Cys Ala His Tyr Ile Asp Gly Pro
                245                 250                 255
His Cys Val Lys Thr Cys Pro Ala Gly Val Met Gly Glu Asn Asn Thr
                260                 265                 270
Leu Val Trp Lys Tyr Ala Asp Ala Gly His Val Cys His Leu Cys His
                275                 280                 285
Pro Asn Cys Thr Tyr Gly Cys Thr Gly Pro Gly Leu Glu Gly Cys Pro
290                 295                 300
Thr Asn Gly Pro Lys Ile Pro Ser Ile Ala Thr Gly Met Val Gly Ala
305                 310                 315                 320
Leu Leu Leu Leu Leu Val Val Ala Leu Gly Ile Gly Leu Phe Met
                325                 330                 335
```

<210> SEQ ID NO 102
<211> LENGTH: 1668
<212> TYPE: DNA
<213> ORGANISM: Artificial Sequence
<220> FEATURE:
<223> OTHER INFORMATION: Sc IL-12 G4S(3)

<400> SEQUENCE: 102

```
gctagcgcca ccatgcccct gctgctgctg ctgcctctgc tgtgggctgg cgcactggcc    60
atctgggagc tgaagaaaga cgtgtacgtg gtcgaactgg actggtatcc tgatgcccca   120
ggagagatgg tggtcctgac ttgcgacacc cccgaggaag atggcatcac ttggaccctg   180
gatcagagct ccgaggtgct gggaagcggc aaaacactga ctattcaggt caaggaattc   240
ggggacgctg acagtacac atgtcacaag ggaggagagg tgctgagcca ctccctgctg   300
ctgctgcata gaaagaaga cggcatctgg agcactgaca ttctgaaaga tcagaaggag   360
ccaaagaaca aaaccttcct gcgctgcgaa gcaaaaaatt atagcggccg gttcacctgt   420
tggtggctga ccacaatcag cacagatctg acttttttccg tgaagtctag tagggggtca   480
agcgacccac agggagtcac atgcggagca gctactctgt ccgccgagcg ggtgagagga   540
gataacaagg agtacgaata ttcagtcgag tgccaggaag acagcgcatg tcctgcagcc   600
gaggaatctc tgccaatcga agtgatggtc gatgccgtgc acaagctgaa atacgaaaac   660
tacacatcct ctttctttat ccgagacatc atcaagccag atccccctaa gaacctgcag   720
ctgaaacccc tgaagaattc tcgccaggtg gaggtcagtt gggaatacc agacacctgg   780
agcacacccc attcatattt cagcctgact tttgcgtgc aggtccaggg caagagtaaa   840
agagagaaga agacagggt gttcactgat aaaaccagcg ccacagtcat ctgtcggaag   900
```

| | |
|---|---|
| aacgcctcta ttagtgtgcg agctcaggat cggtactata gttcaagctg gtccgaatgg | 960 |
| gcttctgtgc cttgtagtgg aggaggagga agcggaggag gaggatccgg aggaggcggg | 1020 |
| tctagaaatc tgcctgtggc aaccccagac cccggcatgt tcccatgcct gcaccattcc | 1080 |
| cagaacctgc tgcgggcagt gtctaatatg ctgcagaagg ccagacagac cctggagttt | 1140 |
| taccccctgta catccgagga aatcgaccac gaggatatta ccaaggataa aacctctaca | 1200 |
| gtggaagctt gcctgcctct ggagctgaca aagaacgaat catgtctgaa tagcagggag | 1260 |
| acttccttca tcaccaacgg ctcttgcctg gccagtcgca agaccagctt catgatggct | 1320 |
| ctgtgcctgt cctctatcta cgaggacctg aagatgtatc aggtggaatt caaaaccatg | 1380 |
| aacgccaagc tgctgatgga ccctaaaagg cagatctttc tggatcagaa tatgctggct | 1440 |
| gtgattgacg agctgatgca ggcactgaac ttcaatagcg aaacagtccc ccagaagagt | 1500 |
| tcactggagg aacctgattt ctacaagact aaaatcaagc tgtgcattct gctgcacgct | 1560 |
| tttaggatcc gcgcagtgac cattgaccgc gtcatgagtt atctgaatgc ctcacaccat | 1620 |
| caccatcacc attggtccca tccacagttt gagaagtgat aactcgag | 1668 |

<210> SEQ ID NO 103
<211> LENGTH: 1683
<212> TYPE: DNA
<213> ORGANISM: Artificial Sequence
<220> FEATURE:
<223> OTHER INFORMATION: Sc IL-12 HBP BMP4

<400> SEQUENCE: 103

| | |
|---|---|
| gctagcgcca ccatgcccct gctgctgctg ctgcctctgc tgtgggctgg cgcactggcc | 60 |
| atctgggagc tgaagaaaga cgtgtacgtg gtcgaactgg actggtatcc tgatgcccca | 120 |
| ggggagatgg tggtcctgac ttgcgacacc cccgaggaag atggaatcac ttggaccctg | 180 |
| gatcagagct ccgaggtgct ggggtccgga aaaacactga ctattcaggt caaggaattc | 240 |
| ggcgacgctg gcagtacac atgtcacaag ggaggagagg tgctgagcca ctccctgctg | 300 |
| ctgctgcata agaaagaaga cggaatctgg tctactgaca ttctgaaaga tcagaaggag | 360 |
| cctaagaaca aaaccttcct gcggtgcgaa gcaaaaaatt atagcggccg gttcacctgt | 420 |
| tggtggctga ccacaatctc tacagatctg acttttagtg tgaagtctag taggggctca | 480 |
| agcgacccac agggagtcac atgcggagca gctactctga cgccgagag ggtgcgcggg | 540 |
| gataacaagg agtacgaata ttccgtcgag tgccaggaag actctgcatg tcctgcagcc | 600 |
| gaggaatccc tgccaatcga agtgatggtc gatgccgtgc acaagctgaa atacgaaaac | 660 |
| tacacatcct ctttctttat tagggacatc atcaagccag atccccctaa gaacctgcag | 720 |
| ctgaaacccc tgaagaattc acgccaggtg gaggtcagct gggaataccc agacacctgg | 780 |
| agcacacccc cattcatattt cagcctgact ttttgcgtgc aggtccaggg caagagcaaa | 840 |
| cgcgagaaga aagaccgagt gttcactgat aaaacctccg ctacagtcat ctgccgcaag | 900 |
| aacgcctcta ttagtgtgag agctcaggat aggtactata gttcaagctg gtccgaatgg | 960 |
| gcatctgtgc catgcagtgg aggaggagga agccggaaga aaaaccctaa ttgtcggaga | 1020 |
| cacggcgggg gaggctccag aaatctgcct gtggctaccc cagaccccgg gatgttccca | 1080 |
| tgcctgcacc atagtcagaa cctgctgagg gcagtgtcaa atatgctgca gaaggcccgc | 1140 |
| cagaccctgg agtttttaccc atgtacatct gaggaaatcg accacgagga tattaccaag | 1200 |
| gataaaacca gtacagtgga agcctgcctg cccctggagc tgacaaagaa cgaatcatgt | 1260 |
| ctgaatagcc gagagacttc cttcatcacc aacggctctt gcctggccag tcgcaagacc | 1320 |

```
agcttcatga tggctctgtg cctgtcctct atctacgagg acctgaagat gtatcaggtg    1380
gaattcaaaa ccatgaacgc caagctgctg atggacccca acggcagat ctttctggat     1440 cagaatatgc tggctgtgat tgacgagctg atgcaggcac tgaacttcaa ttctgaaaca    1500
gtcccccaga gagttcact ggaggaacct gatttctaca agactaaaat caagctgtgc     1560
attctgctgc acgcttttcg aatccgggca gtgaccattg acagagtcat gagctatctg    1620
aatgcctccc accatcacca tcaccattgg agccatcctc agtttgagaa gtgataactc    1680
gag                                                                   1683
```

<210> SEQ ID NO 104
<211> LENGTH: 1698
<212> TYPE: DNA
<213> ORGANISM: Artificial Sequence
<220> FEATURE:
<223> OTHER INFORMATION: Sc IL-12 HBP FBN

<400> SEQUENCE: 104

```
gctagcgcca ccatgcccct gctgctgctg ctgcctctgc tgtgggctgg cgcactggcc     60
atctgggagc tgaagaaaga cgtgtacgtg gtcgaactgg actggtatcc tgatgcccca    120
ggggagatgg tggtcctgac ttgcgacacc cccgaggaag atggaatcac ttggaccctg    180
gatcagagct ccgaggtgct ggggagcgga aaaacactga ctattcaggt caaggaattc    240
ggcgacgctg gcagtacac atgtcacaag ggaggagagg tgctgagcca ctccctgctg    300
ctgctgcata gaaagaaga cgggatctgg tctacagaca ttctgaaaga tcagaaggag    360
cctaagaaca aactttcct gcgctgcgaa gcaaaaaatt atagcggccg gttcacctgt   420
tggtggctga ccacaatctc tacagatctg acttttagtg tgaagtctag taggggatca    480
agcgacccac agggagtcac atgcggagca gctactctga gcgccgagcg ggtgagaggc    540
gataacaagg agtacgaata tagtgtcgag tgccaggaag actcagcatg tcctgcagcc    600
gaggaatccc tgccaatcga agtgatggtc gatgccgtgc acaagctgaa atacgaaaac    660
tacacatcct ctttctttat tcgggacatc atcaagccag atcccctaa gaacctgcag    720 ctgaaacccc tgaagaattc aagacaggtg gaggtcagct gggaataccc agacacctgg    780
tccacacccc attcatattt cagcctgacc ttttgcgtgc aggtccaggg caagtctaaa    840
agagagaaga agacagggt gttcactgat aaaaccagtg ctacagtcat ctgtagaaag    900
aacgcctcta ttagtgtgcg agctcaggat cggtactata gttcaagctg gtccgagtgg    960
gcatctgtgc cctgtagtgg aggcggggga tccaaaaaca tcagaagtc tgaacctctg   1020 atcggccgga gaaaactgg cggggaggc agcagaaatc tgcctgtggc taccccagat    1080
cccgggatgt tccatgcct gcaccatagc cagaacctgc tgagggcagt gtccaatatg   1140
ctgcagaagg cccgccagac cctggagttt acccatgta caagcgagga atcgaccac    1200 gaggatatta ctaaggacaa aacctccaca gtggaagcct gcctgccct ggagctgacc   1260 aagaacgaat catgtctgaa tagccgagag acttccttca tcaccaacgg ctcttgcctg   1320
gccagtcgca agaccagctt catgatggct ctgtgcctgt cctctatcta cgaggacctg   1380
aagatgtatc aggtggaatt caaaactatg aacgccaagc tgctgatgga ccccaaaagg   1440
cagatctttc tggatcagaa tatgctggct gtgattgacg agctgatgca ggcactgaac   1500
ttcaattctg aaaccgtccc ccagaagagt tcactggagg aacctgatt ctacaagaca   1560 aaaatcaagc tgtgcattct gctgcacgct tttaggatcc gcgcagtgac cattgaccgc   1620
```

```
gtcatgagct atctgaatgc ctcccaccat caccatcacc attggagcca tcctcagttt    1680
gagaagtgat aactcgag                                                   1698

<210> SEQ ID NO 105
<211> LENGTH: 1701
<212> TYPE: DNA
<213> ORGANISM: Artificial Sequence
<220> FEATURE:
<223> OTHER INFORMATION: Sc IL-12 HGFBP

<400> SEQUENCE: 105
gctagcgcca ccatgcccct gctgctgctg ctgcctctgc tgtgggctgg cgcactggcc      60
atctgggagc tgaagaaaga cgtgtacgtg gtcgaactgg actggtatcc tgatgcccca     120
ggggagatgg tggtcctgac ttgcgacacc cccgaggaag atggaatcac ttggaccctg     180
gatcagagct ccgaggtgct ggggtccgga aaaacactga ctattcaggt caaggaattc     240
ggcgacgctg gcagtacac atgtcacaag gaggagagg tgctgagcca ctccctgctg      300
ctgctgcata agaaagaaga cgggatctgg tctactgaca ttctgaaaga tcagaaggag     360
ccaaagaaca aaaccttcct gcgctgcgaa gcaaaaaatt atagcggccg gttcacctgt     420
tggtggctga ccacaatctc tacagatctg acttttagtg tgaagtctag taggggctca     480
agcgacccac agggagtcac atgcggagca gctactctga gcgccgagcg ggtgagaggg     540
gataacaagg agtacgaata ttccgtcgag tgccaggaag actctgcatg tcctgcagcc     600
gaggaatccc tgccaatcga agtgatggtc gatgccgtgc acaagctgaa atacgaaaac     660
tacacatcct ctttctttat tcgggacatc atcaagccag atccccctaa gaacctgcag     720
ctgaaacccc tgaagaattc aagacaggtg gaggtcagct gggaatacgc agacacctgg     780
agcacacccc attcatattt cagcctgact ttttgcgtgc aggtccaggg caagagcaaa     840
agagagaaga agacagggt gttcactgat aaaacctccg ctacagtcat ctgcagaaag     900
aacgcctcta ttagtgtgcg agctcaggat cggtactata gttcaagctg gtccgaatgg     960
gcatctgtgc cttgtagtgg aggcggggga agcgtgtgga actgggtctg ctttagggac    1020
gtgggatgtg attgggtcct gggaggagga ggctcccgca atctgcctgt ggctaccca    1080 gatcccggca tgttcccatg cctgcaccat agtcagaacc tgctgcgggc agtgtcaaat    1140
atgctgcaga aggccagaca gaccctggag ttttaccct gtacatctga ggaaatcgac    1200
cacgaggata ttaccaagga caaaaccagt acagtggaag cctgcctgcc tctggagctg    1260
acaaagaacg aatcatgtct gaatagccga gagcttcct tcatcaccaa cggctcttgc    1320
ctggccagtc gcaagaccag cttcatgatg gctctgtgcc tgtcctctat ctacgaggac    1380
ctgaagatgt atcaggtgga attcaaaacc atgaacgcca agctgctgat ggaccctaaa    1440
aggcagatct ttctggatca gaatatgctg gctgtgattg acgagctgat gcaggcactg    1500
aacttcaatt ctgaaacagt gccccagaag agttcactgg aggaacctga tttctacaag    1560
actaaaatca agctgtgcat tctgctgcac gcttttagga tccgcgcagt gaccattgac    1620
cgcgtcatga gctatctgaa tgcctcccac catcaccatc accattggag ccatccacag    1680
tttgagaagt gataactcga g                                              1701

<210> SEQ ID NO 106
<211> LENGTH: 1677
<212> TYPE: DNA
<213> ORGANISM: Artificial Sequence
<220> FEATURE:
<223> OTHER INFORMATION: Sc IL-12 EGFRBP
```

<400> SEQUENCE: 106

```
gctagcgcca ccatgcccct gctgctgctg ctgcctctgc tgtgggctgg cgcactggcc      60
atctgggagc tgaagaaaga cgtgtacgtg gtcgaactgg actggtatcc tgatgcccca     120
ggggagatgg tggtcctgac ttgcgacacc cccgaggaag atggaatcac ttggaccctg     180
gatcagagct ccgaggtgct ggggagcgga aaaacactga ctattcaggt caaggaattc     240
ggcgacgctg gcagtacac atgtcacaag ggcggggagg tgctgtctca cagtctgctg     300
ctgctgcata agaaagaaga cggaatctgg tctactgaca ttctgaaaga tcagaaggag     360
cctaagaaca aaaccttcct gcgctgcgaa gcaaaaaatt atagcggccg gttcacctgt     420
tggtggctga ccacaatctc aacagatctg acttttagcg tgaagtctag taggggctca     480
agcgacccac agggagtcac atgcggagca gctactctga gcgccgagcg ggtgagaggg     540
gataacaagg agtacgaata tagtgtcgag tgccaggaag actcagcatg tcctgcagcc     600
gaggaatccc tgccaatcga agtgatggtc gatgccgtgc acaagctgaa atacgaaaac     660
tacacatcct ctttctttat ccgagacatc atcaagccag atcccctaa gaacctgcag     720
ctgaaacccc tgaagaattc ccgccaggtg gaggtctctt gggaataccc agacacctgg     780
tccacacccc attcctattt ctctctgact ttttgcgtgc aggtccaggg caagtctaaa     840
agagagaaga agacaggg gttcactgat aaaaccagtg ctacagtcat ctgccgaaag     900
aacgcctcaa ttagcgtgcg agctcaggac cggtactata gttcaagctg gagtgaatgg     960
gcatcagtgc catgcagcgg aggaggagga tcctctgtgg ataaccctca cgtctgtggc    1020
ggaggaggca gcagaaatct gcctgtggct accccagacc ccgggatgtt cccatgcctg    1080
caccatagcc agaacctgct gcgggcagtg tccaatatgc tgcagaaggc cagacagacc    1140
ctggagttttt acccatgtac aagcgaggaa atcgaccacg aggatattac caaggataaa    1200
acctccacag tggaagcctg cctgccccctg gagctgacaa agaacgaatc ctgtctgaat    1260
tctagggaga ctagtttcat caccaacggc tcatgcctgg ccagccgcaa aacttccttt    1320
atgatggctc tgtgcctgag ttcaatctac gaggacctga gatgtatca ggtggaattc    1380
aaaaccatga acgccaagct gctgatggac cccaaaaggc agatctttct ggatcagaat    1440
atgctggctg tgattgacga gctgatgcag gcactgaact tcaattctga acagtccccc    1500
cagaagagct ccctggagga acctgatttc tacaagacta aaatcaagct gtgcattctg    1560
ctgcacgctt ttaggatccg cgcagtgacc attgaccgcg tcatgtctta tctgaatgcc    1620
agtcaccatc accatcacca ttggagccat cctcagtttg agaagtgata actcgag    1677
```

<210> SEQ ID NO 107
<211> LENGTH: 2394
<212> TYPE: DNA
<213> ORGANISM: Artificial Sequence
<220> FEATURE:
<223> OTHER INFORMATION: Sc IL-12 anti-EPCAM

<400> SEQUENCE: 107

```
gctagcgcca ccatgcctct gctgctgctg ctgccactgc tgtgggctgg cgcactggcc      60
atctgggagc tgaagaaaga cgtgtacgtg gtcgaactgg actggtatcc cgatgctcct     120
ggggagatgg tggtcctgac atgcgacact cccgaggaag atggaatcac atggactctg     180
gatcagagct ccgaggtcct ggaagcggc aaaaccctga caattcaggt gaaggaattc     240
ggggacgccg gacagtacac atgtcacaag ggcggggagg tgctgtctca cagtctgctg     300
```

```
ctgctgcata agaaagaaga cgggatctgg tctaccgaca ttctgaaaga tcagaaggag      360
cccaagaaca aaacattcct gaggtgcgaa gccaaaaatt atagcggacg ctttacctgt      420
tggtggctga ccacaatcag taccgatctg acattttcag tcaagtctag tcggggctca      480
agcgaccctc agggagtgac atgcggagca gctactctgt ctgccgagcg ggtcagaggg      540
gataacaagg agtacgaata ttctgtggag tgccaggaag acagtgcttg tccagcagcc      600
gaggaaagcc tgcccatcga ggtcatggtg gatgcagtgc acaagctgaa atacgaaaac      660
tacacatcct ctttctttat tcgggacatc atcaagccag atccccctaa gaacctgcag      720
ctgaaacccc tgaagaatag cagacaggtc gaggtgtcct gggaatacccc cgacacttgg      780 agcacccctc atagttattt ctcactgacc ttttgcgtcc aggtgcaggg caagtctaaa      840
agagagaaga aagacagggt cttcacagat aagaccagcg ccaccgtgat ctgtagaaag      900
aacgcatcaa ttagcgtgcg agcccaggat cggtactata gttcaagctg gagcgagtgg      960
gcctccgtgc catgctctgg aggaggagga tcacaggtcc agctggtgca gagcggagca     1020
gaagtgaaga acccggctc ctctgtcaaa gtgagttgta aggcctcagg cgggacttt      1080 agttcatacg caatctctgt ggtcgtgagg caggcaccag acagggact ggagtggatg      1140 ggaggcatca ttcctatctt cggcaccgcc aactacgctc agaagtttca ggggcgcgtg     1200
actattaccg ccgatgagtc cacatctact gcttatatgg agctgagctc cctgagaagc     1260
gaagacaccg ccgtgtacta ttgcgcaagg ggcctgctgt ggaattactg gggccagggg     1320
acactggtca ccgtgagcag caaactgagt ggaagcgcca gcgccccgcgg ctggaggaa     1380 ggagagttca gtgaagcccg ggtcgagact accctgaccc agtccctgc tacactgtcc      1440 gtgtctccag gagaacgcgc tacactgagc tgtcgagcaa gtcagtcagt gtcaagcaat     1500
ctggctgtcg tgtaccagca gaagccaggc caggcaccca gactgctgat ctatggggca     1560
agcacccggg ccacaggaat tccagctaga ttcagcggat ccggctctgg gaccgagttt     1620
accctgacaa tctcctctct gcagtccgaa gacttcgccg tgtactattg ccagcagtac     1680
aacaattggc cacccgggtt cacttttgga cccggcacca aagtcgatat taagggagga    1740
ggagggtccc ggaacctgcc tgtggcaact cctgacccag gcatgttccc atgcctgcac    1800
cattcccaga acctgctgcg agccgtgagc aatatgctgc agaaagcacg gcagacactg     1860
gagttttatc cttgtactag cgaggaaatc gaccacgagg atattacaaa ggataaaact     1920
tccaccgtgg aagcctgcct gccactggag ctgactaaga acgaaagctg tctgaattcc     1980
cgcgagactt ctttcatcac caatggcagt tgcctggcat cacgaaaaac cagctttatg     2040
atggccctgt gcctgagttc aatctacgag gacctgaaga tgtatcaggt ggaattcaaa     2100
acaatgaacg ccaagctgct gatggaccct aaaaggcaga tctttctgga tcagaatatg     2160
ctggccgtga ttgacgagct gatgcaggct ctgaacttca atagcgaaac tgtgccccag     2220
aagagctccc tggaggaacc tgatttctac aagaccaaaa tcaagctgtg cattctgctg     2280
cacgccttta ggatccgcgc tgtcaccatt gaccgcgtga tgtcctatct gaacgcctct     2340
caccatcacc atcaccattg gtcccatcca cagtttgaga agtgataact cgag           2394
```

<210> SEQ ID NO 108
<211> LENGTH: 12
<212> TYPE: PRT
<213> ORGANISM: Artificial Sequence
<220> FEATURE:
<223> OTHER INFORMATION: EGFR binding peptide

<400> SEQUENCE: 108

```
Tyr His Trp Tyr Gly Tyr Thr Pro Gln Asn Val Ile
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: EGFR binding peptide

<400> SEQUENCE: 109

```
Tyr Arg Trp Tyr Gly Tyr Thr Pro Gln Asn Val Ile
1               5                   10
```

<210> SEQ ID NO 110
<211> LENGTH: 6
<212> TYPE: PRT
<213> ORGANISM: Artificial Sequence
<220> FEATURE:
<223> OTHER INFORMATION: VEGFR3 binding peptide

<400> SEQUENCE: 110

```
Pro Cys Ala Ile Trp Phe
1               5
```

<210> SEQ ID NO 111
<211> LENGTH: 6
<212> TYPE: PRT
<213> ORGANISM: Artificial Sequence
<220> FEATURE:
<223> OTHER INFORMATION: VEGFR3 binding peptide

<400> SEQUENCE: 111

```
Trp Val Cys Ser Gly Gly
1               5
```

<210> SEQ ID NO 112
<211> LENGTH: 9
<212> TYPE: PRT
<213> ORGANISM: Artificial Sequence
<220> FEATURE:
<223> OTHER INFORMATION: NGR motif

<400> SEQUENCE: 112

```
Asn Gly Arg Asn Gly Arg Asn Gly Arg
1               5
```

<210> SEQ ID NO 113
<211> LENGTH: 9
<212> TYPE: PRT
<213> ORGANISM: Artificial Sequence
<220> FEATURE:
<223> OTHER INFORMATION: RGD motif

<400> SEQUENCE: 113

```
Arg Gly Asp Arg Gly Asp Arg Gly Asp
1               5
```

<210> SEQ ID NO 114
<211> LENGTH: 10
<212> TYPE: PRT
<213> ORGANISM: Artificial Sequence
<220> FEATURE:
<223> OTHER INFORMATION: NG2 proteoglycan binding peptide

<400> SEQUENCE: 114

```
Thr Ala Ala Ser Gly Val Arg Ser Met His
1               5                   10
```

<210> SEQ ID NO 115
<211> LENGTH: 10
<212> TYPE: PRT
<213> ORGANISM: Artificial Sequence
<220> FEATURE:
<223> OTHER INFORMATION: NG2 proteoglycan binding peptide

<400> SEQUENCE: 115

```
Leu Thr Leu Arg Trp Val Gly Leu Met Ser
1               5                   10
```

<210> SEQ ID NO 116
<211> LENGTH: 25
<212> TYPE: PRT
<213> ORGANISM: Artificial Sequence
<220> FEATURE:
<223> OTHER INFORMATION: HER2 binding peptide

<400> SEQUENCE: 116

```
Asn Lys Phe Asn Lys Gly Met Arg Tyr Trp Gly Ala Leu Gly Gly Asn
1               5                   10                  15

Gly Lys Arg Gly Ile Arg Gly Tyr Met
            20                  25
```

<210> SEQ ID NO 117
<211> LENGTH: 9
<212> TYPE: PRT
<213> ORGANISM: Artificial Sequence
<220> FEATURE:
<223> OTHER INFORMATION: EPCAM binding peptide

<400> SEQUENCE: 117

```
Tyr Glu Val His Thr Tyr Tyr Leu Asp
1               5
```

<210> SEQ ID NO 118
<211> LENGTH: 21
<212> TYPE: PRT
<213> ORGANISM: Artificial Sequence
<220> FEATURE:
<223> OTHER INFORMATION: VEGFR binding peptide

<400> SEQUENCE: 118

```
Ile Thr Met Gln Ile Met Arg Ile Lys Pro His Gln Gly Gln His Ile
1               5                   10                  15

Gly Glu Met Ser Phe
            20
```